(12) United States Patent
Sugiyama et al.

(10) Patent No.: US 7,432,100 B2
(45) Date of Patent: Oct. 7, 2008

(54) VARIANT ALDOLASE AND PROCESSES FOR PRODUCING AN OPTICALLY ACTIVE IHOG AND AN OPTICALLY ACTIVE MONATIN USING THE SAME

(75) Inventors: Masakazu Sugiyama, Kawasaki (JP); Tatsuki Kashiwagi, Kawasaki (JP); Kenichi Mori, Kawasaki (JP); Eiichiro Suzuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 157 days.

(21) Appl. No.: 11/080,628

(22) Filed: Mar. 16, 2005

(65) Prior Publication Data

US 2005/0244939 A1    Nov. 3, 2005

(30) Foreign Application Priority Data

Mar. 16, 2004    (JP) .............................. 2004-075256

(51) Int. Cl.
*C12N 9/88* (2006.01)
*C12N 1/12* (2006.01)
*C12N 15/74* (2006.01)
*C12N 9/10* (2006.01)
*C12P 17/12* (2006.01)
*C12P 21/06* (2006.01)

(52) U.S. Cl. .................. 435/232; 435/121; 435/252.3; 435/69.1; 435/471; 435/193; 536/23.2

(58) Field of Classification Search ....................... None
See application file for complete search history.

(56) References Cited

U.S. PATENT DOCUMENTS

2005/0009153 A1    1/2005    Sugiyama et al.
2005/0244939 A1    11/2005    Sugiyama et al.

OTHER PUBLICATIONS

Xu et al., A practical method for interpretatio of threading scores: An application of neural network. Statstica Sinica, 2002, vol. 12: 159-177.*
Whisstock et al., Prediction of protein function from protein sequence and strucuture. Q. Rev. Biophys., 2003, vol. 36(3): 307-340.*
U.S. Appl. No. 11/146,093, filed Jun. 7, 2005, Sugiyama, et al.
U.S. Appl. No. 11/080,628, filed Mar. 16, 2005, Sugiyama, et al.
U.S. Appl. No. 11/362,915, filed Feb. 28, 2006, Sugiyama, et al.
U.S. Appl. No. 11/561,665, filed Nov. 20, 2006, Sugiyama, et al.
U.S. Appl. No. 11/066,542, filed Feb. 28, 2005, Sugiyama, et al.

* cited by examiner

Primary Examiner—Rebecca E. Prouty
Assistant Examiner—Ganapathirama Raghu
(74) Attorney, Agent, or Firm—Oblon, Spivak, McClelland, Maier & Neustadt, P.C.

(57) ABSTRACT

The present invention relates to variant aldolase enzymes that are modified so as to produce IHOG (4-(indol-3-ylmethyl)-4-hydroxy-2-oxoglutaric acid: IHOG), a process for producing an optically active IHOG using the same, and a process for producing an optically active monatin.

4 Claims, 42 Drawing Sheets

Figure 9-1

```
CRYST1   94.380   94.380  111.490  90.00  90.00 120.00 P 63 2 2
ATOM      1  CB  SER A   2      62.908   5.460 -33.073  1.00 32.64
ATOM      2  OG  SER A   2      61.816   5.282 -32.172  1.00 35.63
ATOM      3  C   SER A   2      61.411   4.516 -34.814  1.00 28.24
ATOM      4  O   SER A   2      60.200   4.705 -34.679  1.00 28.32
ATOM      5  N   SER A   2      61.781   6.966 -34.707  1.00 31.48
ATOM      6  CA  SER A   2      62.416   5.625 -34.516  1.00 30.97
ATOM      7  N   LEU A   3      61.916   3.356 -35.211  1.00 24.37
ATOM      8  CA  LEU A   3      61.033   2.248 -35.508  1.00 21.49
ATOM      9  CB  LEU A   3      61.552   1.440 -36.694  1.00 19.79
ATOM     10  CG  LEU A   3      61.413   2.031 -38.098  1.00 18.53
ATOM     11  CD1 LEU A   3      61.886   0.988 -39.104  1.00 18.64
ATOM     12  CD2 LEU A   3      59.972   2.413 -38.377  1.00 16.69
ATOM     13  C   LEU A   3      60.913   1.324 -34.316  1.00 20.00
ATOM     14  O   LEU A   3      61.822   1.233 -33.492  1.00 19.20
ATOM     15  N   PRO A   4      59.762   0.659 -34.189  1.00 18.70
ATOM     16  CD  PRO A   4      58.468   1.039 -34.773  1.00 20.52
ATOM     17  CA  PRO A   4      59.590  -0.267 -33.073  1.00 18.57
ATOM     18  CB  PRO A   4      58.182  -0.843 -33.286  1.00 19.15
ATOM     19  CG  PRO A   4      57.626  -0.173 -34.509  1.00 20.62
ATOM     20  C   PRO A   4      60.690  -1.330 -33.153  1.00 17.90
ATOM     21  O   PRO A   4      61.194  -1.649 -34.237  1.00 16.06
ATOM     22  N   GLY A   5      61.080  -1.864 -32.001  1.00 15.62
ATOM     23  CA  GLY A   5      62.131  -2.863 -31.977  1.00 16.11
ATOM     24  C   GLY A   5      62.707  -2.979 -30.579  1.00 16.86
ATOM     25  O   GLY A   5      62.563  -4.016 -29.932  1.00 14.75
ATOM     26  N   SER A   6      63.347  -1.907 -30.116  1.00 16.83
ATOM     27  CA  SER A   6      63.944  -1.874 -28.781  1.00 18.03
ATOM     28  CB  SER A   6      65.454  -2.127 -28.869  1.00 20.18
ATOM     29  OG  SER A   6      65.748  -3.511 -28.980  1.00 25.96
ATOM     30  C   SER A   6      63.690  -0.539 -28.077  1.00 16.74
ATOM     31  O   SER A   6      64.584   0.011 -27.432  1.00 17.20
ATOM     32  N   ARG A   7      62.471  -0.031 -28.190  1.00 16.40
ATOM     33  CA  ARG A   7      62.121   1.246 -27.581  1.00 18.00
ATOM     34  CB  ARG A   7      60.847   1.801 -28.225  1.00 20.45
ATOM     35  CG  ARG A   7      60.760   1.479 -29.703  1.00 25.35
ATOM     36  CD  ARG A   7      59.863   2.400 -30.499  1.00 28.22
ATOM     37  NE  ARG A   7      58.449   2.442 -30.118  1.00 32.50
ATOM     38  CZ  ARG A   7      57.607   1.412 -30.092  1.00 31.18
ATOM     39  NH1 ARG A   7      58.002   0.202 -30.410  1.00 33.55
ATOM     40  NH2 ARG A   7      56.338   1.607 -29.780  1.00 35.54
ATOM     41  C   ARG A   7      61.922   1.134 -26.073  1.00 16.93
ATOM     42  O   ARG A   7      61.358   0.156 -25.577  1.00 14.63
ATOM     43  N   ILE A   8      62.411   2.140 -25.358  1.00 15.24
ATOM     44  CA  ILE A   8      62.272   2.205 -23.909  1.00 15.00
ATOM     45  CB  ILE A   8      63.647   2.162 -23.193  1.00 15.24
ATOM     46  CG2 ILE A   8      63.454   2.302 -21.677  1.00 14.75
ATOM     47  CG1 ILE A   8      64.382   0.857 -23.520  1.00 15.42
ATOM     48  CD1 ILE A   8      65.758   0.770 -22.881  1.00 15.28
ATOM     49  C   ILE A   8      61.613   3.548 -23.619  1.00 14.94
ATOM     50  O   ILE A   8      62.198   4.595 -23.897  1.00 14.98
ATOM     51  N   TYR A   9      60.395   3.524 -23.090  1.00 13.72
ATOM     52  CA  TYR A   9      59.690   4.758 -22.766  1.00 15.50
ATOM     53  CB  TYR A   9      58.270   4.758 -23.335  1.00 16.44
ATOM     54  CG  TYR A   9      58.205   4.849 -24.835  1.00 19.81
ATOM     55  CD1 TYR A   9      58.128   3.706 -25.619  1.00 22.16
ATOM     56  CE1 TYR A   9      58.083   3.785 -26.997  1.00 22.24
ATOM     57  CD2 TYR A   9      58.236   6.076 -25.472  1.00 22.48
ATOM     58  CE2 TYR A   9      58.193   6.165 -26.853  1.00 23.48
ATOM     59  CZ  TYR A   9      58.116   5.018 -27.608  1.00 24.02
ATOM     60  OH  TYR A   9      58.063   5.112 -28.985  1.00 24.77
ATOM     61  C   TYR A   9      59.597   4.928 -21.253  1.00 17.13
ATOM     62  O   TYR A   9      59.662   3.961 -20.498  1.00 15.23
ATOM     63  N   PRO A  10      59.464   6.172 -20.793  1.00 17.78
```

Figure 9-2

| | | | | | | | | | |
|---|---|---|---|---|---|---|---|---|---|
| ATOM | 64 | CD | PRO | A | 10 | 59.517 | 7.433 | -21.552 | 1.00 18.72 |
| ATOM | 65 | CA | PRO | A | 10 | 59.356 | 6.414 | -19.353 | 1.00 18.28 |
| ATOM | 66 | CB | PRO | A | 10 | 59.546 | 7.923 | -19.245 | 1.00 19.93 |
| ATOM | 67 | CG | PRO | A | 10 | 58.969 | 8.431 | -20.551 | 1.00 20.74 |
| ATOM | 68 | C | PRO | A | 10 | 57.975 | 5.969 | -18.874 | 1.00 18.74 |
| ATOM | 69 | O | PRO | A | 10 | 57.022 | 5.885 | -19.662 | 1.00 18.77 |
| ATOM | 70 | N | SER | A | 11 | 57.858 | 5.687 | -17.583 | 1.00 18.01 |
| ATOM | 71 | CA | SER | A | 11 | 56.581 | 5.250 | -17.029 | 1.00 18.39 |
| ATOM | 72 | CB | SER | A | 11 | 56.786 | 4.620 | -15.649 | 1.00 16.91 |
| ATOM | 73 | OG | SER | A | 11 | 57.635 | 3.495 | -15.713 | 1.00 16.53 |
| ATOM | 74 | C | SER | A | 11 | 55.583 | 6.378 | -16.877 | 1.00 19.17 |
| ATOM | 75 | O | SER | A | 11 | 55.918 | 7.446 | -16.381 | 1.00 20.59 |
| ATOM | 76 | N | PRO | A | 12 | 54.338 | 6.157 | -17.303 | 1.00 20.13 |
| ATOM | 77 | CD | PRO | A | 12 | 53.807 | 5.008 | -18.049 | 1.00 18.84 |
| ATOM | 78 | CA | PRO | A | 12 | 53.329 | 7.208 | -17.162 | 1.00 21.07 |
| ATOM | 79 | CB | PRO | A | 12 | 52.107 | 6.625 | -17.873 | 1.00 20.58 |
| ATOM | 80 | CG | PRO | A | 12 | 52.683 | 5.626 | -18.814 | 1.00 22.27 |
| ATOM | 81 | C | PRO | A | 12 | 53.058 | 7.348 | -15.662 | 1.00 22.69 |
| ATOM | 82 | O | PRO | A | 12 | 53.503 | 6.519 | -14.860 | 1.00 22.08 |
| ATOM | 83 | N | PRO | A | 13 | 52.316 | 8.391 | -15.266 | 1.00 23.84 |
| ATOM | 84 | CD | PRO | A | 13 | 51.916 | 9.566 | -16.058 | 1.00 23.70 |
| ATOM | 85 | CA | PRO | A | 13 | 52.006 | 8.583 | -13.846 | 1.00 23.94 |
| ATOM | 86 | CB | PRO | A | 13 | 51.339 | 9.957 | -13.822 | 1.00 23.46 |
| ATOM | 87 | CG | PRO | A | 13 | 51.917 | 10.650 | -15.013 | 1.00 25.44 |
| ATOM | 88 | C | PRO | A | 13 | 51.050 | 7.487 | -13.385 | 1.00 24.06 |
| ATOM | 89 | O | PRO | A | 13 | 50.210 | 7.039 | -14.161 | 1.00 24.43 |
| ATOM | 90 | N | GLN | A | 14 | 51.172 | 7.058 | -12.130 | 1.00 25.10 |
| ATOM | 91 | CA | GLN | A | 14 | 50.293 | 6.020 | -11.580 | 1.00 25.90 |
| ATOM | 92 | CB | GLN | A | 14 | 50.964 | 5.317 | -10.402 | 1.00 26.04 |
| ATOM | 93 | CG | GLN | A | 14 | 52.128 | 4.415 | -10.752 | 1.00 25.82 |
| ATOM | 94 | CD | GLN | A | 14 | 52.504 | 3.511 | -9.583 | 1.00 25.15 |
| ATOM | 95 | OE1 | GLN | A | 14 | 51.652 | 2.812 | -9.029 | 1.00 22.84 |
| ATOM | 96 | NE2 | GLN | A | 14 | 53.776 | 3.522 | -9.208 | 1.00 25.50 |
| ATOM | 97 | C | GLN | A | 14 | 48.963 | 6.575 | -11.082 | 1.00 25.97 |
| ATOM | 98 | O | GLN | A | 14 | 48.869 | 7.757 | -10.767 | 1.00 26.92 |
| ATOM | 99 | N | ALA | A | 15 | 47.941 | 5.724 | -11.003 | 1.00 26.30 |
| ATOM | 100 | CA | ALA | A | 15 | 46.642 | 6.155 | -10.488 | 1.00 27.73 |
| ATOM | 101 | CB | ALA | A | 15 | 45.588 | 5.061 | -10.683 | 1.00 28.08 |
| ATOM | 102 | C | ALA | A | 15 | 46.834 | 6.438 | -8.992 | 1.00 29.11 |
| ATOM | 103 | O | ALA | A | 15 | 47.749 | 5.903 | -8.363 | 1.00 28.24 |
| ATOM | 104 | N | PRO | A | 16 | 45.977 | 7.292 | -8.411 | 1.00 30.62 |
| ATOM | 105 | CD | PRO | A | 16 | 44.832 | 7.966 | -9.053 | 1.00 31.67 |
| ATOM | 106 | CA | PRO | A | 16 | 46.058 | 7.646 | -6.991 | 1.00 31.22 |
| ATOM | 107 | CB | PRO | A | 16 | 44.858 | 8.575 | -6.792 | 1.00 30.85 |
| ATOM | 108 | CG | PRO | A | 16 | 44.626 | 9.155 | -8.148 | 1.00 32.62 |
| ATOM | 109 | C | PRO | A | 16 | 45.961 | 6.408 | -6.099 | 1.00 32.40 |
| ATOM | 110 | O | PRO | A | 16 | 45.129 | 5.517 | -6.333 | 1.00 30.38 |
| ATOM | 111 | N | ARG | A | 17 | 46.808 | 6.368 | -5.075 | 1.00 33.85 |
| ATOM | 112 | CA | ARG | A | 17 | 46.831 | 5.262 | -4.131 | 1.00 35.41 |
| ATOM | 113 | CB | ARG | A | 17 | 47.864 | 5.538 | -3.042 | 1.00 37.82 |
| ATOM | 114 | CG | ARG | A | 17 | 48.242 | 4.314 | -2.239 | 1.00 42.80 |
| ATOM | 115 | CD | ARG | A | 17 | 48.660 | 3.148 | -3.138 | 1.00 45.70 |
| ATOM | 116 | NE | ARG | A | 17 | 49.678 | 3.526 | -4.124 | 1.00 50.72 |
| ATOM | 117 | CZ | ARG | A | 17 | 50.328 | 2.662 | -4.910 | 1.00 51.44 |
| ATOM | 118 | NH1 | ARG | A | 17 | 50.066 | 1.359 | -4.821 | 1.00 50.96 |
| ATOM | 119 | NH2 | ARG | A | 17 | 51.231 | 3.098 | -5.790 | 1.00 49.96 |
| ATOM | 120 | C | ARG | A | 17 | 45.456 | 5.029 | -3.504 | 1.00 34.71 |
| ATOM | 121 | O | ARG | A | 17 | 45.118 | 3.911 | -3.138 | 1.00 35.92 |
| ATOM | 122 | N | SER | A | 18 | 44.653 | 6.077 | -3.382 | 1.00 34.00 |
| ATOM | 123 | CA | SER | A | 18 | 43.321 | 5.923 | -2.811 | 1.00 33.31 |
| ATOM | 124 | CB | SER | A | 18 | 42.669 | 7.287 | -2.592 | 1.00 35.71 |
| ATOM | 125 | OG | SER | A | 18 | 42.099 | 7.778 | -3.804 | 1.00 37.69 |
| ATOM | 126 | C | SER | A | 18 | 42.449 | 5.115 | -3.771 | 1.00 32.05 |
| ATOM | 127 | O | SER | A | 18 | 41.526 | 4.411 | -3.355 | 1.00 31.86 |

Figure 9-3

| | | | | | | | | | |
|---|---|---|---|---|---|---|---|---|---|
| ATOM | 128 | N | LEU | A | 19 | 42.734 | 5.240 | -5.066 | 1.00 28.71 |
| ATOM | 129 | CA | LEU | A | 19 | 41.981 | 4.520 | -6.085 | 1.00 25.20 |
| ATOM | 130 | CB | LEU | A | 19 | 42.227 | 5.158 | -7.456 | 1.00 25.28 |
| ATOM | 131 | CG A | LEU | A | 19 | 41.218 | 4.817 | -8.546 | 0.50 24.96 |
| ATOM | 132 | CG B | LEU | A | 19 | 41.203 | 4.824 | -8.536 | 0.50 25.27 |
| ATOM | 133 | CD1A | LEU | A | 19 | 41.272 | 5.889 | -9.616 | 0.50 25.15 |
| ATOM | 134 | CD1B | LEU | A | 19 | 39.783 | 4.804 | -7.973 | 0.50 25.11 |
| ATOM | 135 | CD2A | LEU | A | 19 | 41.505 | 3.439 | -9.115 | 0.50 24.82 |
| ATOM | 136 | CD2B | LEU | A | 19 | 41.330 | 5.866 | -9.625 | 0.50 25.76 |
| ATOM | 137 | C | LEU | A | 19 | 42.408 | 3.052 | -6.100 | 1.00 21.70 |
| ATOM | 138 | O | LEU | A | 19 | 41.574 | 2.155 | -6.146 | 1.00 22.34 |
| ATOM | 139 | N | LEU | A | 20 | 43.711 | 2.811 | -6.056 | 1.00 19.22 |
| ATOM | 140 | CA | LEU | A | 20 | 44.216 | 1.449 | -6.051 | 1.00 18.03 |
| ATOM | 141 | CB | LEU | A | 20 | 45.746 | 1.458 | -6.138 | 1.00 18.63 |
| ATOM | 142 | CG | LEU | A | 20 | 46.355 | 2.029 | -7.435 | 1.00 20.45 |
| ATOM | 143 | CD1 | LEU | A | 20 | 47.867 | 1.973 | -7.357 | 1.00 20.60 |
| ATOM | 144 | CD2 | LEU | A | 20 | 45.870 | 1.224 | -8.638 | 1.00 18.81 |
| ATOM | 145 | C | LEU | A | 20 | 43.752 | 0.687 | -4.796 | 1.00 17.70 |
| ATOM | 146 | O | LEU | A | 20 | 43.376 | -0.482 | -4.870 | 1.00 15.31 |
| ATOM | 147 | N | ASP | A | 21 | 43.777 | 1.354 | -3.644 | 1.00 16.60 |
| ATOM | 148 | CA | ASP | A | 21 | 43.359 | 0.729 | -2.388 | 1.00 15.64 |
| ATOM | 149 | CB | ASP | A | 21 | 43.551 | 1.702 | -1.223 | 1.00 15.41 |
| ATOM | 150 | CG | ASP | A | 21 | 45.001 | 1.871 | -0.858 | 1.00 18.19 |
| ATOM | 151 | OD1 | ASP | A | 21 | 45.324 | 2.709 | 0.013 | 1.00 19.05 |
| ATOM | 152 | OD2 | ASP | A | 21 | 45.833 | 1.161 | -1.452 | 1.00 20.95 |
| ATOM | 153 | C | ASP | A | 21 | 41.916 | 0.288 | -2.445 | 1.00 13.06 |
| ATOM | 154 | O | ASP | A | 21 | 41.548 | -0.726 | -1.860 | 1.00 13.19 |
| ATOM | 155 | N | ALA | A | 22 | 41.106 | 1.055 | -3.164 | 1.00 13.80 |
| ATOM | 156 | CA | ALA | A | 22 | 39.682 | 0.763 | -3.324 | 1.00 14.30 |
| ATOM | 157 | CB | ALA | A | 22 | 38.994 | 1.915 | -4.058 | 1.00 15.12 |
| ATOM | 158 | C | ALA | A | 22 | 39.412 | -0.554 | -4.061 | 1.00 13.73 |
| ATOM | 159 | O | ALA | A | 22 | 38.349 | -1.151 | -3.899 | 1.00 14.57 |
| ATOM | 160 | N | PHE | A | 23 | 40.370 | -1.004 | -4.865 | 1.00 13.80 |
| ATOM | 161 | CA | PHE | A | 23 | 40.197 | -2.252 | -5.607 | 1.00 14.21 |
| ATOM | 162 | CB | PHE | A | 23 | 40.881 | -2.159 | -6.982 | 1.00 13.55 |
| ATOM | 163 | CG | PHE | A | 23 | 40.082 | -1.380 | -7.995 | 1.00 13.85 |
| ATOM | 164 | CD1 | PHE | A | 23 | 40.391 | -0.058 | -8.290 | 1.00 15.11 |
| ATOM | 165 | CD2 | PHE | A | 23 | 38.983 | -1.962 | -8.614 | 1.00 14.12 |
| ATOM | 166 | CE1 | PHE | A | 23 | 39.613 | 0.668 | -9.182 | 1.00 15.45 |
| ATOM | 167 | CE2 | PHE | A | 23 | 38.202 | -1.241 | -9.505 | 1.00 15.38 |
| ATOM | 168 | CZ | PHE | A | 23 | 38.519 | 0.077 | -9.787 | 1.00 15.39 |
| ATOM | 169 | C | PHE | A | 23 | 40.688 | -3.491 | -4.858 | 1.00 15.12 |
| ATOM | 170 | O | PHE | A | 23 | 40.462 | -4.627 | -5.291 | 1.00 14.35 |
| ATOM | 171 | N | GLN | A | 24 | 41.350 | -3.280 | -3.725 | 1.00 15.01 |
| ATOM | 172 | CA | GLN | A | 24 | 41.855 | -4.399 | -2.930 | 1.00 14.93 |
| ATOM | 173 | CB | GLN | A | 24 | 42.434 | -3.882 | -1.609 | 1.00 15.19 |
| ATOM | 174 | CG | GLN | A | 24 | 43.021 | -4.963 | -0.708 | 1.00 16.69 |
| ATOM | 175 | CD | GLN | A | 24 | 44.178 | -5.708 | -1.353 | 1.00 19.24 |
| ATOM | 176 | OE1 | GLN | A | 24 | 44.921 | -5.152 | -2.175 | 1.00 19.63 |
| ATOM | 177 | NE2 | GLN | A | 24 | 44.351 | -6.970 | -0.966 | 1.00 19.88 |
| ATOM | 178 | C | GLN | A | 24 | 40.757 | -5.423 | -2.637 | 1.00 14.29 |
| ATOM | 179 | O | GLN | A | 24 | 40.996 | -6.635 | -2.676 | 1.00 14.55 |
| ATOM | 180 | N | ASN | A | 25 | 39.549 | -4.946 | -2.354 | 1.00 14.51 |
| ATOM | 181 | CA | ASN | A | 25 | 38.477 | -5.870 | -2.050 | 1.00 16.50 |
| ATOM | 182 | CB | ASN | A | 25 | 37.895 | -5.496 | -0.680 | 1.00 20.86 |
| ATOM | 183 | CG | ASN | A | 25 | 38.980 | -5.537 | 0.435 | 1.00 25.73 |
| ATOM | 184 | OD1 | ASN | A | 25 | 39.622 | -6.580 | 0.658 | 1.00 27.29 |
| ATOM | 185 | ND2 | ASN | A | 25 | 39.203 | -4.401 | 1.109 | 1.00 26.01 |
| ATOM | 186 | C | ASN | A | 25 | 37.411 | -6.030 | -3.147 | 1.00 16.43 |
| ATOM | 187 | O | ASN | A | 25 | 36.277 | -6.439 | -2.882 | 1.00 16.63 |
| ATOM | 188 | N | VAL | A | 26 | 37.797 | -5.731 | -4.393 | 1.00 13.34 |
| ATOM | 189 | CA | VAL | A | 26 | 36.887 | -5.890 | -5.532 | 1.00 13.01 |
| ATOM | 190 | CB | VAL | A | 26 | 36.978 | -4.692 | -6.504 | 1.00 12.68 |
| ATOM | 191 | CG1 | VAL | A | 26 | 36.157 | -4.983 | -7.763 | 1.00 13.03 |

Figure 9-4

```
ATOM    192  CG2 VAL A  26      36.454  -3.424  -5.822  1.00 13.32
ATOM    193  C   VAL A  26      37.293  -7.170  -6.283  1.00 11.25
ATOM    194  O   VAL A  26      38.454  -7.306  -6.676  1.00 11.43
ATOM    195  N   VAL A  27      36.355  -8.104  -6.462  1.00 10.43
ATOM    196  CA  VAL A  27      36.664  -9.359  -7.163  1.00 10.76
ATOM    197  CB  VAL A  27      35.648 -10.495  -6.803  1.00 10.74
ATOM    198  CG1 VAL A  27      35.688 -10.754  -5.290  1.00 10.92
ATOM    199  CG2 VAL A  27      34.228 -10.132  -7.258  1.00  9.76
ATOM    200  C   VAL A  27      36.701  -9.136  -8.685  1.00  9.85
ATOM    201  O   VAL A  27      35.934  -8.327  -9.220  1.00 10.03
ATOM    202  N   THR A  28      37.588  -9.848  -9.378  1.00  9.40
ATOM    203  CA  THR A  28      37.711  -9.638 -10.822  1.00  9.26
ATOM    204  CB  THR A  28      38.830 -10.520 -11.445  1.00  8.98
ATOM    205  OG1 THR A  28      38.643 -11.894 -11.093  1.00  8.82
ATOM    206  CG2 THR A  28      40.192 -10.032 -10.970  1.00 10.03
ATOM    207  C   THR A  28      36.402  -9.745 -11.631  1.00 10.05
ATOM    208  O   THR A  28      36.191  -8.952 -12.550  1.00  9.97
ATOM    209  N   PRO A  29      35.504 -10.702 -11.301  1.00 10.50
ATOM    210  CD  PRO A  29      35.661 -11.888 -10.438  1.00  9.59
ATOM    211  CA  PRO A  29      34.250 -10.783 -12.075  1.00 11.10
ATOM    212  CB  PRO A  29      33.499 -11.931 -11.394  1.00 11.72
ATOM    213  CG  PRO A  29      34.606 -12.846 -10.996  1.00 11.01
ATOM    214  C   PRO A  29      33.436  -9.473 -12.051  1.00 12.22
ATOM    215  O   PRO A  29      32.746  -9.137 -13.012  1.00 11.90
ATOM    216  N   HIS A  30      33.507  -8.728 -10.952  1.00 12.14
ATOM    217  CA  HIS A  30      32.761  -7.480 -10.872  1.00 13.62
ATOM    218  CB  HIS A  30      32.515  -7.137  -9.409  1.00 15.38
ATOM    219  CG  HIS A  30      31.497  -8.039  -8.788  1.00 21.28
ATOM    220  CD2 HIS A  30      30.633  -8.915  -9.360  1.00 22.74
ATOM    221  ND1 HIS A  30      31.268  -8.102  -7.434  1.00 24.77
ATOM    222  CE1 HIS A  30      30.306  -8.978  -7.193  1.00 26.31
ATOM    223  NE2 HIS A  30      29.904  -9.484  -8.345  1.00 26.29
ATOM    224  C   HIS A  30      33.386  -6.330 -11.636  1.00 11.95
ATOM    225  O   HIS A  30      32.794  -5.258 -11.762  1.00 12.39
ATOM    226  N   ILE A  31      34.587  -6.566 -12.145  1.00 10.23
ATOM    227  CA  ILE A  31      35.267  -5.577 -12.964  1.00 11.07
ATOM    228  CB  ILE A  31      36.796  -5.603 -12.732  1.00 10.28
ATOM    229  CG2 ILE A  31      37.509  -4.728 -13.775  1.00 10.32
ATOM    230  CG1 ILE A  31      37.098  -5.096 -11.312  1.00 10.49
ATOM    231  CD1 ILE A  31      38.536  -5.319 -10.875  1.00 11.28
ATOM    232  C   ILE A  31      34.941  -5.926 -14.430  1.00 10.32
ATOM    233  O   ILE A  31      34.357  -5.116 -15.144  1.00 11.05
ATOM    234  N   SER A  32      35.264  -7.139 -14.866  1.00  9.48
ATOM    235  CA  SER A  32      34.991  -7.504 -16.257  1.00 10.09
ATOM    236  CB  SER A  32      35.630  -8.859 -16.599  1.00 11.16
ATOM    237  OG  SER A  32      35.217  -9.898 -15.725  1.00 10.55
ATOM    238  C   SER A  32      33.501  -7.493 -16.619  1.00 10.61
ATOM    239  O   SER A  32      33.144  -7.261 -17.780  1.00 10.87
ATOM    240  N   ASP A  33      32.619  -7.718 -15.647  1.00  9.69
ATOM    241  CA  ASP A  33      31.182  -7.679 -15.939  1.00 10.73
ATOM    242  CB  ASP A  33      30.342  -8.087 -14.712  1.00 11.43
ATOM    243  CG  ASP A  33      30.248  -9.600 -14.536  1.00 13.96
ATOM    244  OD1 ASP A  33      30.730 -10.342 -15.425  1.00 12.38
ATOM    245  OD2 ASP A  33      29.681 -10.050 -13.509  1.00 12.26
ATOM    246  C   ASP A  33      30.776  -6.266 -16.386  1.00 10.89
ATOM    247  O   ASP A  33      29.685  -6.070 -16.928  1.00 11.59
ATOM    248  N   ASN A  34      31.649  -5.284 -16.156  1.00 10.39
ATOM    249  CA  ASN A  34      31.362  -3.908 -16.558  1.00 11.84
ATOM    250  CB  ASN A  34      31.529  -2.967 -15.366  1.00 12.49
ATOM    251  CG  ASN A  34      30.443  -3.177 -14.335  1.00 14.04
ATOM    252  OD1 ASN A  34      29.269  -2.898 -14.591  1.00 15.09
ATOM    253  ND2 ASN A  34      30.821  -3.696 -13.170  1.00 13.73
ATOM    254  C   ASN A  34      32.229  -3.457 -17.733  1.00 12.15
ATOM    255  O   ASN A  34      32.299  -2.269 -18.051  1.00 12.03
```

Figure 9-5

```
ATOM    256  N    LEU A   35      32.874   -4.434  -18.371  1.00 11.50
ATOM    257  CA   LEU A   35      33.729   -4.199  -19.534  1.00 11.76
ATOM    258  CB   LEU A   35      35.196   -4.494  -19.192  1.00 11.64
ATOM    259  CG   LEU A   35      35.802   -3.637  -18.071  1.00 10.36
ATOM    260  CD1  LEU A   35      37.211   -4.091  -17.777  1.00 10.01
ATOM    261  CD2  LEU A   35      35.764   -2.167  -18.482  1.00 10.66
ATOM    262  C    LEU A   35      33.251   -5.135  -20.648  1.00 11.30
ATOM    263  O    LEU A   35      34.053   -5.667  -21.409  1.00 12.23
ATOM    264  N    GLY A   36      31.940   -5.340  -20.722  1.00 11.14
ATOM    265  CA   GLY A   36      31.367   -6.208  -21.742  1.00 11.04
ATOM    266  C    GLY A   36      31.646   -7.694  -21.581  1.00 11.02
ATOM    267  O    GLY A   36      31.346   -8.485  -22.486  1.00 10.61
ATOM    268  N    ARG A   37      32.193   -8.080  -20.423  1.00 10.05
ATOM    269  CA   ARG A   37      32.548   -9.476  -20.120  1.00  9.14
ATOM    270  CB   ARG A   37      31.304  -10.384  -20.127  1.00  9.30
ATOM    271  CG   ARG A   37      30.264   -9.956  -19.126  1.00 10.65
ATOM    272  CD   ARG A   37      29.086  -10.896  -18.976  1.00 10.87
ATOM    273  NE   ARG A   37      28.211  -10.307  -17.962  1.00 12.04
ATOM    274  CZ   ARG A   37      27.694  -10.958  -16.919  1.00 12.86
ATOM    275  NH1  ARG A   37      27.925  -12.258  -16.729  1.00 12.96
ATOM    276  NH2  ARG A   37      27.008  -10.274  -16.009  1.00 13.98
ATOM    277  C    ARG A   37      33.605  -10.044  -21.079  1.00 10.64
ATOM    278  O    ARG A   37      33.888  -11.243  -21.057  1.00 10.69
ATOM    279  N    HIS A   38      34.209   -9.185  -21.903  1.00 11.56
ATOM    280  CA   HIS A   38      35.202   -9.680  -22.848  1.00 10.67
ATOM    281  CB   HIS A   38      34.742   -9.390  -24.296  1.00 10.77
ATOM    282  CG   HIS A   38      34.521   -7.937  -24.606  1.00  9.75
ATOM    283  CD2  HIS A   38      33.376   -7.225  -24.747  1.00 10.11
ATOM    284  ND1  HIS A   38      35.552   -7.067  -24.881  1.00 11.33
ATOM    285  CE1  HIS A   38      35.055   -5.878  -25.184  1.00 10.12
ATOM    286  NE2  HIS A   38      33.739   -5.948  -25.110  1.00 11.18
ATOM    287  C    HIS A   38      36.645   -9.234  -22.624  1.00 11.32
ATOM    288  O    HIS A   38      37.546   -9.621  -23.383  1.00 11.15
ATOM    289  N    ILE A   39      36.882   -8.457  -21.566  1.00 10.06
ATOM    290  CA   ILE A   39      38.231   -8.001  -21.253  1.00 10.68
ATOM    291  CB   ILE A   39      38.255   -6.491  -20.934  1.00 11.97
ATOM    292  CG2  ILE A   39      39.646   -6.074  -20.461  1.00 10.48
ATOM    293  CG1  ILE A   39      37.846   -5.711  -22.200  1.00 14.14
ATOM    294  CD1  ILE A   39      37.891   -4.237  -22.069  1.00 17.99
ATOM    295  C    ILE A   39      38.801   -8.801  -20.080  1.00 11.75
ATOM    296  O    ILE A   39      38.213   -8.844  -18.998  1.00 11.59
ATOM    297  N    GLY A   40      39.929   -9.456  -20.330  1.00  9.99
ATOM    298  CA   GLY A   40      40.587  -10.272  -19.327  1.00 10.13
ATOM    299  C    GLY A   40      41.641  -11.159  -19.975  1.00 11.27
ATOM    300  O    GLY A   40      41.505  -11.533  -21.153  1.00 10.22
ATOM    301  N    ALA A   41      42.711  -11.481  -19.250  1.00 10.09
ATOM    302  CA   ALA A   41      43.729  -12.354  -19.816  1.00 10.53
ATOM    303  CB   ALA A   41      45.019  -12.294  -18.991  1.00  9.61
ATOM    304  C    ALA A   41      43.181  -13.776  -19.802  1.00 12.06
ATOM    305  O    ALA A   41      42.519  -14.177  -18.845  1.00 11.83
ATOM    306  N    ARG A   42      43.424  -14.533  -20.868  1.00 10.72
ATOM    307  CA   ARG A   42      42.990  -15.931  -20.897  1.00 10.17
ATOM    308  CB   ARG A   42      42.049  -16.211  -22.071  1.00  9.27
ATOM    309  CG   ARG A   42      40.570  -15.970  -21.805  1.00 10.16
ATOM    310  CD   ARG A   42      40.223  -14.489  -21.633  1.00  9.86
ATOM    311  NE   ARG A   42      38.798  -14.288  -21.890  1.00  9.65
ATOM    312  CZ   ARG A   42      38.244  -13.146  -22.293  1.00  8.55
ATOM    313  NH1  ARG A   42      38.992  -12.065  -22.487  1.00  8.57
ATOM    314  NH2  ARG A   42      36.939  -13.101  -22.542  1.00  9.04
ATOM    315  C    ARG A   42      44.220  -16.816  -21.041  1.00 10.84
ATOM    316  O    ARG A   42      45.109  -16.522  -21.841  1.00 10.63
ATOM    317  N    GLY A   43      44.294  -17.886  -20.254  1.00 10.62
ATOM    318  CA   GLY A   43      45.418  -18.789  -20.385  1.00 11.27
ATOM    319  C    GLY A   43      46.544  -18.749  -19.363  1.00 12.91
```

Figure 9-6

```
ATOM    320  O    GLY A  43      47.413 -19.625 -19.384  1.00 12.35
ATOM    321  N    LEU A  44      46.560 -17.746 -18.487  1.00 12.74
ATOM    322  CA   LEU A  44      47.611 -17.679 -17.471  1.00 13.42
ATOM    323  CB   LEU A  44      48.064 -16.234 -17.231  1.00 12.58
ATOM    324  CG   LEU A  44      49.061 -15.638 -18.240  1.00 15.59
ATOM    325  CD1  LEU A  44      48.471 -15.600 -19.653  1.00 15.29
ATOM    326  CD2  LEU A  44      49.420 -14.238 -17.790  1.00 15.08
ATOM    327  C    LEU A  44      47.123 -18.311 -16.168  1.00 13.75
ATOM    328  O    LEU A  44      45.929 -18.294 -15.863  1.00 15.74
ATOM    329  N    THR A  45      48.070 -18.878 -15.428  1.00 12.69
ATOM    330  CA   THR A  45      47.812 -19.544 -14.159  1.00 11.72
ATOM    331  CB   THR A  45      48.503 -20.916 -14.146  1.00 11.64
ATOM    332  OG1  THR A  45      47.856 -21.774 -15.091  1.00 13.83
ATOM    333  CG2  THR A  45      48.431 -21.555 -12.768  1.00 12.52
ATOM    334  C    THR A  45      48.347 -18.710 -12.990  1.00 11.54
ATOM    335  O    THR A  45      49.404 -18.087 -13.097  1.00 10.87
ATOM    336  N    ARG A  46      47.604 -18.688 -11.882  1.00 10.53
ATOM    337  CA   ARG A  46      48.029 -17.975 -10.687  1.00 10.03
ATOM    338  CB   ARG A  46      46.811 -17.611  -9.844  1.00 10.29
ATOM    339  CG   ARG A  46      47.117 -16.989  -8.482  1.00 11.23
ATOM    340  CD   ARG A  46      45.803 -16.621  -7.830  1.00 14.59
ATOM    341  NE   ARG A  46      45.949 -15.906  -6.573  1.00 18.42
ATOM    342  CZ   ARG A  46      45.713 -16.449  -5.382  1.00 19.48
ATOM    343  NH1  ARG A  46      45.324 -17.714  -5.293  1.00 17.94
ATOM    344  NH2  ARG A  46      45.864 -15.721  -4.282  1.00 21.33
ATOM    345  C    ARG A  46      48.915 -18.968  -9.933  1.00 10.70
ATOM    346  O    ARG A  46      48.445 -20.027  -9.500  1.00 10.74
ATOM    347  N    TYR A  47      50.193 -18.634  -9.786  1.00 10.11
ATOM    348  CA   TYR A  47      51.129 -19.520  -9.114  1.00 11.71
ATOM    349  CB   TYR A  47      52.462 -19.537  -9.866  1.00 12.82
ATOM    350  CG   TYR A  47      52.390 -20.388 -11.116  1.00 12.65
ATOM    351  CD1  TYR A  47      52.350 -21.774 -11.036  1.00 12.70
ATOM    352  CE1  TYR A  47      52.185 -22.555 -12.173  1.00 13.68
ATOM    353  CD2  TYR A  47      52.272 -19.801 -12.373  1.00 13.92
ATOM    354  CE2  TYR A  47      52.102 -20.579 -13.509  1.00 13.81
ATOM    355  CZ   TYR A  47      52.056 -21.947 -13.400  1.00 13.08
ATOM    356  OH   TYR A  47      51.836 -22.716 -14.518  1.00 15.65
ATOM    357  C    TYR A  47      51.348 -19.224  -7.628  1.00 13.58
ATOM    358  O    TYR A  47      51.920 -20.054  -6.915  1.00 14.24
ATOM    359  N    ASN A  48      50.923 -18.053  -7.163  1.00 12.49
ATOM    360  CA   ASN A  48      51.034 -17.765  -5.733  1.00 13.34
ATOM    361  CB   ASN A  48      51.027 -16.252  -5.451  1.00 11.61
ATOM    362  CG   ASN A  48      49.937 -15.506  -6.194  1.00 12.26
ATOM    363  OD1  ASN A  48      49.855 -15.570  -7.416  1.00 12.60
ATOM    364  ND2  ASN A  48      49.113 -14.770  -5.460  1.00 12.39
ATOM    365  C    ASN A  48      49.826 -18.433  -5.071  1.00 13.63
ATOM    366  O    ASN A  48      48.799 -18.637  -5.713  1.00 14.79
ATOM    367  N    HIS A  49      49.953 -18.789  -3.798  1.00 14.75
ATOM    368  CA   HIS A  49      48.859 -19.419  -3.078  1.00 17.12
ATOM    369  CB   HIS A  49      49.412 -20.467  -2.119  1.00 21.40
ATOM    370  CG   HIS A  49      49.973 -21.665  -2.820  1.00 28.23
ATOM    371  CD2  HIS A  49      49.622 -22.250  -3.991  1.00 29.84
ATOM    372  ND1  HIS A  49      51.035 -22.392  -2.330  1.00 31.83
ATOM    373  CE1  HIS A  49      51.319 -23.374  -3.171  1.00 32.22
ATOM    374  NE2  HIS A  49      50.477 -23.307  -4.185  1.00 31.83
ATOM    375  C    HIS A  49      48.015 -18.390  -2.343  1.00 16.63
ATOM    376  O    HIS A  49      46.836 -18.613  -2.116  1.00 18.17
ATOM    377  N    THR A  50      48.621 -17.265  -1.977  1.00 15.69
ATOM    378  CA   THR A  50      47.897 -16.191  -1.303  1.00 16.39
ATOM    379  CB   THR A  50      48.174 -16.159   0.225  1.00 16.87
ATOM    380  OG1  THR A  50      49.539 -15.810   0.454  1.00 19.32
ATOM    381  CG2  THR A  50      47.901 -17.507   0.850  1.00 18.07
ATOM    382  C    THR A  50      48.338 -14.856  -1.902  1.00 14.93
ATOM    383  O    THR A  50      49.349 -14.784  -2.613  1.00 14.63
```

Figure 9-7

```
ATOM    384  N    GLY A  51      47.578  -13.805   -1.612  1.00 14.32
ATOM    385  CA   GLY A  51      47.905  -12.490   -2.125  1.00 14.09
ATOM    386  C    GLY A  51      46.978  -12.030   -3.246  1.00 15.87
ATOM    387  O    GLY A  51      46.742  -12.752   -4.229  1.00 17.39
ATOM    388  N    LYS A  52      46.428  -10.832   -3.072  1.00 13.73
ATOM    389  CA   LYS A  52      45.538  -10.205   -4.043  1.00 13.46
ATOM    390  CB   LYS A  52      44.443   -9.409   -3.323  1.00 13.16
ATOM    391  CG   LYS A  52      43.621   -8.441   -4.198  1.00 13.87
ATOM    392  CD   LYS A  52      42.689   -9.170   -5.130  1.00 15.19
ATOM    393  CE   LYS A  52      41.756   -8.213   -5.876  1.00 13.30
ATOM    394  NZ   LYS A  52      40.526   -7.901   -5.101  1.00 13.75
ATOM    395  C    LYS A  52      46.434   -9.244   -4.799  1.00 13.59
ATOM    396  O    LYS A  52      47.289   -8.590   -4.206  1.00 14.05
ATOM    397  N    LEU A  53      46.246   -9.151   -6.108  1.00 13.26
ATOM    398  CA   LEU A  53      47.059   -8.255   -6.901  1.00 11.90
ATOM    399  CB   LEU A  53      47.584   -8.982   -8.145  1.00 12.95
ATOM    400  CG   LEU A  53      48.259   -8.095   -9.198  1.00 14.65
ATOM    401  CD1  LEU A  53      49.537   -7.461   -8.623  1.00 17.43
ATOM    402  CD2  LEU A  53      48.580   -8.931  -10.435  1.00 14.94
ATOM    403  C    LEU A  53      46.305   -7.005   -7.334  1.00 11.66
ATOM    404  O    LEU A  53      45.212   -7.085   -7.887  1.00 11.48
ATOM    405  N    VAL A  54      46.886   -5.848   -7.040  1.00 12.30
ATOM    406  CA   VAL A  54      46.344   -4.558   -7.469  1.00 11.83
ATOM    407  CB   VAL A  54      45.416   -3.887   -6.430  1.00 11.94
ATOM    408  CG1  VAL A  54      44.913   -2.569   -7.000  1.00 13.57
ATOM    409  CG2  VAL A  54      44.231   -4.785   -6.100  1.00 11.06
ATOM    410  C    VAL A  54      47.578   -3.678   -7.642  1.00 12.82
ATOM    411  O    VAL A  54      48.350   -3.478   -6.689  1.00 13.15
ATOM    412  N    GLY A  55      47.792   -3.172   -8.851  1.00 11.41
ATOM    413  CA   GLY A  55      48.951   -2.329   -9.088  1.00 11.44
ATOM    414  C    GLY A  55      48.868   -1.635  -10.432  1.00 11.66
ATOM    415  O    GLY A  55      47.827   -1.701  -11.097  1.00 11.73
ATOM    416  N    THR A  56      49.956   -0.981  -10.833  1.00 11.34
ATOM    417  CA   THR A  56      50.003   -0.248  -12.100  1.00 11.90
ATOM    418  CB   THR A  56      50.461    1.199  -11.858  1.00 13.60
ATOM    419  OG1  THR A  56      49.471    1.862  -11.060  1.00 15.39
ATOM    420  CG2  THR A  56      50.643    1.948  -13.171  1.00 14.44
ATOM    421  C    THR A  56      50.958   -0.934  -13.054  1.00 11.33
ATOM    422  O    THR A  56      52.090   -1.234  -12.697  1.00 11.04
ATOM    423  N    ALA A  57      50.506   -1.180  -14.279  1.00 11.61
ATOM    424  CA   ALA A  57      51.343   -1.879  -15.244  1.00 10.27
ATOM    425  CB   ALA A  57      50.501   -2.246  -16.470  1.00 10.49
ATOM    426  C    ALA A  57      52.632   -1.195  -15.706  1.00  9.96
ATOM    427  O    ALA A  57      52.607   -0.075  -16.218  1.00 10.56
ATOM    428  N    LEU A  58      53.759   -1.873  -15.504  1.00  9.36
ATOM    429  CA   LEU A  58      55.057   -1.408  -16.017  1.00 10.42
ATOM    430  CB   LEU A  58      56.163   -1.439  -14.946  1.00 11.83
ATOM    431  CG   LEU A  58      57.438   -0.655  -15.301  1.00 16.89
ATOM    432  CD1  LEU A  58      58.393   -0.626  -14.121  1.00 17.58
ATOM    433  CD2  LEU A  58      58.120   -1.278  -16.490  1.00 19.53
ATOM    434  C    LEU A  58      55.281   -2.520  -17.049  1.00 10.07
ATOM    435  O    LEU A  58      55.583   -3.658  -16.695  1.00  9.76
ATOM    436  N    THR A  59      55.120   -2.197  -18.329  1.00  9.77
ATOM    437  CA   THR A  59      55.210   -3.226  -19.362  1.00  9.17
ATOM    438  CB   THR A  59      54.190   -2.933  -20.489  1.00  9.11
ATOM    439  OG1  THR A  59      54.523   -1.679  -21.089  1.00 10.05
ATOM    440  CG2  THR A  59      52.766   -2.870  -19.952  1.00  8.18
ATOM    441  C    THR A  59      56.563   -3.480  -20.009  1.00  9.36
ATOM    442  O    THR A  59      57.410   -2.587  -20.119  1.00  9.45
ATOM    443  N    VAL A  60      56.743   -4.730  -20.444  1.00  9.69
ATOM    444  CA   VAL A  60      57.957   -5.155  -21.115  1.00  9.13
ATOM    445  CB   VAL A  60      58.943   -5.864  -20.152  1.00 10.61
ATOM    446  CG1  VAL A  60      60.206   -6.242  -20.904  1.00 10.42
ATOM    447  CG2  VAL A  60      59.270   -4.971  -18.945  1.00 10.16
```

Figure 9-8

| | | | | | | | | | |
|---|---|---|---|---|---|---|---|---|---|
| ATOM | 448 | C | VAL | A | 60 | 57.585 | -6.167 | -22.197 | 1.00 10.78 |
| ATOM | 449 | O | VAL | A | 60 | 56.826 | -7.101 | -21.939 | 1.00 10.28 |
| ATOM | 450 | N | LYS | A | 61 | 58.099 | -5.956 | -23.407 | 1.00 10.87 |
| ATOM | 451 | CA | LYS | A | 61 | 57.892 | -6.877 | -24.536 | 1.00 11.95 |
| ATOM | 452 | CB | LYS | A | 61 | 57.531 | -6.096 | -25.817 | 1.00 11.93 |
| ATOM | 453 | CG | LYS | A | 61 | 57.582 | -6.920 | -27.121 | 1.00 14.30 |
| ATOM | 454 | CD | LYS | A | 61 | 56.478 | -7.948 | -27.206 | 1.00 14.29 |
| ATOM | 455 | CE | LYS | A | 61 | 56.530 | -8.766 | -28.519 | 1.00 14.45 |
| ATOM | 456 | NZ | LYS | A | 61 | 56.218 | -7.976 | -29.738 | 1.00 13.92 |
| ATOM | 457 | C | LYS | A | 61 | 59.279 | -7.528 | -24.682 | 1.00 10.68 |
| ATOM | 458 | O | LYS | A | 61 | 60.297 | -6.843 | -24.631 | 1.00 10.93 |
| ATOM | 459 | N | THR | A | 62 | 59.345 | -8.842 | -24.851 | 1.00 9.79 |
| ATOM | 460 | CA | THR | A | 62 | 60.664 | -9.441 | -24.960 | 1.00 10.46 |
| ATOM | 461 | CB | THR | A | 62 | 61.184 | -9.849 | -23.545 | 1.00 11.48 |
| ATOM | 462 | OG1 | THR | A | 62 | 62.540 | -10.295 | -23.642 | 1.00 13.61 |
| ATOM | 463 | CG2 | THR | A | 62 | 60.328 | -10.971 | -22.946 | 1.00 11.52 |
| ATOM | 464 | C | THR | A | 62 | 60.750 | -10.656 | -25.874 | 1.00 10.61 |
| ATOM | 465 | O | THR | A | 62 | 59.742 | -11.318 | -26.135 | 1.00 9.66 |
| ATOM | 466 | N | ARG | A | 63 | 61.961 | -10.915 | -26.377 | 1.00 11.38 |
| ATOM | 467 | CA | ARG | A | 63 | 62.218 | -12.101 | -27.189 | 1.00 11.77 |
| ATOM | 468 | CB | ARG | A | 63 | 63.710 | -12.221 | -27.568 | 1.00 11.45 |
| ATOM | 469 | CG | ARG | A | 63 | 63.940 | -13.194 | -28.722 | 1.00 15.66 |
| ATOM | 470 | CD | ARG | A | 63 | 64.843 | -14.390 | -28.506 | 1.00 19.80 |
| ATOM | 471 | NE | ARG | A | 63 | 66.231 | -14.095 | -28.762 | 1.00 18.37 |
| ATOM | 472 | CZ | ARG | A | 63 | 67.137 | -14.901 | -29.331 | 1.00 12.25 |
| ATOM | 473 | NH1 | ARG | A | 63 | 66.876 | -16.129 | -29.774 | 1.00 12.46 |
| ATOM | 474 | NH2 | ARG | A | 63 | 68.369 | -14.459 | -29.409 | 1.00 11.27 |
| ATOM | 475 | C | ARG | A | 63 | 61.907 | -13.248 | -26.231 | 1.00 11.59 |
| ATOM | 476 | O | ARG | A | 63 | 62.134 | -13.120 | -25.018 | 1.00 11.84 |
| ATOM | 477 | N | PRO | A | 64 | 61.369 | -14.367 | -26.740 | 1.00 10.35 |
| ATOM | 478 | CD | PRO | A | 64 | 60.908 | -14.602 | -28.124 | 1.00 10.99 |
| ATOM | 479 | CA | PRO | A | 64 | 61.065 | -15.515 | -25.878 | 1.00 10.35 |
| ATOM | 480 | CB | PRO | A | 64 | 60.697 | -16.602 | -26.879 | 1.00 11.50 |
| ATOM | 481 | CG | PRO | A | 64 | 60.007 | -15.799 | -27.963 | 1.00 10.39 |
| ATOM | 482 | C | PRO | A | 64 | 62.294 | -15.915 | -25.040 | 1.00 10.06 |
| ATOM | 483 | O | PRO | A | 64 | 63.439 | -15.797 | -25.496 | 1.00 10.66 |
| ATOM | 484 | N | GLY | A | 65 | 62.047 | -16.373 | -23.808 | 1.00 10.93 |
| ATOM | 485 | CA | GLY | A | 65 | 63.120 | -16.813 | -22.922 | 1.00 9.56 |
| ATOM | 486 | C | GLY | A | 65 | 64.245 | -15.833 | -22.653 | 1.00 8.34 |
| ATOM | 487 | O | GLY | A | 65 | 65.349 | -16.246 | -22.321 | 1.00 9.88 |
| ATOM | 488 | N | ASP | A | 66 | 63.969 | -14.536 | -22.764 | 1.00 9.79 |
| ATOM | 489 | CA | ASP | A | 66 | 65.004 | -13.522 | -22.555 | 1.00 10.69 |
| ATOM | 490 | CB | ASP | A | 66 | 65.235 | -12.740 | -23.859 | 1.00 10.47 |
| ATOM | 491 | CG | ASP | A | 66 | 66.633 | -12.184 | -23.969 | 1.00 10.30 |
| ATOM | 492 | OD1 | ASP | A | 66 | 67.513 | -12.935 | -24.437 | 1.00 10.78 |
| ATOM | 493 | OD2 | ASP | A | 66 | 66.851 | -11.013 | -23.575 | 1.00 9.73 |
| ATOM | 494 | C | ASP | A | 66 | 64.592 | -12.532 | -21.468 | 1.00 11.06 |
| ATOM | 495 | O | ASP | A | 66 | 63.420 | -12.168 | -21.362 | 1.00 11.36 |
| ATOM | 496 | N | ASN | A | 67 | 65.550 | -12.094 | -20.657 | 1.00 11.39 |
| ATOM | 497 | CA | ASN | A | 67 | 65.212 | -11.099 | -19.652 | 1.00 11.09 |
| ATOM | 498 | CB | ASN | A | 67 | 65.061 | -11.727 | -18.253 | 1.00 11.03 |
| ATOM | 499 | CG | ASN | A | 67 | 66.346 | -12.310 | -17.705 | 1.00 12.94 |
| ATOM | 500 | OD1 | ASN | A | 67 | 67.425 | -12.196 | -18.298 | 1.00 11.72 |
| ATOM | 501 | ND2 | ASN | A | 67 | 66.235 | -12.940 | -16.534 | 1.00 12.85 |
| ATOM | 502 | C | ASN | A | 67 | 66.167 | -9.906 | -19.618 | 1.00 12.40 |
| ATOM | 503 | O | ASN | A | 67 | 66.253 | -9.204 | -18.607 | 1.00 12.03 |
| ATOM | 504 | N | LEU | A | 68 | 66.881 | -9.655 | -20.718 | 1.00 10.30 |
| ATOM | 505 | CA | LEU | A | 68 | 67.767 | -8.494 | -20.760 | 1.00 10.92 |
| ATOM | 506 | CB | LEU | A | 68 | 68.467 | -8.354 | -22.130 | 1.00 11.21 |
| ATOM | 507 | CG | LEU | A | 68 | 69.319 | -7.075 | -22.277 | 1.00 11.80 |
| ATOM | 508 | CD1 | LEU | A | 68 | 70.381 | -7.024 | -21.178 | 1.00 11.25 |
| ATOM | 509 | CD2 | LEU | A | 68 | 69.977 | -7.021 | -23.658 | 1.00 10.29 |
| ATOM | 510 | C | LEU | A | 68 | 66.943 | -7.233 | -20.494 | 1.00 10.88 |
| ATOM | 511 | O | LEU | A | 68 | 67.315 | -6.406 | -19.651 | 1.00 11.29 |

Figure 9-9

| | | | | | | | | | |
|---|---|---|---|---|---|---|---|---|---|
| ATOM | 512 | N | TYR | A | 69 | 65.819 | -7.078 | -21.194 | 1.00 9.88 |
| ATOM | 513 | CA | TYR | A | 69 | 65.009 | -5.883 | -21.001 | 1.00 10.54 |
| ATOM | 514 | CB | TYR | A | 69 | 64.116 | -5.628 | -22.222 | 1.00 11.68 |
| ATOM | 515 | CG | TYR | A | 69 | 64.909 | -4.946 | -23.314 | 1.00 11.42 |
| ATOM | 516 | CD1 | TYR | A | 69 | 64.830 | -3.569 | -23.504 | 1.00 11.82 |
| ATOM | 517 | CE1 | TYR | A | 69 | 65.669 | -2.924 | -24.407 | 1.00 13.49 |
| ATOM | 518 | CD2 | TYR | A | 69 | 65.840 | -5.661 | -24.061 | 1.00 11.10 |
| ATOM | 519 | CE2 | TYR | A | 69 | 66.683 | -5.031 | -24.955 | 1.00 11.23 |
| ATOM | 520 | CZ | TYR | A | 69 | 66.598 | -3.671 | -25.123 | 1.00 13.08 |
| ATOM | 521 | OH | TYR | A | 69 | 67.484 | -3.054 | -25.978 | 1.00 16.84 |
| ATOM | 522 | C | TYR | A | 69 | 64.221 | -5.896 | -19.702 | 1.00 11.12 |
| ATOM | 523 | O | TYR | A | 69 | 63.771 | -4.838 | -19.231 | 1.00 11.48 |
| ATOM | 524 | N | ILE | A | 70 | 64.058 | -7.085 | -19.119 | 1.00 11.14 |
| ATOM | 525 | CA | ILE | A | 70 | 63.396 | -7.178 | -17.818 | 1.00 11.24 |
| ATOM | 526 | CB | ILE | A | 70 | 63.040 | -8.646 | -17.463 | 1.00 11.27 |
| ATOM | 527 | CG2 | ILE | A | 70 | 62.591 | -8.753 | -16.009 | 1.00 12.76 |
| ATOM | 528 | CG1 | ILE | A | 70 | 61.921 | -9.129 | -18.395 | 1.00 10.49 |
| ATOM | 529 | CD1 | ILE | A | 70 | 61.673 | -10.609 | -18.347 | 1.00 12.45 |
| ATOM | 530 | C | ILE | A | 70 | 64.412 | -6.585 | -16.816 | 1.00 12.14 |
| ATOM | 531 | O | ILE | A | 70 | 64.025 | -5.807 | -15.935 | 1.00 11.34 |
| ATOM | 532 | N | TYR | A | 71 | 65.698 | -6.926 | -16.945 | 1.00 10.52 |
| ATOM | 533 | CA | TYR | A | 71 | 66.706 | -6.336 | -16.047 | 1.00 12.33 |
| ATOM | 534 | CB | TYR | A | 71 | 68.123 | -6.816 | -16.368 | 1.00 12.90 |
| ATOM | 535 | CG | TYR | A | 71 | 68.573 | -8.012 | -15.565 | 1.00 15.82 |
| ATOM | 536 | CD1 | TYR | A | 71 | 69.887 | -8.119 | -15.123 | 1.00 18.46 |
| ATOM | 537 | CE1 | TYR | A | 71 | 70.323 | -9.251 | -14.454 | 1.00 19.09 |
| ATOM | 538 | CD2 | TYR | A | 71 | 67.712 | -9.061 | -15.305 | 1.00 18.08 |
| ATOM | 539 | CE2 | TYR | A | 71 | 68.139 | -10.194 | -14.636 | 1.00 19.01 |
| ATOM | 540 | CZ | TYR | A | 71 | 69.437 | -10.283 | -14.220 | 1.00 19.70 |
| ATOM | 541 | OH | TYR | A | 71 | 69.864 | -11.425 | -13.585 | 1.00 22.49 |
| ATOM | 542 | C | TYR | A | 71 | 66.685 | -4.804 | -16.166 | 1.00 12.88 |
| ATOM | 543 | O | TYR | A | 71 | 66.730 | -4.092 | -15.162 | 1.00 12.06 |
| ATOM | 544 | N | LYS | A | 72 | 66.620 | -4.287 | -17.395 | 1.00 11.60 |
| ATOM | 545 | CA | LYS | A | 72 | 66.575 | -2.837 | -17.573 | 1.00 11.28 |
| ATOM | 546 | CB | LYS | A | 72 | 66.601 | -2.465 | -19.062 | 1.00 12.01 |
| ATOM | 547 | CG | LYS | A | 72 | 66.481 | -0.959 | -19.320 | 1.00 13.40 |
| ATOM | 548 | CD | LYS | A | 72 | 67.679 | -0.186 | -18.746 | 1.00 14.70 |
| ATOM | 549 | CE | LYS | A | 72 | 67.599 | 1.300 | -19.094 | 1.00 16.71 |
| ATOM | 550 | NZ | LYS | A | 72 | 68.827 | 2.054 | -18.690 | 1.00 16.60 |
| ATOM | 551 | C | LYS | A | 72 | 65.307 | -2.251 | -16.932 | 1.00 11.62 |
| ATOM | 552 | O | LYS | A | 72 | 65.353 | -1.187 | -16.310 | 1.00 12.14 |
| ATOM | 553 | N | ALA | A | 73 | 64.173 | -2.935 | -17.085 | 1.00 10.53 |
| ATOM | 554 | CA | ALA | A | 73 | 62.917 | -2.455 | -16.515 | 1.00 10.93 |
| ATOM | 555 | CB | ALA | A | 73 | 61.760 | -3.355 | -16.952 | 1.00 10.86 |
| ATOM | 556 | C | ALA | A | 73 | 62.981 | -2.394 | -14.982 | 1.00 11.03 |
| ATOM | 557 | O | ALA | A | 73 | 62.256 | -1.610 | -14.357 | 1.00 11.61 |
| ATOM | 558 | N | LEU | A | 74 | 63.826 | -3.233 | -14.383 | 1.00 11.32 |
| ATOM | 559 | CA | LEU | A | 74 | 63.958 | -3.244 | -12.921 | 1.00 12.17 |
| ATOM | 560 | CB | LEU | A | 74 | 65.014 | -4.273 | -12.467 | 1.00 12.17 |
| ATOM | 561 | CG | LEU | A | 74 | 64.729 | -5.763 | -12.704 | 1.00 11.03 |
| ATOM | 562 | CD1 | LEU | A | 74 | 65.902 | -6.585 | -12.227 | 1.00 12.32 |
| ATOM | 563 | CD2 | LEU | A | 74 | 63.463 | -6.184 | -11.998 | 1.00 13.34 |
| ATOM | 564 | C | LEU | A | 74 | 64.356 | -1.847 | -12.428 | 1.00 13.50 |
| ATOM | 565 | O | LEU | A | 74 | 63.962 | -1.435 | -11.332 | 1.00 13.28 |
| ATOM | 566 | N | THR | A | 75 | 65.116 | -1.118 | -13.249 | 1.00 12.64 |
| ATOM | 567 | CA | THR | A | 75 | 65.570 | 0.220 | -12.881 | 1.00 12.79 |
| ATOM | 568 | CB | THR | A | 75 | 66.791 | 0.644 | -13.728 | 1.00 13.93 |
| ATOM | 569 | OG1 | THR | A | 75 | 66.378 | 0.910 | -15.078 | 1.00 13.84 |
| ATOM | 570 | CG2 | THR | A | 75 | 67.830 | -0.471 | -13.730 | 1.00 13.57 |
| ATOM | 571 | C | THR | A | 75 | 64.491 | 1.294 | -12.991 | 1.00 13.00 |
| ATOM | 572 | O | THR | A | 75 | 64.710 | 2.437 | -12.579 | 1.00 13.82 |
| ATOM | 573 | N | LEU | A | 76 | 63.330 | 0.932 | -13.534 | 1.00 12.23 |
| ATOM | 574 | CA | LEU | A | 76 | 62.226 | 1.871 | -13.672 | 1.00 12.79 |
| ATOM | 575 | CB | LEU | A | 76 | 61.648 | 1.834 | -15.097 | 1.00 14.60 |

Figure 9-10

```
ATOM    576  CG ALEU A   76      62.385   2.464 -16.289  0.50 16.24
ATOM    577  CG BLEU A   76      62.513   2.225 -16.298  0.50 15.47
ATOM    578  CD1ALEU A   76      63.280   3.585 -15.792  0.50 16.69
ATOM    579  CD1BLEU A   76      61.611   2.361 -17.525  0.50 14.46
ATOM    580  CD2ALEU A   76      63.199   1.426 -17.033  0.50 15.38
ATOM    581  CD2BLEU A   76      63.220   3.547 -16.032  0.50 16.14
ATOM    582  C   LEU A   76      61.096   1.576 -12.678  1.00 12.05
ATOM    583  O   LEU A   76      60.144   2.335 -12.587  1.00 12.93
ATOM    584  N   ILE A   77      61.195   0.469 -11.943  1.00 12.23
ATOM    585  CA  ILE A   77      60.143   0.108 -10.993  1.00 12.34
ATOM    586  CB  ILE A   77      60.418  -1.276 -10.318  1.00 12.53
ATOM    587  CG2 ILE A   77      59.430  -1.514  -9.162  1.00 12.24
ATOM    588  CG1 ILE A   77      60.262  -2.404 -11.344  1.00 12.03
ATOM    589  CD1 ILE A   77      60.689  -3.764 -10.837  1.00 13.25
ATOM    590  C   ILE A   77      59.973   1.150  -9.887  1.00 13.17
ATOM    591  O   ILE A   77      60.960   1.605  -9.300  1.00 13.92
ATOM    592  N   GLU A   78      58.721   1.538  -9.644  1.00 13.14
ATOM    593  CA  GLU A   78      58.369   2.471  -8.579  1.00 14.48
ATOM    594  CB  GLU A   78      57.709   3.732  -9.136  1.00 17.56
ATOM    595  CG  GLU A   78      58.566   4.452 -10.151  1.00 23.83
ATOM    596  CD  GLU A   78      57.884   5.674 -10.711  1.00 28.96
ATOM    597  OE1 GLU A   78      58.123   6.000 -11.896  1.00 30.07
ATOM    598  OE2 GLU A   78      57.108   6.312  -9.963  1.00 32.85
ATOM    599  C   GLU A   78      57.365   1.718  -7.712  1.00 13.86
ATOM    600  O   GLU A   78      56.746   0.744  -8.158  1.00 13.28
ATOM    601  N   PRO A   79      57.184   2.152  -6.455  1.00 14.56
ATOM    602  CD  PRO A   79      57.916   3.184  -5.694  1.00 15.08
ATOM    603  CA  PRO A   79      56.225   1.443  -5.599  1.00 13.85
ATOM    604  CB  PRO A   79      56.233   2.274  -4.312  1.00 13.87
ATOM    605  CG  PRO A   79      57.656   2.755  -4.250  1.00 15.13
ATOM    606  C   PRO A   79      54.843   1.377  -6.237  1.00 12.36
ATOM    607  O   PRO A   79      54.341   2.377  -6.762  1.00 13.31
ATOM    608  N   GLY A   80      54.238   0.196  -6.193  1.00 11.25
ATOM    609  CA  GLY A   80      52.913   0.029  -6.754  1.00 11.16
ATOM    610  C   GLY A   80      52.913  -0.545  -8.165  1.00 10.96
ATOM    611  O   GLY A   80      51.853  -0.887  -8.685  1.00 11.78
ATOM    612  N   HIS A   81      54.088  -0.652  -8.783  1.00 11.57
ATOM    613  CA  HIS A   81      54.177  -1.210 -10.134  1.00 11.24
ATOM    614  CB  HIS A   81      55.520  -0.843 -10.781  1.00 11.76
ATOM    615  CG  HIS A   81      55.499   0.449 -11.536  1.00 13.39
ATOM    616  CD2 HIS A   81      54.510   1.059 -12.232  1.00 12.83
ATOM    617  ND1 HIS A   81      56.603   1.268 -11.635  1.00 15.04
ATOM    618  CE1 HIS A   81      56.291   2.333 -12.356  1.00 16.21
ATOM    619  NE2 HIS A   81      55.028   2.230 -12.731  1.00 13.87
ATOM    620  C   HIS A   81      54.043  -2.725 -10.151  1.00 12.02
ATOM    621  O   HIS A   81      54.484  -3.422  -9.223  1.00 11.82
ATOM    622  N   VAL A   82      53.432  -3.224 -11.222  1.00 10.69
ATOM    623  CA  VAL A   82      53.264  -4.651 -11.464  1.00 10.05
ATOM    624  CB  VAL A   82      51.794  -5.019 -11.811  1.00 10.29
ATOM    625  CG1 VAL A   82      51.702  -6.503 -12.173  1.00  9.59
ATOM    626  CG2 VAL A   82      50.862  -4.702 -10.636  1.00 11.50
ATOM    627  C   VAL A   82      54.120  -4.875 -12.713  1.00 11.20
ATOM    628  O   VAL A   82      53.962  -4.179 -13.724  1.00 11.74
ATOM    629  N   LEU A   83      55.047  -5.810 -12.651  1.00 10.25
ATOM    630  CA  LEU A   83      55.887  -6.067 -13.810  1.00 11.04
ATOM    631  CB  LEU A   83      57.150  -6.790 -13.351  1.00 12.61
ATOM    632  CG  LEU A   83      58.382  -6.817 -14.241  1.00 15.04
ATOM    633  CD1 LEU A   83      58.710  -5.423 -14.773  1.00 14.67
ATOM    634  CD2 LEU A   83      59.534  -7.370 -13.410  1.00 15.14
ATOM    635  C   LEU A   83      55.049  -6.932 -14.760  1.00 10.60
ATOM    636  O   LEU A   83      54.720  -8.067 -14.439  1.00 11.08
ATOM    637  N   VAL A   84      54.686  -6.372 -15.914  1.00  9.41
ATOM    638  CA  VAL A   84      53.846  -7.070 -16.898  1.00  9.57
ATOM    639  CB  VAL A   84      52.638  -6.186 -17.286  1.00  8.33
```

Figure 9-11

| | | | | | | | | | |
|---|---|---|---|---|---|---|---|---|---|
| ATOM | 640 | CG1 | VAL | A | 84 | 51.786 | -6.883 | -18.332 | 1.00 9.47 |
| ATOM | 641 | CG2 | VAL | A | 84 | 51.798 | -5.889 | -16.034 | 1.00 9.38 |
| ATOM | 642 | C | VAL | A | 84 | 54.706 | -7.389 | -18.122 | 1.00 10.14 |
| ATOM | 643 | O | VAL | A | 84 | 55.081 | -6.495 | -18.871 | 1.00 10.47 |
| ATOM | 644 | N | ILE | A | 85 | 54.983 | -8.677 | -18.314 | 1.00 9.76 |
| ATOM | 645 | CA | ILE | A | 85 | 55.882 | -9.132 | -19.362 | 1.00 9.37 |
| ATOM | 646 | CB | ILE | A | 85 | 57.007 | -9.956 | -18.712 | 1.00 10.53 |
| ATOM | 647 | CG2 | ILE | A | 85 | 57.995 | -10.483 | -19.794 | 1.00 9.56 |
| ATOM | 648 | CG1 | ILE | A | 85 | 57.707 | -9.101 | -17.645 | 1.00 9.61 |
| ATOM | 649 | CD1 | ILE | A | 85 | 58.505 | -9.927 | -16.670 | 1.00 9.84 |
| ATOM | 650 | C | ILE | A | 85 | 55.286 | -9.977 | -20.476 | 1.00 10.03 |
| ATOM | 651 | O | ILE | A | 85 | 54.729 | -11.038 | -20.205 | 1.00 9.60 |
| ATOM | 652 | N | ASP | A | 86 | 55.386 | -9.508 | -21.724 | 1.00 10.19 |
| ATOM | 653 | CA | ASP | A | 86 | 54.903 | -10.317 | -22.832 | 1.00 9.66 |
| ATOM | 654 | CB | ASP | A | 86 | 54.255 | -9.482 | -23.941 | 1.00 10.62 |
| ATOM | 655 | CG | ASP | A | 86 | 53.893 | -10.336 | -25.180 | 1.00 12.21 |
| ATOM | 656 | OD1 | ASP | A | 86 | 53.748 | -11.573 | -25.034 | 1.00 10.46 |
| ATOM | 657 | OD2 | ASP | A | 86 | 53.742 | -9.772 | -26.290 | 1.00 11.81 |
| ATOM | 658 | C | ASP | A | 86 | 56.125 | -11.027 | -23.393 | 1.00 9.67 |
| ATOM | 659 | O | ASP | A | 86 | 56.917 | -10.425 | -24.126 | 1.00 9.82 |
| ATOM | 660 | N | ALA | A | 87 | 56.310 | -12.289 | -23.000 | 1.00 9.46 |
| ATOM | 661 | CA | ALA | A | 87 | 57.419 | -13.094 | -23.509 | 1.00 10.33 |
| ATOM | 662 | CB | ALA | A | 87 | 58.059 | -13.926 | -22.395 | 1.00 9.08 |
| ATOM | 663 | C | ALA | A | 87 | 56.866 | -13.998 | -24.624 | 1.00 9.41 |
| ATOM | 664 | O | ALA | A | 87 | 57.417 | -15.051 | -24.940 | 1.00 10.19 |
| ATOM | 665 | N | GLN | A | 88 | 55.750 | -13.560 | -25.200 | 1.00 10.22 |
| ATOM | 666 | CA | GLN | A | 88 | 55.099 | -14.228 | -26.324 | 1.00 11.18 |
| ATOM | 667 | CB | GLN | A | 88 | 55.987 | -14.064 | -27.578 | 1.00 10.65 |
| ATOM | 668 | CG | GLN | A | 88 | 56.352 | -12.592 | -27.837 | 1.00 10.27 |
| ATOM | 669 | CD | GLN | A | 88 | 57.213 | -12.376 | -29.079 | 1.00 13.26 |
| ATOM | 670 | OE1 | GLN | A | 88 | 56.715 | -12.455 | -30.209 | 1.00 12.46 |
| ATOM | 671 | NE2 | GLN | A | 88 | 58.500 | -12.097 | -28.879 | 1.00 10.77 |
| ATOM | 672 | C | GLN | A | 88 | 54.682 | -15.684 | -26.108 | 1.00 12.32 |
| ATOM | 673 | O | GLN | A | 88 | 54.672 | -16.497 | -27.044 | 1.00 12.23 |
| ATOM | 674 | N | GLY | A | 89 | 54.331 | -16.010 | -24.865 | 1.00 11.07 |
| ATOM | 675 | CA | GLY | A | 89 | 53.853 | -17.347 | -24.544 | 1.00 12.84 |
| ATOM | 676 | C | GLY | A | 89 | 54.818 | -18.523 | -24.560 | 1.00 14.13 |
| ATOM | 677 | O | GLY | A | 89 | 54.394 | -19.669 | -24.390 | 1.00 16.12 |
| ATOM | 678 | N | ASP | A | 90 | 56.106 | -18.253 | -24.739 | 1.00 15.70 |
| ATOM | 679 | CA | ASP | A | 90 | 57.128 | -19.301 | -24.783 | 1.00 17.42 |
| ATOM | 680 | CB | ASP | A | 90 | 58.507 | -18.657 | -24.994 | 1.00 21.30 |
| ATOM | 681 | CG | ASP | A | 90 | 59.670 | -19.666 | -24.936 | 1.00 24.68 |
| ATOM | 682 | OD1 | ASP | A | 90 | 60.599 | -19.448 | -24.111 | 1.00 22.74 |
| ATOM | 683 | OD2 | ASP | A | 90 | 59.662 | -20.657 | -25.718 | 1.00 26.31 |
| ATOM | 684 | C | ASP | A | 90 | 57.131 | -20.142 | -23.513 | 1.00 16.47 |
| ATOM | 685 | O | ASP | A | 90 | 57.075 | -19.607 | -22.406 | 1.00 16.93 |
| ATOM | 686 | N | ALA | A | 91 | 57.190 | -21.460 | -23.684 | 1.00 15.30 |
| ATOM | 687 | CA | ALA | A | 91 | 57.209 | -22.392 | -22.553 | 1.00 15.79 |
| ATOM | 688 | CB | ALA | A | 91 | 56.165 | -23.488 | -22.757 | 1.00 16.60 |
| ATOM | 689 | C | ALA | A | 91 | 58.581 | -23.030 | -22.429 | 1.00 14.59 |
| ATOM | 690 | O | ALA | A | 91 | 58.813 | -23.867 | -21.568 | 1.00 16.04 |
| ATOM | 691 | N | THR | A | 92 | 59.510 | -22.620 | -23.273 | 1.00 12.62 |
| ATOM | 692 | CA | THR | A | 92 | 60.821 | -23.248 | -23.262 | 1.00 11.80 |
| ATOM | 693 | CB | THR | A | 92 | 61.420 | -23.163 | -24.685 | 1.00 12.20 |
| ATOM | 694 | OG1 | THR | A | 92 | 60.436 | -23.637 | -25.616 | 1.00 14.62 |
| ATOM | 695 | CG2 | THR | A | 92 | 62.661 | -24.026 | -24.809 | 1.00 11.44 |
| ATOM | 696 | C | THR | A | 92 | 61.831 | -22.774 | -22.205 | 1.00 11.17 |
| ATOM | 697 | O | THR | A | 92 | 62.589 | -23.593 | -21.662 | 1.00 10.70 |
| ATOM | 698 | N | ASN | A | 93 | 61.860 | -21.472 | -21.926 | 1.00 10.00 |
| ATOM | 699 | CA | ASN | A | 93 | 62.771 | -20.935 | -20.914 | 1.00 9.72 |
| ATOM | 700 | CB | ASN | A | 93 | 63.998 | -20.275 | -21.543 | 1.00 10.12 |
| ATOM | 701 | CG | ASN | A | 93 | 64.913 | -21.274 | -22.231 | 1.00 11.16 |
| ATOM | 702 | OD1 | ASN | A | 93 | 64.644 | -21.722 | -23.352 | 1.00 11.25 |
| ATOM | 703 | ND2 | ASN | A | 93 | 65.992 | -21.635 | -21.560 | 1.00 9.43 |

Figure 9-12

| | | | | | | | | | |
|---|---|---|---|---|---|---|---|---|---|
| ATOM | 704 | C | ASN | A | 93 | 62.062 | -19.889 | -20.068 | 1.00 10.26 |
| ATOM | 705 | O | ASN | A | 93 | 61.353 | -19.033 | -20.596 | 1.00 9.81 |
| ATOM | 706 | N | ALA | A | 94 | 62.268 | -19.964 | -18.752 | 1.00 9.20 |
| ATOM | 707 | CA | ALA | A | 94 | 61.684 | -19.004 | -17.811 | 1.00 9.44 |
| ATOM | 708 | CB | ALA | A | 94 | 61.957 | -19.466 | -16.358 | 1.00 8.24 |
| ATOM | 709 | C | ALA | A | 94 | 62.317 | -17.635 | -18.041 | 1.00 9.13 |
| ATOM | 710 | O | ALA | A | 94 | 63.471 | -17.557 | -18.455 | 1.00 11.31 |
| ATOM | 711 | N | VAL | A | 95 | 61.585 | -16.555 | -17.767 | 1.00 8.87 |
| ATOM | 712 | CA | VAL | A | 95 | 62.149 | -15.221 | -17.950 | 1.00 9.74 |
| ATOM | 713 | CB | VAL | A | 95 | 61.253 | -14.330 | -18.867 | 1.00 9.83 |
| ATOM | 714 | CG1 | VAL | A | 95 | 61.264 | -14.900 | -20.284 | 1.00 11.23 |
| ATOM | 715 | CG2 | VAL | A | 95 | 59.838 | -14.262 | -18.342 | 1.00 10.74 |
| ATOM | 716 | C | VAL | A | 95 | 62.416 | -14.514 | -16.611 | 1.00 10.56 |
| ATOM | 717 | O | VAL | A | 95 | 63.186 | -13.555 | -16.560 | 1.00 10.14 |
| ATOM | 718 | N | ILE | A | 96 | 61.764 | -14.961 | -15.535 | 1.00 9.84 |
| ATOM | 719 | CA | ILE | A | 96 | 62.055 | -14.382 | -14.219 | 1.00 10.45 |
| ATOM | 720 | CB | ILE | A | 96 | 61.012 | -13.360 | -13.704 | 1.00 9.74 |
| ATOM | 721 | CG2 | ILE | A | 96 | 60.885 | -12.207 | -14.675 | 1.00 9.07 |
| ATOM | 722 | CG1 | ILE | A | 96 | 59.683 | -14.045 | -13.424 | 1.00 9.11 |
| ATOM | 723 | CD1 | ILE | A | 96 | 58.632 | -13.099 | -12.843 | 1.00 10.77 |
| ATOM | 724 | C | ILE | A | 96 | 62.126 | -15.497 | -13.194 | 1.00 10.32 |
| ATOM | 725 | O | ILE | A | 96 | 61.575 | -16.584 | -13.395 | 1.00 9.71 |
| ATOM | 726 | N | GLY | A | 97 | 62.826 | -15.201 | -12.100 | 1.00 9.95 |
| ATOM | 727 | CA | GLY | A | 97 | 62.974 | -16.138 | -11.006 | 1.00 10.31 |
| ATOM | 728 | C | GLY | A | 97 | 63.021 | -15.376 | -9.694 | 1.00 9.67 |
| ATOM | 729 | O | GLY | A | 97 | 62.667 | -14.200 | -9.639 | 1.00 9.54 |
| ATOM | 730 | N | GLU | A | 98 | 63.484 | -16.051 | -8.645 | 1.00 9.99 |
| ATOM | 731 | CA | GLU | A | 98 | 63.550 | -15.468 | -7.308 | 1.00 10.26 |
| ATOM | 732 | CB | GLU | A | 98 | 64.086 | -16.510 | -6.316 | 1.00 11.61 |
| ATOM | 733 | CG | GLU | A | 98 | 64.179 | -15.992 | -4.868 | 1.00 13.92 |
| ATOM | 734 | CD | GLU | A | 98 | 64.706 | -17.042 | -3.902 | 1.00 16.74 |
| ATOM | 735 | OE1 | GLU | A | 98 | 65.658 | -17.753 | -4.275 | 1.00 17.70 |
| ATOM | 736 | OE2 | GLU | A | 98 | 64.179 | -17.145 | -2.769 | 1.00 18.01 |
| ATOM | 737 | C | GLU | A | 98 | 64.362 | -14.186 | -7.188 | 1.00 9.86 |
| ATOM | 738 | O | GLU | A | 98 | 63.919 | -13.240 | -6.541 | 1.00 9.92 |
| ATOM | 739 | N | LEU | A | 99 | 65.540 | -14.127 | -7.803 | 1.00 10.01 |
| ATOM | 740 | CA | LEU | A | 99 | 66.356 | -12.925 | -7.668 | 1.00 10.52 |
| ATOM | 741 | CB | LEU | A | 99 | 67.742 | -13.138 | -8.283 | 1.00 11.68 |
| ATOM | 742 | CG | LEU | A | 99 | 68.540 | -14.271 | -7.608 | 1.00 12.66 |
| ATOM | 743 | CD1 | LEU | A | 99 | 69.885 | -14.435 | -8.299 | 1.00 13.13 |
| ATOM | 744 | CD2 | LEU | A | 99 | 68.732 | -13.979 | -6.094 | 1.00 13.08 |
| ATOM | 745 | C | LEU | A | 99 | 65.664 | -11.693 | -8.243 | 1.00 11.23 |
| ATOM | 746 | O | LEU | A | 99 | 65.643 | -10.628 | -7.608 | 1.00 10.68 |
| ATOM | 747 | N | ILE | A | 100 | 65.077 | -11.824 | -9.433 | 1.00 10.46 |
| ATOM | 748 | CA | ILE | A | 100 | 64.360 | -10.695 | -10.003 | 1.00 10.36 |
| ATOM | 749 | CB | ILE | A | 100 | 63.866 | -11.008 | -11.440 | 1.00 11.17 |
| ATOM | 750 | CG2 | ILE | A | 100 | 62.712 | -10.093 | -11.806 | 1.00 11.15 |
| ATOM | 751 | CG1 | ILE | A | 100 | 65.040 | -10.844 | -12.417 | 1.00 12.16 |
| ATOM | 752 | CD1 | ILE | A | 100 | 64.760 | -11.372 | -13.817 | 1.00 14.33 |
| ATOM | 753 | C | ILE | A | 100 | 63.188 | -10.318 | -9.090 | 1.00 9.68 |
| ATOM | 754 | O | ILE | A | 100 | 62.927 | -9.138 | -8.876 | 1.00 10.72 |
| ATOM | 755 | N | LYS | A | 101 | 62.488 | -11.315 | -8.546 | 1.00 9.73 |
| ATOM | 756 | CA | LYS | A | 101 | 61.376 | -11.053 | -7.615 | 1.00 9.61 |
| ATOM | 757 | CB | LYS | A | 101 | 60.812 | -12.361 | -7.053 | 1.00 10.21 |
| ATOM | 758 | CG | LYS | A | 101 | 59.636 | -12.156 | -6.087 | 1.00 10.44 |
| ATOM | 759 | CD | LYS | A | 101 | 59.444 | -13.359 | -5.140 | 1.00 10.74 |
| ATOM | 760 | CE | LYS | A | 101 | 60.659 | -13.554 | -4.226 | 1.00 11.54 |
| ATOM | 761 | NZ | LYS | A | 101 | 60.332 | -14.336 | -2.983 | 1.00 9.71 |
| ATOM | 762 | C | LYS | A | 101 | 61.862 | -10.203 | -6.424 | 1.00 10.69 |
| ATOM | 763 | O | LYS | A | 101 | 61.290 | -9.149 | -6.119 | 1.00 11.16 |
| ATOM | 764 | N | LEU | A | 102 | 62.921 | -10.678 | -5.765 | 1.00 10.67 |
| ATOM | 765 | CA | LEU | A | 102 | 63.485 | -10.000 | -4.595 | 1.00 12.07 |
| ATOM | 766 | CB | LEU | A | 102 | 64.668 | -10.805 | -4.052 | 1.00 11.73 |
| ATOM | 767 | CG | LEU | A | 102 | 64.547 | -11.756 | -2.836 | 1.00 17.05 |

Figure 9-13

| | | | | | | | | |
|---|---|---|---|---|---|---|---|---|
| ATOM | 768 | CD1 | LEU | A | 102 | 63.124 | -11.952 | -2.378 | 1.00 | 15.13 |
| ATOM | 769 | CD2 | LEU | A | 102 | 65.235 | -13.064 | -3.153 | 1.00 | 12.66 |
| ATOM | 770 | C | LEU | A | 102 | 63.911 | -8.559 | -4.866 | 1.00 | 11.40 |
| ATOM | 771 | O | LEU | A | 102 | 63.573 | -7.647 | -4.094 | 1.00 | 11.71 |
| ATOM | 772 | N | TYR | A | 103 | 64.651 | -8.328 | -5.948 | 1.00 | 10.77 |
| ATOM | 773 | CA | TYR | A | 103 | 65.075 | -6.961 | -6.241 | 1.00 | 10.55 |
| ATOM | 774 | CB | TYR | A | 103 | 66.103 | -6.911 | -7.373 | 1.00 | 11.43 |
| ATOM | 775 | CG | TYR | A | 103 | 66.582 | -5.493 | -7.618 | 1.00 | 11.82 |
| ATOM | 776 | CD1 | TYR | A | 103 | 67.489 | -4.883 | -6.752 | 1.00 | 11.27 |
| ATOM | 777 | CE1 | TYR | A | 103 | 67.886 | -3.568 | -6.938 | 1.00 | 11.97 |
| ATOM | 778 | CD2 | TYR | A | 103 | 66.088 | -4.742 | -8.680 | 1.00 | 10.29 |
| ATOM | 779 | CE2 | TYR | A | 103 | 66.482 | -3.430 | -8.872 | 1.00 | 12.37 |
| ATOM | 780 | CZ | TYR | A | 103 | 67.381 | -2.846 | -8.004 | 1.00 | 12.05 |
| ATOM | 781 | OH | TYR | A | 103 | 67.788 | -1.551 | -8.220 | 1.00 | 12.76 |
| ATOM | 782 | C | TYR | A | 103 | 63.881 | -6.077 | -6.611 | 1.00 | 10.65 |
| ATOM | 783 | O | TYR | A | 103 | 63.783 | -4.922 | -6.171 | 1.00 | 10.22 |
| ATOM | 784 | N | ALA | A | 104 | 62.966 | -6.607 | -7.419 | 1.00 | 10.24 |
| ATOM | 785 | CA | ALA | A | 104 | 61.792 | -5.833 | -7.792 | 1.00 | 10.25 |
| ATOM | 786 | CB | ALA | A | 104 | 60.897 | -6.641 | -8.746 | 1.00 | 10.74 |
| ATOM | 787 | C | ALA | A | 104 | 61.021 | -5.453 | -6.522 | 1.00 | 10.57 |
| ATOM | 788 | O | ALA | A | 104 | 60.536 | -4.331 | -6.408 | 1.00 | 10.68 |
| ATOM | 789 | N | GLN | A | 105 | 60.925 | -6.376 | -5.564 | 1.00 | 10.59 |
| ATOM | 790 | CA | GLN | A | 105 | 60.201 | -6.079 | -4.327 | 1.00 | 10.80 |
| ATOM | 791 | CB | GLN | A | 105 | 59.981 | -7.362 | -3.524 | 1.00 | 10.48 |
| ATOM | 792 | CG | GLN | A | 105 | 58.957 | -8.262 | -4.194 | 1.00 | 10.52 |
| ATOM | 793 | CD | GLN | A | 105 | 58.675 | -9.561 | -3.455 | 1.00 | 11.64 |
| ATOM | 794 | OE1 | GLN | A | 105 | 59.555 | -10.144 | -2.824 | 1.00 | 12.06 |
| ATOM | 795 | NE2 | GLN | A | 105 | 57.439 | -10.034 | -3.562 | 1.00 | 12.03 |
| ATOM | 796 | C | GLN | A | 105 | 60.876 | -4.981 | -3.489 | 1.00 | 10.78 |
| ATOM | 797 | O | GLN | A | 105 | 60.180 | -4.144 | -2.918 | 1.00 | 11.86 |
| ATOM | 798 | N | GLN | A | 106 | 62.210 | -4.965 | -3.434 | 1.00 | 10.74 |
| ATOM | 799 | CA | GLN | A | 106 | 62.923 | -3.901 | -2.712 | 1.00 | 11.86 |
| ATOM | 800 | CB | GLN | A | 106 | 64.437 | -4.089 | -2.795 | 1.00 | 11.38 |
| ATOM | 801 | CG | GLN | A | 106 | 64.991 | -5.166 | -1.902 | 1.00 | 12.76 |
| ATOM | 802 | CD | GLN | A | 106 | 64.816 | -4.844 | -0.434 | 1.00 | 13.95 |
| ATOM | 803 | OE1 | GLN | A | 106 | 64.881 | -3.689 | -0.040 | 1.00 | 14.81 |
| ATOM | 804 | NE2 | GLN | A | 106 | 64.608 | -5.865 | 0.378 | 1.00 | 16.51 |
| ATOM | 805 | C | GLN | A | 106 | 62.573 | -2.538 | -3.316 | 1.00 | 12.50 |
| ATOM | 806 | O | GLN | A | 106 | 62.575 | -1.515 | -2.632 | 1.00 | 12.27 |
| ATOM | 807 | N | ARG | A | 107 | 62.279 | -2.537 | -4.615 | 1.00 | 11.90 |
| ATOM | 808 | CA | ARG | A | 107 | 61.928 | -1.315 | -5.319 | 1.00 | 12.58 |
| ATOM | 809 | CB | ARG | A | 107 | 62.377 | -1.436 | -6.777 | 1.00 | 14.25 |
| ATOM | 810 | CG | ARG | A | 107 | 63.443 | -0.445 | -7.216 | 1.00 | 21.35 |
| ATOM | 811 | CD | ARG | A | 107 | 64.797 | -0.650 | -6.592 | 1.00 | 15.71 |
| ATOM | 812 | NE | ARG | A | 107 | 64.867 | -0.167 | -5.215 | 1.00 | 15.09 |
| ATOM | 813 | CZ | ARG | A | 107 | 65.645 | -0.725 | -4.296 | 1.00 | 15.84 |
| ATOM | 814 | NH1 | ARG | A | 107 | 66.392 | -1.772 | -4.623 | 1.00 | 14.05 |
| ATOM | 815 | NH2 | ARG | A | 107 | 65.679 | -0.239 | -3.058 | 1.00 | 15.39 |
| ATOM | 816 | C | ARG | A | 107 | 60.426 | -0.982 | -5.243 | 1.00 | 11.74 |
| ATOM | 817 | O | ARG | A | 107 | 59.983 | 0.048 | -5.757 | 1.00 | 12.94 |
| ATOM | 818 | N | GLY | A | 108 | 59.641 | -1.851 | -4.605 | 1.00 | 11.06 |
| ATOM | 819 | CA | GLY | A | 108 | 58.219 | -1.586 | -4.464 | 1.00 | 10.60 |
| ATOM | 820 | C | GLY | A | 108 | 57.257 | -2.323 | -5.385 | 1.00 | 10.26 |
| ATOM | 821 | O | GLY | A | 108 | 56.059 | -2.063 | -5.359 | 1.00 | 10.33 |
| ATOM | 822 | N | CYS | A | 109 | 57.772 | -3.251 | -6.186 | 1.00 | 10.85 |
| ATOM | 823 | CA | CYS | A | 109 | 56.934 | -4.025 | -7.104 | 1.00 | 10.00 |
| ATOM | 824 | CB | CYS | A | 109 | 57.815 | -4.926 | -7.966 | 1.00 | 9.92 |
| ATOM | 825 | SG | CYS | A | 109 | 56.882 | -5.888 | -9.176 | 1.00 | 11.03 |
| ATOM | 826 | C | CYS | A | 109 | 55.946 | -4.878 | -6.317 | 1.00 | 9.92 |
| ATOM | 827 | O | CYS | A | 109 | 56.336 | -5.572 | -5.374 | 1.00 | 10.85 |
| ATOM | 828 | N | VAL | A | 110 | 54.678 | -4.852 | -6.716 | 1.00 | 9.88 |
| ATOM | 829 | CA | VAL | A | 110 | 53.636 | -5.600 | -6.009 | 1.00 | 10.38 |
| ATOM | 830 | CB | VAL | A | 110 | 52.415 | -4.687 | -5.686 | 1.00 | 11.35 |
| ATOM | 831 | CG1 | VAL | A | 110 | 52.862 | -3.495 | -4.835 | 1.00 | 11.31 |

Figure 9-14

| | | | | | | | | | |
|---|---|---|---|---|---|---|---|---|---|
| ATOM | 832 | CG2 | VAL | A | 110 | 51.753 | -4.191 | -6.974 | 1.00 12.65 |
| ATOM | 833 | C | VAL | A | 110 | 53.136 | -6.867 | -6.712 | 1.00 11.00 |
| ATOM | 834 | O | VAL | A | 110 | 52.229 | -7.553 | -6.221 | 1.00 10.95 |
| ATOM | 835 | N | GLY | A | 111 | 53.729 | -7.203 | -7.852 | 1.00 10.38 |
| ATOM | 836 | CA | GLY | A | 111 | 53.272 | -8.400 | -8.533 | 1.00 9.28 |
| ATOM | 837 | C | GLY | A | 111 | 53.948 | -8.605 | -9.869 | 1.00 9.07 |
| ATOM | 838 | O | GLY | A | 111 | 54.580 | -7.690 | -10.405 | 1.00 8.84 |
| ATOM | 839 | N | PHE | A | 112 | 53.785 | -9.814 | -10.397 | 1.00 8.86 |
| ATOM | 840 | CA | PHE | A | 112 | 54.403 | -10.217 | -11.654 | 1.00 9.63 |
| ATOM | 841 | CB | PHE | A | 112 | 55.577 | -11.148 | -11.340 | 1.00 10.13 |
| ATOM | 842 | CG | PHE | A | 112 | 56.559 | -10.550 | -10.378 | 1.00 10.85 |
| ATOM | 843 | CD1 | PHE | A | 112 | 57.695 | -9.895 | -10.841 | 1.00 11.20 |
| ATOM | 844 | CD2 | PHE | A | 112 | 56.289 | -10.549 | -9.008 | 1.00 11.34 |
| ATOM | 845 | CE1 | PHE | A | 112 | 58.541 | -9.242 | -9.967 | 1.00 10.67 |
| ATOM | 846 | CE2 | PHE | A | 112 | 57.131 | -9.896 | -8.128 | 1.00 10.02 |
| ATOM | 847 | CZ | PHE | A | 112 | 58.254 | -9.239 | -8.606 | 1.00 10.86 |
| ATOM | 848 | C | PHE | A | 112 | 53.400 | -10.924 | -12.562 | 1.00 9.97 |
| ATOM | 849 | O | PHE | A | 112 | 52.660 | -11.816 | -12.129 | 1.00 9.52 |
| ATOM | 850 | N | VAL | A | 113 | 53.381 | -10.512 | -13.827 | 1.00 9.02 |
| ATOM | 851 | CA | VAL | A | 113 | 52.488 | -11.101 | -14.812 | 1.00 9.87 |
| ATOM | 852 | CB | VAL | A | 113 | 51.388 | -10.107 | -15.218 | 1.00 10.22 |
| ATOM | 853 | CG1 | VAL | A | 113 | 50.597 | -10.661 | -16.400 | 1.00 10.53 |
| ATOM | 854 | CG2 | VAL | A | 113 | 50.452 | -9.865 | -14.030 | 1.00 10.43 |
| ATOM | 855 | C | VAL | A | 113 | 53.357 | -11.447 | -16.015 | 1.00 10.23 |
| ATOM | 856 | O | VAL | A | 113 | 54.009 | -10.571 | -16.587 | 1.00 9.79 |
| ATOM | 857 | N | VAL | A | 114 | 53.371 | -12.723 | -16.389 | 1.00 9.69 |
| ATOM | 858 | CA | VAL | A | 114 | 54.220 | -13.162 | -17.483 | 1.00 9.88 |
| ATOM | 859 | CB | VAL | A | 114 | 55.446 | -13.969 | -16.937 | 1.00 10.02 |
| ATOM | 860 | CG1 | VAL | A | 114 | 56.418 | -14.315 | -18.064 | 1.00 10.83 |
| ATOM | 861 | CG2 | VAL | A | 114 | 56.179 | -13.157 | -15.861 | 1.00 10.84 |
| ATOM | 862 | C | VAL | A | 114 | 53.504 | -14.033 | -18.505 | 1.00 9.56 |
| ATOM | 863 | O | VAL | A | 114 | 53.015 | -15.113 | -18.174 | 1.00 9.34 |
| ATOM | 864 | N | ASP | A | 115 | 53.414 | -13.554 | -19.747 | 1.00 9.22 |
| ATOM | 865 | CA | ASP | A | 115 | 52.829 | -14.407 | -20.779 | 1.00 9.68 |
| ATOM | 866 | CB | ASP | A | 115 | 52.237 | -13.597 | -21.928 | 1.00 9.88 |
| ATOM | 867 | CG | ASP | A | 115 | 51.370 | -14.455 | -22.832 | 1.00 11.22 |
| ATOM | 868 | OD1 | ASP | A | 115 | 51.612 | -15.687 | -22.869 | 1.00 13.07 |
| ATOM | 869 | OD2 | ASP | A | 115 | 50.459 | -13.911 | -23.493 | 1.00 11.27 |
| ATOM | 870 | C | ASP | A | 115 | 54.069 | -15.184 | -21.241 | 1.00 9.73 |
| ATOM | 871 | O | ASP | A | 115 | 54.760 | -14.819 | -22.206 | 1.00 9.85 |
| ATOM | 872 | N | GLY | A | 116 | 54.357 | -16.243 | -20.498 | 1.00 8.74 |
| ATOM | 873 | CA | GLY | A | 116 | 55.530 | -17.055 | -20.728 | 1.00 9.21 |
| ATOM | 874 | C | GLY | A | 116 | 55.780 | -17.840 | -19.452 | 1.00 9.68 |
| ATOM | 875 | O | GLY | A | 116 | 54.864 | -18.005 | -18.645 | 1.00 9.96 |
| ATOM | 876 | N | ALA | A | 117 | 57.015 | -18.287 | -19.256 | 1.00 9.97 |
| ATOM | 877 | CA | ALA | A | 117 | 57.358 | -19.105 | -18.098 | 1.00 9.55 |
| ATOM | 878 | CB | ALA | A | 117 | 58.124 | -20.337 | -18.581 | 1.00 9.60 |
| ATOM | 879 | C | ALA | A | 117 | 58.149 | -18.416 | -16.992 | 1.00 9.06 |
| ATOM | 880 | O | ALA | A | 117 | 58.806 | -17.402 | -17.209 | 1.00 8.68 |
| ATOM | 881 | N | ILE | A | 118 | 58.084 | -18.992 | -15.793 | 1.00 9.46 |
| ATOM | 882 | CA | ILE | A | 118 | 58.847 | -18.484 | -14.648 | 1.00 9.50 |
| ATOM | 883 | CB | ILE | A | 118 | 57.939 | -17.860 | -13.571 | 1.00 9.87 |
| ATOM | 884 | CG2 | ILE | A | 118 | 57.189 | -16.651 | -14.143 | 1.00 10.70 |
| ATOM | 885 | CG1 | ILE | A | 118 | 57.018 | -18.953 | -13.011 | 1.00 11.18 |
| ATOM | 886 | CD1 | ILE | A | 118 | 56.321 | -18.615 | -11.727 | 1.00 17.59 |
| ATOM | 887 | C | ILE | A | 118 | 59.534 | -19.676 | -13.985 | 1.00 8.74 |
| ATOM | 888 | O | ILE | A | 118 | 59.233 | -20.839 | -14.303 | 1.00 8.29 |
| ATOM | 889 | N | ARG | A | 119 | 60.482 | -19.393 | -13.084 | 1.00 9.51 |
| ATOM | 890 | CA | ARG | A | 119 | 61.137 | -20.462 | -12.314 | 1.00 9.31 |
| ATOM | 891 | CB | ARG | A | 119 | 62.508 | -20.860 | -12.907 | 1.00 9.42 |
| ATOM | 892 | CG | ARG | A | 119 | 63.640 | -19.882 | -12.750 | 1.00 9.80 |
| ATOM | 893 | CD | ARG | A | 119 | 64.898 | -20.446 | -13.439 | 1.00 10.92 |
| ATOM | 894 | NE | ARG | A | 119 | 66.112 | -19.690 | -13.130 | 1.00 11.14 |
| ATOM | 895 | CZ | ARG | A | 119 | 67.325 | -20.007 | -13.584 | 1.00 10.4 |

Figure 9-15

```
ATOM    896  NH1 ARG A 119      67.482 -21.069 -14.376  1.00  8.78
ATOM    897  NH2 ARG A 119      68.378 -19.266 -13.240  1.00 11.27
ATOM    898  C   ARG A 119      61.240 -20.028 -10.837  1.00  8.72
ATOM    899  O   ARG A 119      60.964 -18.871 -10.514  1.00  8.99
ATOM    900  N   ASP A 120      61.627 -20.968  -9.979  1.00  8.76
ATOM    901  CA  ASP A 120      61.688 -20.767  -8.517  1.00  9.47
ATOM    902  CB  ASP A 120      62.549 -19.554  -8.134  1.00  9.46
ATOM    903  CG  ASP A 120      63.956 -19.637  -8.691  1.00  9.73
ATOM    904  OD1 ASP A 120      64.556 -20.741  -8.680  1.00 12.84
ATOM    905  OD2 ASP A 120      64.477 -18.595  -9.132  1.00 11.16
ATOM    906  C   ASP A 120      60.240 -20.536  -8.062  1.00  9.60
ATOM    907  O   ASP A 120      59.947 -19.606  -7.300  1.00 10.07
ATOM    908  N   VAL A 121      59.332 -21.391  -8.523  1.00  9.05
ATOM    909  CA  VAL A 121      57.917 -21.220  -8.212  1.00  9.29
ATOM    910  CB  VAL A 121      57.051 -22.324  -8.887  1.00  8.91
ATOM    911  CG1 VAL A 121      57.409 -23.705  -8.360  1.00  9.48
ATOM    912  CG2 VAL A 121      55.589 -22.017  -8.686  1.00  9.56
ATOM    913  C   VAL A 121      57.596 -21.135  -6.715  1.00 10.25
ATOM    914  O   VAL A 121      56.746 -20.345  -6.315  1.00 11.00
ATOM    915  N   ALA A 122      58.283 -21.914  -5.886  1.00 10.09
ATOM    916  CA  ALA A 122      57.997 -21.880  -4.442  1.00 11.70
ATOM    917  CB  ALA A 122      58.835 -22.925  -3.709  1.00 11.31
ATOM    918  C   ALA A 122      58.253 -20.501  -3.844  1.00 11.05
ATOM    919  O   ALA A 122      57.613 -20.127  -2.869  1.00 11.27
ATOM    920  N   SER A 123      59.169 -19.739  -4.438  1.00 10.08
ATOM    921  CA  SER A 123      59.487 -18.412  -3.923  1.00 10.74
ATOM    922  CB  SER A 123      60.810 -17.897  -4.526  1.00 12.07
ATOM    923  OG  SER A 123      60.621 -17.313  -5.804  1.00 15.06
ATOM    924  C   SER A 123      58.362 -17.390  -4.142  1.00 11.12
ATOM    925  O   SER A 123      58.425 -16.284  -3.610  1.00 12.45
ATOM    926  N   PHE A 124      57.334 -17.753  -4.918  1.00 11.17
ATOM    927  CA  PHE A 124      56.205 -16.850  -5.167  1.00 11.01
ATOM    928  CB  PHE A 124      55.834 -16.834  -6.659  1.00 10.54
ATOM    929  CG  PHE A 124      56.877 -16.194  -7.538  1.00 10.18
ATOM    930  CD1 PHE A 124      57.877 -16.969  -8.132  1.00  9.99
ATOM    931  CD2 PHE A 124      56.867 -14.820  -7.758  1.00  9.57
ATOM    932  CE1 PHE A 124      58.845 -16.390  -8.927  1.00 10.95
ATOM    933  CE2 PHE A 124      57.832 -14.226  -8.554  1.00 10.41
ATOM    934  CZ  PHE A 124      58.825 -15.011  -9.141  1.00 10.55
ATOM    935  C   PHE A 124      54.965 -17.255  -4.359  1.00 11.86
ATOM    936  O   PHE A 124      53.856 -16.819  -4.653  1.00 11.48
ATOM    937  N   GLU A 125      55.155 -18.071  -3.327  1.00 13.34
ATOM    938  CA  GLU A 125      54.023 -18.530  -2.522  1.00 15.39
ATOM    939  CB  GLU A 125      54.507 -19.244  -1.258  1.00 19.84
ATOM    940  CG  GLU A 125      53.610 -20.426  -0.892  1.00 29.78
ATOM    941  CD  GLU A 125      52.969 -20.288   0.475  1.00 36.73
ATOM    942  OE1 GLU A 125      53.708 -20.368   1.489  1.00 40.44
ATOM    943  OE2 GLU A 125      51.725 -20.100   0.538  1.00 39.20
ATOM    944  C   GLU A 125      53.033 -17.444  -2.134  1.00 13.00
ATOM    945  O   GLU A 125      51.831 -17.653  -2.212  1.00 13.34
ATOM    946  N   ASP A 126      53.517 -16.289  -1.702  1.00 12.73
ATOM    947  CA  ASP A 126      52.581 -15.231  -1.354  1.00 15.61
ATOM    948  CB  ASP A 126      52.546 -15.016   0.165  1.00 21.06
ATOM    949  CG  ASP A 126      53.806 -14.396   0.693  1.00 27.58
ATOM    950  OD1 ASP A 126      54.884 -14.646   0.109  1.00 31.76
ATOM    951  OD2 ASP A 126      53.728 -13.658   1.708  1.00 33.68
ATOM    952  C   ASP A 126      52.877 -13.927  -2.095  1.00 14.82
ATOM    953  O   ASP A 126      52.645 -12.832  -1.576  1.00 14.12
ATOM    954  N   THR A 127      53.377 -14.064  -3.324  1.00 12.15
ATOM    955  CA  THR A 127      53.683 -12.916  -4.183  1.00 11.87
ATOM    956  CB  THR A 127      55.172 -12.889  -4.567  1.00 12.33
ATOM    957  OG1 THR A 127      55.975 -12.667  -3.398  1.00 11.54
ATOM    958  CG2 THR A 127      55.435 -11.797  -5.585  1.00 11.73
ATOM    959  C   THR A 127      52.874 -13.090  -5.472  1.00 10.90
```

Figure 9-16

```
ATOM    960  O   THR A 127      53.087 -14.061  -6.192  1.00 10.63
ATOM    961  N   PRO A 128      51.926 -12.173  -5.764  1.00 11.22
ATOM    962  CD  PRO A 128      51.466 -11.019  -4.967  1.00 12.07
ATOM    963  CA  PRO A 128      51.127 -12.304  -6.989  1.00 11.89
ATOM    964  CB  PRO A 128      50.471 -10.943  -7.106  1.00 11.71
ATOM    965  CG  PRO A 128      50.164 -10.644  -5.656  1.00 12.92
ATOM    966  C   PRO A 128      52.019 -12.653  -8.175  1.00 11.45
ATOM    967  O   PRO A 128      52.988 -11.941  -8.471  1.00 10.99
ATOM    968  N   CYS A 129      51.693 -13.760  -8.836  1.00 11.77
ATOM    969  CA  CYS A 129      52.501 -14.239  -9.945  1.00 12.03
ATOM    970  CB  CYS A 129      53.641 -15.106  -9.400  1.00 12.66
ATOM    971  SG  CYS A 129      54.771 -15.762 -10.642  1.00 17.09
ATOM    972  C   CYS A 129      51.663 -15.050 -10.916  1.00 11.57
ATOM    973  O   CYS A 129      51.262 -16.172 -10.615  1.00 12.21
ATOM    974  N   TYR A 130      51.398 -14.468 -12.085  1.00 10.73
ATOM    975  CA  TYR A 130      50.602 -15.137 -13.111  1.00  9.76
ATOM    976  CB  TYR A 130      49.476 -14.222 -13.590  1.00  9.55
ATOM    977  CG  TYR A 130      48.461 -13.939 -12.502  1.00  9.37
ATOM    978  CD1 TYR A 130      48.742 -13.032 -11.483  1.00  9.53
ATOM    979  CE1 TYR A 130      47.835 -12.799 -10.474  1.00  8.99
ATOM    980  CD2 TYR A 130      47.241 -14.607 -12.476  1.00  9.43
ATOM    981  CE2 TYR A 130      46.328 -14.386 -11.475  1.00  9.54
ATOM    982  CZ  TYR A 130      46.635 -13.475 -10.472  1.00  9.80
ATOM    983  OH  TYR A 130      45.734 -13.239  -9.463  1.00  9.87
ATOM    984  C   TYR A 130      51.520 -15.466 -14.266  1.00 10.35
ATOM    985  O   TYR A 130      52.275 -14.606 -14.717  1.00 11.26
ATOM    986  N   ALA A 131      51.483 -16.712 -14.721  1.00  9.12
ATOM    987  CA  ALA A 131      52.332 -17.126 -15.833  1.00  9.66
ATOM    988  CB  ALA A 131      53.705 -17.516 -15.325  1.00  9.98
ATOM    989  C   ALA A 131      51.699 -18.299 -16.559  1.00  9.51
ATOM    990  O   ALA A 131      50.699 -18.853 -16.112  1.00 10.32
ATOM    991  N   ARG A 132      52.282 -18.679 -17.690  1.00 10.33
ATOM    992  CA  ARG A 132      51.738 -19.796 -18.440  1.00 10.44
ATOM    993  CB  ARG A 132      52.043 -19.630 -19.939  1.00 11.59
ATOM    994  CG  ARG A 132      51.078 -18.675 -20.634  1.00 15.35
ATOM    995  CD  ARG A 132      51.170 -18.769 -22.148  1.00 19.80
ATOM    996  NE  ARG A 132      50.186 -17.917 -22.815  1.00 21.91
ATOM    997  CZ  ARG A 132      48.941 -18.293 -23.094  1.00 24.80
ATOM    998  NH1 ARG A 132      48.535 -19.514 -22.776  1.00 26.46
ATOM    999  NH2 ARG A 132      48.090 -17.443 -23.661  1.00 25.55
ATOM   1000  C   ARG A 132      52.255 -21.148 -17.948  1.00 10.35
ATOM   1001  O   ARG A 132      51.539 -22.143 -18.016  1.00 11.56
ATOM   1002  N   SER A 133      53.487 -21.178 -17.437  1.00  8.99
ATOM   1003  CA  SER A 133      54.082 -22.427 -16.976  1.00  9.76
ATOM   1004  CB  SER A 133      54.507 -23.294 -18.180  1.00  9.96
ATOM   1005  OG  SER A 133      55.638 -22.729 -18.818  1.00 11.40
ATOM   1006  C   SER A 133      55.312 -22.174 -16.110  1.00  9.32
ATOM   1007  O   SER A 133      55.795 -21.040 -16.000  1.00  9.94
ATOM   1008  N   VAL A 134      55.818 -23.251 -15.513  1.00  9.16
ATOM   1009  CA  VAL A 134      57.003 -23.192 -14.664  1.00  9.62
ATOM   1010  CB  VAL A 134      56.674 -23.653 -13.209  1.00 10.33
ATOM   1011  CG1 VAL A 134      57.968 -23.802 -12.395  1.00  9.51
ATOM   1012  CG2 VAL A 134      55.743 -22.656 -12.543  1.00 10.30
ATOM   1013  C   VAL A 134      58.046 -24.149 -15.254  1.00  9.68
ATOM   1014  O   VAL A 134      57.737 -25.304 -15.560  1.00 10.02
ATOM   1015  N   VAL A 135      59.270 -23.664 -15.427  1.00  9.50
ATOM   1016  CA  VAL A 135      60.340 -24.509 -15.939  1.00  9.88
ATOM   1017  CB  VAL A 135      60.314 -24.578 -17.499  1.00  9.66
ATOM   1018  CG1 VAL A 135      60.774 -23.269 -18.097  1.00  9.99
ATOM   1019  CG2 VAL A 135      61.166 -25.763 -17.983  1.00 11.35
ATOM   1020  C   VAL A 135      61.681 -23.964 -15.443  1.00  9.52
ATOM   1021  O   VAL A 135      61.908 -22.753 -15.462  1.00  9.92
ATOM   1022  N   HIS A 136      62.555 -24.865 -14.988  1.00  9.22
ATOM   1023  CA  HIS A 136      63.867 -24.484 -14.463  1.00  9.01
```

Figure 9-17

```
ATOM   1024  CB   HIS A 136      64.506  -25.682  -13.749  1.00   9.07
ATOM   1025  CG   HIS A 136      64.712  -26.867  -14.632  1.00   8.52
ATOM   1026  CD2  HIS A 136      63.930  -27.943  -14.871  1.00   8.69
ATOM   1027  ND1  HIS A 136      65.822  -27.005  -15.445  1.00  10.42
ATOM   1028  CE1  HIS A 136      65.709  -28.121  -16.146  1.00   9.69
ATOM   1029  NE2  HIS A 136      64.569  -28.708  -15.818  1.00  10.25
ATOM   1030  C    HIS A 136      64.827  -23.936  -15.525  1.00   9.88
ATOM   1031  O    HIS A 136      65.773  -23.200  -15.201  1.00  10.26
ATOM   1032  N    CYS A 137      64.584  -24.297  -16.786  1.00   9.96
ATOM   1033  CA   CYS A 137      65.432  -23.826  -17.880  1.00  10.90
ATOM   1034  CB   CYS A 137      64.946  -24.418  -19.201  1.00   9.80
ATOM   1035  SG   CYS A 137      65.022  -26.214  -19.176  1.00  12.27
ATOM   1036  C    CYS A 137      65.357  -22.308  -17.872  1.00   9.80
ATOM   1037  O    CYS A 137      64.307  -21.733  -18.129  1.00  10.68
ATOM   1038  N    GLY A 138      66.497  -21.687  -17.584  1.00  10.21
ATOM   1039  CA   GLY A 138      66.584  -20.250  -17.421  1.00  10.52
ATOM   1040  C    GLY A 138      66.642  -19.292  -18.586  1.00  11.77
ATOM   1041  O    GLY A 138      66.775  -19.680  -19.754  1.00  11.29
ATOM   1042  N    PRO A 139      66.567  -17.991  -18.272  1.00  10.94
ATOM   1043  CD   PRO A 139      66.396  -17.467  -16.900  1.00  10.84
ATOM   1044  CA   PRO A 139      66.595  -16.900  -19.249  1.00  10.08
ATOM   1045  CB   PRO A 139      66.027  -15.721  -18.455  1.00   9.95
ATOM   1046  CG   PRO A 139      66.621  -15.965  -17.084  1.00  10.44
ATOM   1047  C    PRO A 139      67.956  -16.571  -19.828  1.00  10.68
ATOM   1048  O    PRO A 139      69.000  -16.742  -19.181  1.00  10.37
ATOM   1049  N    TYR A 140      67.928  -16.092  -21.067  1.00  10.38
ATOM   1050  CA   TYR A 140      69.125  -15.643  -21.760  1.00  10.51
ATOM   1051  CB   TYR A 140      69.086  -16.125  -23.215  1.00  10.96
ATOM   1052  CG   TYR A 140      69.094  -17.639  -23.324  1.00   9.12
ATOM   1053  CD1  TYR A 140      70.257  -18.362  -23.088  1.00   9.86
ATOM   1054  CE1  TYR A 140      70.270  -19.751  -23.172  1.00   9.10
ATOM   1055  CD2  TYR A 140      67.936  -18.344  -23.648  1.00  10.18
ATOM   1056  CE2  TYR A 140      67.935  -19.729  -23.737  1.00   9.16
ATOM   1057  CZ   TYR A 140      69.106  -20.429  -23.499  1.00   9.50
ATOM   1058  OH   TYR A 140      69.130  -21.801  -23.596  1.00  10.41
ATOM   1059  C    TYR A 140      69.037  -14.119  -21.707  1.00  10.61
ATOM   1060  O    TYR A 140      68.027  -13.573  -21.250  1.00  10.87
ATOM   1061  N    LYS A 141      70.066  -13.409  -22.152  1.00  11.29
ATOM   1062  CA   LYS A 141      69.963  -11.958  -22.116  1.00  13.32
ATOM   1063  CB   LYS A 141      70.577  -11.373  -20.829  1.00  17.54
ATOM   1064  CG   LYS A 141      71.528  -12.263  -20.089  1.00  24.29
ATOM   1065  CD   LYS A 141      71.878  -11.655  -18.726  1.00  26.78
ATOM   1066  CE   LYS A 141      70.647  -11.507  -17.801  1.00  30.32
ATOM   1067  NZ   LYS A 141      70.069  -12.810  -17.271  1.00  30.87
ATOM   1068  C    LYS A 141      70.533  -11.275  -23.341  1.00  13.46
ATOM   1069  O    LYS A 141      71.401  -10.410  -23.254  1.00  13.63
ATOM   1070  N    SER A 142      70.002  -11.664  -24.492  1.00  11.40
ATOM   1071  CA   SER A 142      70.441  -11.098  -25.755  1.00  11.70
ATOM   1072  CB   SER A 142      70.440  -12.191  -26.829  1.00  11.05
ATOM   1073  OG   SER A 142      69.117  -12.687  -27.024  1.00  12.44
ATOM   1074  C    SER A 142      69.519   -9.980  -26.216  1.00  11.94
ATOM   1075  O    SER A 142      69.905   -9.166  -27.051  1.00  12.98
ATOM   1076  N    GLY A 143      68.311   -9.922  -25.673  1.00  10.27
ATOM   1077  CA   GLY A 143      67.360   -8.944  -26.167  1.00  11.01
ATOM   1078  C    GLY A 143      66.903   -9.540  -27.506  1.00  10.83
ATOM   1079  O    GLY A 143      67.270  -10.676  -27.822  1.00  10.90
ATOM   1080  N    PRO A 144      66.135   -8.809  -28.325  1.00  10.58
ATOM   1081  CD   PRO A 144      65.730   -9.284  -29.664  1.00  10.48
ATOM   1082  CA   PRO A 144      65.655   -7.452  -28.081  1.00  10.64
ATOM   1083  CB   PRO A 144      65.320   -6.959  -29.488  1.00  12.15
ATOM   1084  CG   PRO A 144      64.762   -8.202  -30.130  1.00  11.45
ATOM   1085  C    PRO A 144      64.439   -7.430  -27.161  1.00   9.69
ATOM   1086  O    PRO A 144      63.941   -8.475  -26.733  1.00  10.72
ATOM   1087  N    GLY A 145      63.964   -6.233  -26.856  1.00  10.15
```

Figure 9-18

```
ATOM   1088  CA   GLY A 145      62.805  -6.089 -26.001  1.00 10.02
ATOM   1089  C    GLY A 145      62.430  -4.628 -25.978  1.00 10.88
ATOM   1090  O    GLY A 145      63.198  -3.789 -26.455  1.00 12.09
ATOM   1091  N    GLU A 146      61.259  -4.315 -25.440  1.00 10.54
ATOM   1092  CA   GLU A 146      60.805  -2.927 -25.357  1.00 10.43
ATOM   1093  CB   GLU A 146      59.715  -2.624 -26.394  1.00 12.98
ATOM   1094  CG   GLU A 146      60.062  -2.996 -27.833  1.00 13.94
ATOM   1095  CD   GLU A 146      59.342  -2.119 -28.837  1.00 15.73
ATOM   1096  OE1  GLU A 146      59.976  -1.160 -29.339  1.00 16.72
ATOM   1097  OE2  GLU A 146      58.153  -2.381 -29.115  1.00 18.45
ATOM   1098  C    GLU A 146      60.220  -2.704 -23.975  1.00 11.09
ATOM   1099  O    GLU A 146      59.717  -3.645 -23.357  1.00 11.47
ATOM   1100  N    ILE A 147      60.269  -1.464 -23.510  1.00  9.46
ATOM   1101  CA   ILE A 147      59.737  -1.130 -22.193  1.00 10.42
ATOM   1102  CB   ILE A 147      60.875  -0.748 -21.227  1.00  9.74
ATOM   1103  CG2  ILE A 147      60.289  -0.338 -19.869  1.00 11.91
ATOM   1104  CG1  ILE A 147      61.835  -1.933 -21.059  1.00 11.38
ATOM   1105  CD1  ILE A 147      63.103  -1.608 -20.258  1.00 10.70
ATOM   1106  C    ILE A 147      58.724   0.018 -22.267  1.00  9.65
ATOM   1107  O    ILE A 147      58.944   1.028 -22.942  1.00  9.56
ATOM   1108  N    ASN A 148      57.616  -0.156 -21.554  1.00  9.72
ATOM   1109  CA   ASN A 148      56.536   0.813 -21.488  1.00 10.60
ATOM   1110  CB   ASN A 148      56.986   2.105 -20.785  1.00 10.98
ATOM   1111  CG   ASN A 148      57.000   1.954 -19.273  1.00 11.21
ATOM   1112  OD1  ASN A 148      56.095   1.346 -18.698  1.00 12.90
ATOM   1113  ND2  ASN A 148      58.017   2.502 -18.629  1.00 11.50
ATOM   1114  C    ASN A 148      55.862   1.119 -22.817  1.00 11.34
ATOM   1115  O    ASN A 148      55.653   2.279 -23.186  1.00 11.68
ATOM   1116  N    VAL A 149      55.533   0.038 -23.521  1.00 11.38
ATOM   1117  CA   VAL A 149      54.791   0.095 -24.772  1.00 11.44
ATOM   1118  CB   VAL A 149      55.598  -0.493 -25.970  1.00 10.80
ATOM   1119  CG1  VAL A 149      56.828   0.347 -26.237  1.00 11.12
ATOM   1120  CG2  VAL A 149      55.984  -1.938 -25.690  1.00 10.57
ATOM   1121  C    VAL A 149      53.576  -0.814 -24.522  1.00 10.92
ATOM   1122  O    VAL A 149      53.600  -1.665 -23.623  1.00 10.70
ATOM   1123  N    PRO A 150      52.479  -0.614 -25.269  1.00 10.82
ATOM   1124  CD   PRO A 150      52.148   0.488 -26.195  1.00 10.38
ATOM   1125  CA   PRO A 150      51.328  -1.490 -25.051  1.00 10.74
ATOM   1126  CB   PRO A 150      50.314  -0.984 -26.082  1.00 11.44
ATOM   1127  CG   PRO A 150      50.654   0.477 -26.188  1.00 10.08
ATOM   1128  C    PRO A 150      51.755  -2.950 -25.329  1.00 10.55
ATOM   1129  O    PRO A 150      52.530  -3.211 -26.251  1.00  9.89
ATOM   1130  N    VAL A 151      51.272  -3.894 -24.522  1.00 10.24
ATOM   1131  CA   VAL A 151      51.589  -5.307 -24.725  1.00 10.00
ATOM   1132  CB   VAL A 151      52.599  -5.856 -23.654  1.00  9.07
ATOM   1133  CG1  VAL A 151      53.927  -5.151 -23.799  1.00  9.77
ATOM   1134  CG2  VAL A 151      52.038  -5.681 -22.223  1.00  9.40
ATOM   1135  C    VAL A 151      50.312  -6.140 -24.684  1.00  9.09
ATOM   1136  O    VAL A 151      49.293  -5.710 -24.137  1.00  9.95
ATOM   1137  N    SER A 152      50.368  -7.326 -25.282  1.00  8.84
ATOM   1138  CA   SER A 152      49.235  -8.247 -25.303  1.00  9.04
ATOM   1139  CB   SER A 152      48.989  -8.755 -26.730  1.00  9.17
ATOM   1140  OG   SER A 152      47.906  -9.649 -26.756  1.00  9.56
ATOM   1141  C    SER A 152      49.587  -9.411 -24.372  1.00  9.34
ATOM   1142  O    SER A 152      50.599 -10.078 -24.565  1.00  9.56
ATOM   1143  N    ILE A 153      48.756  -9.627 -23.353  1.00  9.39
ATOM   1144  CA   ILE A 153      48.988 -10.673 -22.354  1.00  9.34
ATOM   1145  CB   ILE A 153      49.169 -10.036 -20.923  1.00  9.26
ATOM   1146  CG2  ILE A 153      49.379 -11.137 -19.871  1.00  9.27
ATOM   1147  CG1  ILE A 153      50.339  -9.042 -20.920  1.00  9.96
ATOM   1148  CD1  ILE A 153      51.712  -9.665 -21.144  1.00 10.21
ATOM   1149  C    ILE A 153      47.774 -11.596 -22.344  1.00  8.09
ATOM   1150  O    ILE A 153      46.672 -11.180 -21.980  1.00  8.78
ATOM   1151  N    GLY A 154      47.963 -12.844 -22.755  1.00  8.82
```

Figure 9-19

| | | | | | | | | | |
|---|---|---|---|---|---|---|---|---|---|
| ATOM | 1152 | CA | GLY | A | 154 | 46.837 | -13.759 | -22.802 | 1.00 9.28 |
| ATOM | 1153 | C | GLY | A | 154 | 45.701 | -13.189 | -23.637 | 1.00 8.96 |
| ATOM | 1154 | O | GLY | A | 154 | 44.526 | -13.372 | -23.311 | 1.00 9.58 |
| ATOM | 1155 | N | GLY | A | 155 | 46.053 | -12.466 | -24.703 | 1.00 8.87 |
| ATOM | 1156 | CA | GLY | A | 155 | 45.051 | -11.899 | -25.590 | 1.00 8.93 |
| ATOM | 1157 | C | GLY | A | 155 | 44.504 | -10.557 | -25.155 | 1.00 10.79 |
| ATOM | 1158 | O | GLY | A | 155 | 43.763 | -9.917 | -25.905 | 1.00 9.89 |
| ATOM | 1159 | N | MET | A | 156 | 44.870 | -10.118 | -23.948 | 1.00 9.60 |
| ATOM | 1160 | CA | MET | A | 156 | 44.396 | -8.847 | -23.415 | 1.00 9.51 |
| ATOM | 1161 | CB | MET | A | 156 | 44.051 | -8.983 | -21.928 | 1.00 8.92 |
| ATOM | 1162 | CG | MET | A | 156 | 43.613 | -7.658 | -21.299 | 1.00 8.68 |
| ATOM | 1163 | SD | MET | A | 156 | 43.008 | -7.796 | -19.585 | 1.00 10.84 |
| ATOM | 1164 | CE | MET | A | 156 | 44.531 | -8.181 | -18.711 | 1.00 9.81 |
| ATOM | 1165 | C | MET | A | 156 | 45.418 | -7.728 | -23.565 | 1.00 9.61 |
| ATOM | 1166 | O | MET | A | 156 | 46.560 | -7.845 | -23.113 | 1.00 10.16 |
| ATOM | 1167 | N | ILE | A | 157 | 45.012 | -6.629 | -24.189 | 1.00 9.46 |
| ATOM | 1168 | CA | ILE | A | 157 | 45.934 | -5.523 | -24.354 | 1.00 9.03 |
| ATOM | 1169 | CB | ILE | A | 157 | 45.448 | -4.540 | -25.449 | 1.00 10.61 |
| ATOM | 1170 | CG2 | ILE | A | 157 | 46.276 | -3.262 | -25.410 | 1.00 10.11 |
| ATOM | 1171 | CG1 | ILE | A | 157 | 45.567 | -5.217 | -26.829 | 1.00 9.43 |
| ATOM | 1172 | CD1 | ILE | A | 157 | 44.960 | -4.412 | -27.968 | 1.00 10.37 |
| ATOM | 1173 | C | ILE | A | 157 | 46.074 | -4.781 | -23.029 | 1.00 9.35 |
| ATOM | 1174 | O | ILE | A | 157 | 45.079 | -4.454 | -22.390 | 1.00 10.60 |
| ATOM | 1175 | N | ILE | A | 158 | 47.317 | -4.559 | -22.622 | 1.00 9.52 |
| ATOM | 1176 | CA | ILE | A | 158 | 47.618 | -3.828 | -21.392 | 1.00 10.21 |
| ATOM | 1177 | CB | ILE | A | 158 | 48.323 | -4.718 | -20.361 | 1.00 9.48 |
| ATOM | 1178 | CG2 | ILE | A | 158 | 48.658 | -3.889 | -19.112 | 1.00 10.10 |
| ATOM | 1179 | CG1 | ILE | A | 158 | 47.412 | -5.893 | -19.987 | 1.00 9.26 |
| ATOM | 1180 | CD1 | ILE | A | 158 | 48.049 | -6.862 | -19.045 | 1.00 10.45 |
| ATOM | 1181 | C | ILE | A | 158 | 48.533 | -2.663 | -21.738 | 1.00 10.06 |
| ATOM | 1182 | O | ILE | A | 158 | 49.611 | -2.854 | -22.302 | 1.00 10.38 |
| ATOM | 1183 | N | ASN | A | 159 | 48.087 | -1.453 | -21.409 | 1.00 10.12 |
| ATOM | 1184 | CA | ASN | A | 159 | 48.863 | -0.248 | -21.670 | 1.00 10.53 |
| ATOM | 1185 | CB | ASN | A | 159 | 47.932 | 0.903 | -22.063 | 1.00 11.18 |
| ATOM | 1186 | CG | ASN | A | 159 | 47.217 | 0.654 | -23.375 | 1.00 13.56 |
| ATOM | 1187 | OD1 | ASN | A | 159 | 47.848 | 0.304 | -24.373 | 1.00 15.26 |
| ATOM | 1188 | ND2 | ASN | A | 159 | 45.904 | 0.842 | -23.386 | 1.00 14.31 |
| ATOM | 1189 | C | ASN | A | 159 | 49.674 | 0.187 | -20.441 | 1.00 11.93 |
| ATOM | 1190 | O | ASN | A | 159 | 49.261 | -0.055 | -19.293 | 1.00 11.49 |
| ATOM | 1191 | N | PRO | A | 160 | 50.836 | 0.829 | -20.663 | 1.00 11.62 |
| ATOM | 1192 | CD | PRO | A | 160 | 51.493 | 1.153 | -21.943 | 1.00 11.36 |
| ATOM | 1193 | CA | PRO | A | 160 | 51.643 | 1.282 | -19.525 | 1.00 12.16 |
| ATOM | 1194 | CB | PRO | A | 160 | 52.758 | 2.080 | -20.190 | 1.00 12.36 |
| ATOM | 1195 | CG | PRO | A | 160 | 52.914 | 1.405 | -21.527 | 1.00 12.57 |
| ATOM | 1196 | C | PRO | A | 160 | 50.763 | 2.177 | -18.640 | 1.00 12.40 |
| ATOM | 1197 | O | PRO | A | 160 | 50.031 | 3.036 | -19.142 | 1.00 12.95 |
| ATOM | 1198 | N | GLY | A | 161 | 50.815 | 1.969 | -17.328 | 1.00 12.44 |
| ATOM | 1199 | CA | GLY | A | 161 | 50.011 | 2.788 | -16.439 | 1.00 11.78 |
| ATOM | 1200 | C | GLY | A | 161 | 48.641 | 2.225 | -16.129 | 1.00 12.09 |
| ATOM | 1201 | O | GLY | A | 161 | 47.950 | 2.737 | -15.243 | 1.00 13.47 |
| ATOM | 1202 | N | ASP | A | 162 | 48.211 | 1.187 | -16.843 | 1.00 11.25 |
| ATOM | 1203 | CA | ASP | A | 162 | 46.895 | 0.612 | -16.564 | 1.00 10.24 |
| ATOM | 1204 | CB | ASP | A | 162 | 46.555 | -0.518 | -17.534 | 1.00 11.68 |
| ATOM | 1205 | CG | ASP | A | 162 | 45.968 | -0.024 | -18.828 | 1.00 14.04 |
| ATOM | 1206 | OD1 | ASP | A | 162 | 45.683 | 1.187 | -18.932 | 1.00 14.66 |
| ATOM | 1207 | OD2 | ASP | A | 162 | 45.783 | -0.872 | -19.738 | 1.00 14.72 |
| ATOM | 1208 | C | ASP | A | 162 | 46.832 | 0.012 | -15.165 | 1.00 10.71 |
| ATOM | 1209 | O | ASP | A | 162 | 47.840 | -0.460 | -14.637 | 1.00 11.03 |
| ATOM | 1210 | N | ILE | A | 163 | 45.638 | 0.010 | -14.585 | 1.00 11.43 |
| ATOM | 1211 | CA | ILE | A | 163 | 45.449 | -0.608 | -13.284 | 1.00 12.02 |
| ATOM | 1212 | CB | ILE | A | 163 | 44.183 | -0.069 | -12.569 | 1.00 12.72 |
| ATOM | 1213 | CG2 | ILE | A | 163 | 43.933 | -0.855 | -11.271 | 1.00 11.38 |
| ATOM | 1214 | CG1 | ILE | A | 163 | 44.360 | 1.432 | -12.305 | 1.00 14.60 |
| ATOM | 1215 | CD1 | ILE | A | 163 | 43.114 | 2.127 | -11.806 | 1.00 20.19 |

Figure 9-20

| ATOM | 1216 | C | ILE | A | 163 | 45.278 | -2.091 | -13.583 | 1.00 | 11.33 |
| ATOM | 1217 | O | ILE | A | 163 | 44.529 | -2.458 | -14.483 | 1.00 | 11.10 |
| ATOM | 1218 | N | ILE | A | 164 | 45.995 | -2.927 | -12.836 | 1.00 | 11.16 |
| ATOM | 1219 | CA | ILE | A | 164 | 45.944 | -4.381 | -12.973 | 1.00 | 11.64 |
| ATOM | 1220 | CB | ILE | A | 164 | 47.357 | -4.992 | -13.125 | 1.00 | 13.23 |
| ATOM | 1221 | CG2 | ILE | A | 164 | 47.252 | -6.491 | -13.283 | 1.00 | 14.37 |
| ATOM | 1222 | CG1 | ILE | A | 164 | 48.075 | -4.371 | -14.312 | 1.00 | 15.60 |
| ATOM | 1223 | CD1 | ILE | A | 164 | 47.280 | -4.484 | -15.594 | 1.00 | 16.74 |
| ATOM | 1224 | C | ILE | A | 164 | 45.359 | -4.971 | -11.696 | 1.00 | 11.84 |
| ATOM | 1225 | O | ILE | A | 164 | 45.831 | -4.656 | -10.594 | 1.00 | 11.90 |
| ATOM | 1226 | N | VAL | A | 165 | 44.341 | -5.809 | -11.828 | 1.00 | 9.34 |
| ATOM | 1227 | CA | VAL | A | 165 | 43.755 | -6.448 | -10.649 | 1.00 | 10.38 |
| ATOM | 1228 | CB | VAL | A | 165 | 42.311 | -5.957 | -10.373 | 1.00 | 10.37 |
| ATOM | 1229 | CG1 | VAL | A | 165 | 41.725 | -6.674 | -9.159 | 1.00 | 10.66 |
| ATOM | 1230 | CG2 | VAL | A | 165 | 42.320 | -4.467 | -10.142 | 1.00 | 10.08 |
| ATOM | 1231 | C | VAL | A | 165 | 43.752 | -7.942 | -10.927 | 1.00 | 11.00 |
| ATOM | 1232 | O | VAL | A | 165 | 43.336 | -8.383 | -12.008 | 1.00 | 10.95 |
| ATOM | 1233 | N | GLY | A | 166 | 44.253 | -8.718 | -9.973 | 1.00 | 9.90 |
| ATOM | 1234 | CA | GLY | A | 166 | 44.295 | -10.153 | -10.147 | 1.00 | 9.79 |
| ATOM | 1235 | C | GLY | A | 166 | 43.958 | -10.919 | -8.883 | 1.00 | 11.78 |
| ATOM | 1236 | O | GLY | A | 166 | 44.418 | -10.577 | -7.783 | 1.00 | 11.75 |
| ATOM | 1237 | N | ASP | A | 167 | 43.120 | -11.933 | -9.024 | 1.00 | 9.88 |
| ATOM | 1238 | CA | ASP | A | 167 | 42.793 | -12.774 | -7.888 | 1.00 | 10.36 |
| ATOM | 1239 | CB | ASP | A | 167 | 41.494 | -12.317 | -7.190 | 1.00 | 10.19 |
| ATOM | 1240 | CG | ASP | A | 167 | 40.274 | -12.336 | -8.091 | 1.00 | 10.95 |
| ATOM | 1241 | OD1 | ASP | A | 167 | 40.305 | -13.020 | -9.133 | 1.00 | 11.44 |
| ATOM | 1242 | OD2 | ASP | A | 167 | 39.267 | -11.678 | -7.734 | 1.00 | 10.43 |
| ATOM | 1243 | C | ASP | A | 167 | 42.760 | -14.231 | -8.359 | 1.00 | 10.86 |
| ATOM | 1244 | O | ASP | A | 167 | 43.326 | -14.540 | -9.407 | 1.00 | 10.63 |
| ATOM | 1245 | N | GLU | A | 168 | 42.127 | -15.133 | -7.620 | 1.00 | 10.29 |
| ATOM | 1246 | CA | GLU | A | 168 | 42.143 | -16.535 | -8.021 | 1.00 | 11.10 |
| ATOM | 1247 | CB | GLU | A | 168 | 41.636 | -17.437 | -6.876 | 1.00 | 12.88 |
| ATOM | 1248 | CG | GLU | A | 168 | 40.189 | -17.223 | -6.497 | 1.00 | 15.00 |
| ATOM | 1249 | CD | GLU | A | 168 | 39.968 | -16.131 | -5.423 | 1.00 | 18.95 |
| ATOM | 1250 | OE1 | GLU | A | 168 | 40.844 | -15.246 | -5.229 | 1.00 | 16.65 |
| ATOM | 1251 | OE2 | GLU | A | 168 | 38.891 | -16.160 | -4.783 | 1.00 | 19.23 |
| ATOM | 1252 | C | GLU | A | 168 | 41.361 | -16.817 | -9.301 | 1.00 | 10.58 |
| ATOM | 1253 | O | GLU | A | 168 | 41.518 | -17.879 | -9.908 | 1.00 | 11.66 |
| ATOM | 1254 | N | ASP | A | 169 | 40.530 | -15.868 | -9.712 | 1.00 | 10.26 |
| ATOM | 1255 | CA | ASP | A | 169 | 39.747 | -16.041 | -10.937 | 1.00 | 10.62 |
| ATOM | 1256 | CB | ASP | A | 169 | 38.322 | -15.522 | -10.722 | 1.00 | 11.37 |
| ATOM | 1257 | CG | ASP | A | 169 | 37.547 | -16.397 | -9.752 | 1.00 | 13.68 |
| ATOM | 1258 | OD1 | ASP | A | 169 | 37.217 | -17.545 | -10.132 | 1.00 | 13.12 |
| ATOM | 1259 | OD2 | ASP | A | 169 | 37.295 | -15.955 | -8.606 | 1.00 | 13.85 |
| ATOM | 1260 | C | ASP | A | 169 | 40.401 | -15.388 | -12.163 | 1.00 | 10.47 |
| ATOM | 1261 | O | ASP | A | 169 | 39.813 | -15.361 | -13.239 | 1.00 | 10.23 |
| ATOM | 1262 | N | GLY | A | 170 | 41.611 | -14.864 | -12.009 | 1.00 | 9.45 |
| ATOM | 1263 | CA | GLY | A | 170 | 42.288 | -14.273 | -13.147 | 1.00 | 9.20 |
| ATOM | 1264 | C | GLY | A | 170 | 42.773 | -12.844 | -13.039 | 1.00 | 11.56 |
| ATOM | 1265 | O | GLY | A | 170 | 42.864 | -12.275 | -11.948 | 1.00 | 10.10 |
| ATOM | 1266 | N | LEU | A | 171 | 43.066 | -12.273 | -14.207 | 1.00 | 10.49 |
| ATOM | 1267 | CA | LEU | A | 171 | 43.616 | -10.928 | -14.380 | 1.00 | 11.18 |
| ATOM | 1268 | CB | LEU | A | 171 | 44.961 | -11.025 | -15.060 | 1.00 | 14.04 |
| ATOM | 1269 | CG | LEU | A | 171 | 46.145 | -11.574 | -14.317 | 1.00 | 17.71 |
| ATOM | 1270 | CD1 | LEU | A | 171 | 47.214 | -11.920 | -15.346 | 1.00 | 18.78 |
| ATOM | 1271 | CD2 | LEU | A | 171 | 46.633 | -10.516 | -13.309 | 1.00 | 15.72 |
| ATOM | 1272 | C | LEU | A | 171 | 42.781 | -10.060 | -15.296 | 1.00 | 11.20 |
| ATOM | 1273 | O | LEU | A | 171 | 42.328 | -10.513 | -16.349 | 1.00 | 11.72 |
| ATOM | 1274 | N | VAL | A | 172 | 42.651 | -8.796 | -14.918 | 1.00 | 10.19 |
| ATOM | 1275 | CA | VAL | A | 172 | 41.934 | -7.835 | -15.724 | 1.00 | 10.00 |
| ATOM | 1276 | CB | VAL | A | 172 | 40.458 | -7.663 | -15.251 | 1.00 | 10.61 |
| ATOM | 1277 | CG1 | VAL | A | 172 | 40.414 | -6.986 | -13.887 | 1.00 | 9.43 |
| ATOM | 1278 | CG2 | VAL | A | 172 | 39.672 | -6.864 | -16.272 | 1.00 | 9.95 |
| ATOM | 1279 | C | VAL | A | 172 | 42.716 | -6.527 | -15.623 | 1.00 | 12.03 |

Figure 9-21

| | | | | | | | | | |
|---|---|---|---|---|---|---|---|---|---|
| ATOM | 1280 | O | VAL | A | 172 | 43.445 | -6.303 | -14.649 | 1.00 11.71 |
| ATOM | 1281 | N | ALA | A | 173 | 42.619 | -5.692 | -16.655 | 1.00 10.60 |
| ATOM | 1282 | CA | ALA | A | 173 | 43.318 | -4.411 | -16.681 | 1.00 10.23 |
| ATOM | 1283 | CB | ALA | A | 173 | 44.577 | -4.496 | -17.571 | 1.00 10.87 |
| ATOM | 1284 | C | ALA | A | 173 | 42.387 | -3.347 | -17.224 | 1.00 11.16 |
| ATOM | 1285 | O | ALA | A | 173 | 41.511 | -3.639 | -18.038 | 1.00 11.62 |
| ATOM | 1286 | N | PHE | A | 174 | 42.560 | -2.115 | -16.763 | 1.00 11.15 |
| ATOM | 1287 | CA | PHE | A | 174 | 41.750 | -0.998 | -17.243 | 1.00 11.58 |
| ATOM | 1288 | CB | PHE | A | 174 | 40.353 | -0.977 | -16.597 | 1.00 11.84 |
| ATOM | 1289 | CG | PHE | A | 174 | 40.367 | -1.108 | -15.105 | 1.00 12.70 |
| ATOM | 1290 | CD1 | PHE | A | 174 | 40.423 | -2.358 | -14.506 | 1.00 13.16 |
| ATOM | 1291 | CD2 | PHE | A | 174 | 40.371 | 0.023 | -14.298 | 1.00 13.02 |
| ATOM | 1292 | CE1 | PHE | A | 174 | 40.484 | -2.483 | -13.124 | 1.00 14.31 |
| ATOM | 1293 | CE2 | PHE | A | 174 | 40.431 | -0.096 | -12.902 | 1.00 13.51 |
| ATOM | 1294 | CZ | PHE | A | 174 | 40.490 | -1.348 | -12.320 | 1.00 12.74 |
| ATOM | 1295 | C | PHE | A | 174 | 42.504 | 0.301 | -16.970 | 1.00 12.18 |
| ATOM | 1296 | O | PHE | A | 174 | 43.413 | 0.347 | -16.133 | 1.00 11.61 |
| ATOM | 1297 | N | SER | A | 175 | 42.140 | 1.359 | -17.683 | 1.00 12.37 |
| ATOM | 1298 | CA | SER | A | 175 | 42.853 | 2.616 | -17.528 | 1.00 13.96 |
| ATOM | 1299 | CB | SER | A | 175 | 42.659 | 3.497 | -18.773 | 1.00 14.00 |
| ATOM | 1300 | OG | SER | A | 175 | 41.320 | 3.952 | -18.838 | 1.00 17.46 |
| ATOM | 1301 | C | SER | A | 175 | 42.472 | 3.437 | -16.322 | 1.00 13.59 |
| ATOM | 1302 | O | SER | A | 175 | 41.359 | 3.336 | -15.806 | 1.00 13.05 |
| ATOM | 1303 | N | PRO | A | 176 | 43.410 | 4.274 | -15.862 | 1.00 15.07 |
| ATOM | 1304 | CD | PRO | A | 176 | 44.835 | 4.282 | -16.249 | 1.00 15.14 |
| ATOM | 1305 | CA | PRO | A | 176 | 43.166 | 5.149 | -14.714 | 1.00 16.28 |
| ATOM | 1306 | CB | PRO | A | 176 | 44.447 | 5.977 | -14.641 | 1.00 16.83 |
| ATOM | 1307 | CG | PRO | A | 176 | 45.496 | 4.985 | -15.071 | 1.00 16.47 |
| ATOM | 1308 | C | PRO | A | 176 | 41.939 | 6.011 | -15.034 | 1.00 16.80 |
| ATOM | 1309 | O | PRO | A | 176 | 41.108 | 6.274 | -14.173 | 1.00 17.10 |
| ATOM | 1310 | N | ASP | A | 177 | 41.814 | 6.429 | -16.290 | 1.00 18.69 |
| ATOM | 1311 | CA | ASP | A | 177 | 40.677 | 7.262 | -16.687 | 1.00 20.41 |
| ATOM | 1312 | CB | ASP | A | 177 | 40.811 | 7.728 | -18.136 | 1.00 24.82 |
| ATOM | 1313 | CG | ASP | A | 177 | 41.805 | 8.844 | -18.282 | 1.00 30.14 |
| ATOM | 1314 | OD1 | ASP | A | 177 | 42.103 | 9.494 | -17.249 | 1.00 32.19 |
| ATOM | 1315 | OD2 | ASP | A | 177 | 42.281 | 9.082 | -19.421 | 1.00 34.87 |
| ATOM | 1316 | C | ASP | A | 177 | 39.332 | 6.592 | -16.530 | 1.00 19.21 |
| ATOM | 1317 | O | ASP | A | 177 | 38.332 | 7.266 | -16.346 | 1.00 19.53 |
| ATOM | 1318 | N | HIS | A | 178 | 39.301 | 5.270 | -16.617 | 1.00 17.70 |
| ATOM | 1319 | CA | HIS | A | 178 | 38.051 | 4.540 | -16.480 | 1.00 17.23 |
| ATOM | 1320 | CB | HIS | A | 178 | 38.022 | 3.377 | -17.470 | 1.00 18.66 |
| ATOM | 1321 | CG | HIS | A | 178 | 37.837 | 3.794 | -18.896 | 1.00 21.54 |
| ATOM | 1322 | CD2 | HIS | A | 178 | 37.077 | 4.768 | -19.449 | 1.00 21.89 |
| ATOM | 1323 | ND1 | HIS | A | 178 | 38.440 | 3.134 | -19.950 | 1.00 21.56 |
| ATOM | 1324 | CE1 | HIS | A | 178 | 38.057 | 3.685 | -21.087 | 1.00 22.49 |
| ATOM | 1325 | NE2 | HIS | A | 178 | 37.230 | 4.678 | -20.812 | 1.00 23.10 |
| ATOM | 1326 | C | HIS | A | 178 | 37.864 | 3.981 | -15.076 | 1.00 16.94 |
| ATOM | 1327 | O | HIS | A | 178 | 36.781 | 3.508 | -14.736 | 1.00 16.72 |
| ATOM | 1328 | N | ALA | A | 179 | 38.911 | 4.061 | -14.260 | 1.00 16.29 |
| ATOM | 1329 | CA | ALA | A | 179 | 38.887 | 3.485 | -12.918 | 1.00 15.55 |
| ATOM | 1330 | CB | ALA | A | 179 | 40.224 | 3.704 | -12.246 | 1.00 15.70 |
| ATOM | 1331 | C | ALA | A | 179 | 37.767 | 3.899 | -11.981 | 1.00 15.47 |
| ATOM | 1332 | O | ALA | A | 179 | 37.163 | 3.037 | -11.345 | 1.00 13.75 |
| ATOM | 1333 | N | GLU | A | 180 | 37.484 | 5.194 | -11.874 | 1.00 15.35 |
| ATOM | 1334 | CA | GLU | A | 180 | 36.420 | 5.629 | -10.968 | 1.00 16.79 |
| ATOM | 1335 | CB | GLU | A | 180 | 36.348 | 7.156 | -10.890 | 1.00 19.41 |
| ATOM | 1336 | CG | GLU | A | 180 | 37.552 | 7.814 | -10.202 | 1.00 24.62 |
| ATOM | 1337 | CD | GLU | A | 180 | 37.674 | 7.499 | -8.693 | 1.00 28.67 |
| ATOM | 1338 | OE1 | GLU | A | 180 | 36.690 | 7.028 | -8.066 | 1.00 29.66 |
| ATOM | 1339 | OE2 | GLU | A | 180 | 38.768 | 7.744 | -8.128 | 1.00 30.99 |
| ATOM | 1340 | C | GLU | A | 180 | 35.071 | 5.073 | -11.387 | 1.00 16.05 |
| ATOM | 1341 | O | GLU | A | 180 | 34.290 | 4.627 | -10.544 | 1.00 15.27 |
| ATOM | 1342 | N | GLN | A | 181 | 34.787 | 5.089 | -12.686 | 1.00 15.63 |
| ATOM | 1343 | CA | GLN | A | 181 | 33.515 | 4.552 | -13.155 | 1.00 16.77 |

Figure 9-22

```
ATOM   1344  CB   GLN A 181      33.261   4.960 -14.605  1.00 20.19
ATOM   1345  CG   GLN A 181      31.881   4.554 -15.078  1.00 26.27
ATOM   1346  CD   GLN A 181      30.766   5.119 -14.198  1.00 31.91
ATOM   1347  OE1  GLN A 181      29.636   4.619 -14.215  1.00 35.00
ATOM   1348  NE2  GLN A 181      31.075   6.174 -13.432  1.00 34.59
ATOM   1349  C    GLN A 181      33.461   3.019 -13.010  1.00 15.18
ATOM   1350  O    GLN A 181      32.405   2.453 -12.735  1.00 14.76
ATOM   1351  N    VAL A 182      34.595   2.348 -13.205  1.00 14.53
ATOM   1352  CA   VAL A 182      34.646   0.897 -13.033  1.00 14.14
ATOM   1353  CB   VAL A 182      36.061   0.330 -13.338  1.00 14.17
ATOM   1354  CG1  VAL A 182      36.197  -1.082 -12.750  1.00 13.37
ATOM   1355  CG2  VAL A 182      36.299   0.307 -14.839  1.00 13.09
ATOM   1356  C    VAL A 182      34.306   0.579 -11.569  1.00 14.54
ATOM   1357  O    VAL A 182      33.556  -0.351 -11.274  1.00 13.02
ATOM   1358  N    LEU A 183      34.859   1.374 -10.656  1.00 14.32
ATOM   1359  CA   LEU A 183      34.619   1.190  -9.227  1.00 15.17
ATOM   1360  CB   LEU A 183      35.482   2.172  -8.436  1.00 15.28
ATOM   1361  CG   LEU A 183      35.495   1.953  -6.935  1.00 18.22
ATOM   1362  CD1  LEU A 183      36.028   0.555  -6.623  1.00 17.20
ATOM   1363  CD2  LEU A 183      36.374   3.016  -6.297  1.00 19.00
ATOM   1364  C    LEU A 183      33.136   1.380  -8.866  1.00 14.56
ATOM   1365  O    LEU A 183      32.569   0.590  -8.106  1.00 14.80
ATOM   1366  N    VAL A 184      32.508   2.419  -9.416  1.00 14.43
ATOM   1367  CA   VAL A 184      31.095   2.685  -9.152  1.00 14.34
ATOM   1368  CB   VAL A 184      30.609   3.966  -9.900  1.00 15.18
ATOM   1369  CG1  VAL A 184      29.095   4.087  -9.813  1.00 15.02
ATOM   1370  CG2  VAL A 184      31.278   5.205  -9.306  1.00 16.65
ATOM   1371  C    VAL A 184      30.236   1.505  -9.603  1.00 14.26
ATOM   1372  O    VAL A 184      29.366   1.026  -8.863  1.00 13.45
ATOM   1373  N    LYS A 185      30.479   1.029 -10.825  1.00 14.16
ATOM   1374  CA   LYS A 185      29.704  -0.092 -11.358  1.00 13.94
ATOM   1375  CB   LYS A 185      29.936  -0.239 -12.869  1.00 16.28
ATOM   1376  CG   LYS A 185      29.630   1.018 -13.682  1.00 18.78
ATOM   1377  CD   LYS A 185      28.159   1.373 -13.670  1.00 24.08
ATOM   1378  CE   LYS A 185      27.327   0.349 -14.434  1.00 28.15
ATOM   1379  NZ   LYS A 185      25.863   0.700 -14.455  1.00 31.05
ATOM   1380  C    LYS A 185      30.026  -1.411 -10.649  1.00 13.35
ATOM   1381  O    LYS A 185      29.142  -2.260 -10.493  1.00 13.37
ATOM   1382  N    ALA A 186      31.281  -1.597 -10.229  1.00 13.57
ATOM   1383  CA   ALA A 186      31.660  -2.823  -9.518  1.00 14.15
ATOM   1384  CB   ALA A 186      33.161  -2.827  -9.208  1.00 12.75
ATOM   1385  C    ALA A 186      30.844  -2.909  -8.218  1.00 15.02
ATOM   1386  O    ALA A 186      30.326  -3.977  -7.860  1.00 14.46
ATOM   1387  N    ARG A 187      30.719  -1.774  -7.529  1.00 15.42
ATOM   1388  CA   ARG A 187      29.954  -1.711  -6.288  1.00 15.40
ATOM   1389  CB   ARG A 187      30.135  -0.348  -5.625  1.00 16.39
ATOM   1390  CG   ARG A 187      31.497  -0.239  -4.961  1.00 19.24
ATOM   1391  CD   ARG A 187      31.794   1.154  -4.434  1.00 22.98
ATOM   1392  NE   ARG A 187      33.080   1.162  -3.743  1.00 27.03
ATOM   1393  CZ   ARG A 187      33.861   2.227  -3.626  1.00 28.40
ATOM   1394  NH1  ARG A 187      33.487   3.387  -4.158  1.00 28.85
ATOM   1395  NH2  ARG A 187      35.023   2.123  -2.990  1.00 29.27
ATOM   1396  C    ARG A 187      28.481  -1.999  -6.515  1.00 15.91
ATOM   1397  O    ARG A 187      27.855  -2.665  -5.697  1.00 15.07
ATOM   1398  N    GLU A 188      27.924  -1.507  -7.625  1.00 15.49
ATOM   1399  CA   GLU A 188      26.518  -1.767  -7.937  1.00 15.64
ATOM   1400  CB   GLU A 188      26.079  -0.976  -9.177  1.00 17.71
ATOM   1401  CG   GLU A 188      26.055   0.533  -8.951  1.00 19.98
ATOM   1402  CD   GLU A 188      25.696   1.306 -10.205  1.00 23.32
ATOM   1403  OE1  GLU A 188      25.575   2.547 -10.135  1.00 24.71
ATOM   1404  OE2  GLU A 188      25.536   0.669 -11.268  1.00 25.08
ATOM   1405  C    GLU A 188      26.353  -3.268  -8.172  1.00 15.03
ATOM   1406  O    GLU A 188      25.359  -3.865  -7.760  1.00 15.74
ATOM   1407  N    HIS A 189      27.334  -3.884  -8.825  1.00 14.79
```

Figure 9-23

| | | | | | | | | | |
|---|---|---|---|---|---|---|---|---|---|
| ATOM | 1408 | CA | HIS | A | 189 | 27.267 | -5.320 | -9.056 | 1.00 15.41 |
| ATOM | 1409 | CB | HIS | A | 189 | 28.308 | -5.753 | -10.113 | 1.00 17.16 |
| ATOM | 1410 | CG | HIS | A | 189 | 27.866 | -5.503 | -11.526 | 1.00 18.65 |
| ATOM | 1411 | CD2 | HIS | A | 189 | 27.561 | -4.356 | -12.180 | 1.00 19.11 |
| ATOM | 1412 | ND1 | HIS | A | 189 | 27.647 | -6.523 | -12.431 | 1.00 20.60 |
| ATOM | 1413 | CE1 | HIS | A | 189 | 27.226 | -6.014 | -13.575 | 1.00 21.05 |
| ATOM | 1414 | NE2 | HIS | A | 189 | 27.166 | -4.699 | -13.450 | 1.00 20.12 |
| ATOM | 1415 | C | HIS | A | 189 | 27.436 | -6.092 | -7.729 | 1.00 14.81 |
| ATOM | 1416 | O | HIS | A | 189 | 26.807 | -7.133 | -7.563 | 1.00 14.79 |
| ATOM | 1417 | N | ASP | A | 190 | 28.260 | -5.593 | -6.798 | 1.00 15.28 |
| ATOM | 1418 | CA | ASP | A | 190 | 28.423 | -6.254 | -5.493 | 1.00 16.61 |
| ATOM | 1419 | CB | ASP | A | 190 | 29.417 | -5.515 | -4.595 | 1.00 19.95 |
| ATOM | 1420 | CG | ASP | A | 190 | 30.829 | -5.529 | -5.120 | 1.00 26.44 |
| ATOM | 1421 | OD1 | ASP | A | 190 | 31.215 | -6.453 | -5.875 | 1.00 28.14 |
| ATOM | 1422 | OD2 | ASP | A | 190 | 31.581 | -4.594 | -4.747 | 1.00 29.57 |
| ATOM | 1423 | C | ASP | A | 190 | 27.077 | -6.245 | -4.772 | 1.00 16.31 |
| ATOM | 1424 | O | ASP | A | 190 | 26.633 | -7.260 | -4.252 | 1.00 16.04 |
| ATOM | 1425 | N | ALA | A | 191 | 26.442 | -5.079 | -4.743 | 1.00 15.97 |
| ATOM | 1426 | CA | ALA | A | 191 | 25.155 | -4.929 | -4.086 | 1.00 15.86 |
| ATOM | 1427 | CB | ALA | A | 191 | 24.678 | -3.498 | -4.200 | 1.00 15.00 |
| ATOM | 1428 | C | ALA | A | 191 | 24.118 | -5.882 | -4.677 | 1.00 16.80 |
| ATOM | 1429 | O | ALA | A | 191 | 23.398 | -6.566 | -3.946 | 1.00 17.25 |
| ATOM | 1430 | N | HIS | A | 192 | 24.036 | -5.936 | -6.001 | 1.00 15.99 |
| ATOM | 1431 | CA | HIS | A | 192 | 23.082 | -6.824 | -6.642 | 1.00 16.80 |
| ATOM | 1432 | CB | HIS | A | 192 | 23.150 | -6.683 | -8.161 | 1.00 17.51 |
| ATOM | 1433 | CG | HIS | A | 192 | 22.173 | -7.560 | -8.876 | 1.00 19.58 |
| ATOM | 1434 | CD2 | HIS | A | 192 | 20.818 | -7.557 | -8.889 | 1.00 19.15 |
| ATOM | 1435 | ND1 | HIS | A | 192 | 22.559 | -8.642 | -9.642 | 1.00 21.29 |
| ATOM | 1436 | CE1 | HIS | A | 192 | 21.485 | -9.267 | -10.091 | 1.00 18.65 |
| ATOM | 1437 | NE2 | HIS | A | 192 | 20.416 | -8.628 | -9.648 | 1.00 20.64 |
| ATOM | 1438 | C | HIS | A | 192 | 23.380 | -8.268 | -6.262 | 1.00 16.51 |
| ATOM | 1439 | O | HIS | A | 192 | 22.469 | -9.038 | -5.939 | 1.00 17.52 |
| ATOM | 1440 | N | GLU | A | 193 | 24.659 | -8.626 | -6.296 | 1.00 16.07 |
| ATOM | 1441 | CA | GLU | A | 193 | 25.099 | -9.981 | -5.966 | 1.00 17.37 |
| ATOM | 1442 | CB | GLU | A | 193 | 26.623 | -10.081 | -6.131 | 1.00 19.03 |
| ATOM | 1443 | CG | GLU | A | 193 | 27.234 | -11.473 | -5.961 | 1.00 23.49 |
| ATOM | 1444 | CD | GLU | A | 193 | 27.610 | -11.792 | -4.518 | 1.00 28.60 |
| ATOM | 1445 | OE1 | GLU | A | 193 | 27.917 | -10.844 | -3.747 | 1.00 30.88 |
| ATOM | 1446 | OE2 | GLU | A | 193 | 27.625 | -12.996 | -4.161 | 1.00 29.08 |
| ATOM | 1447 | C | GLU | A | 193 | 24.676 | -10.360 | -4.543 | 1.00 16.87 |
| ATOM | 1448 | O | GLU | A | 193 | 24.203 | -11.475 | -4.302 | 1.00 16.58 |
| ATOM | 1449 | N | GLN | A | 194 | 24.842 | -9.438 | -3.603 | 1.00 16.36 |
| ATOM | 1450 | CA | GLN | A | 194 | 24.449 | -9.707 | -2.224 | 1.00 17.00 |
| ATOM | 1451 | CB | GLN | A | 194 | 24.884 | -8.562 | -1.332 | 1.00 18.85 |
| ATOM | 1452 | CG | GLN | A | 194 | 26.369 | -8.444 | -1.225 | 1.00 23.80 |
| ATOM | 1453 | CD | GLN | A | 194 | 26.787 | -7.060 | -0.801 | 1.00 28.51 |
| ATOM | 1454 | OE1 | GLN | A | 194 | 27.979 | -6.747 | -0.735 | 1.00 31.49 |
| ATOM | 1455 | NE2 | GLN | A | 194 | 25.802 | -6.210 | -0.513 | 1.00 31.51 |
| ATOM | 1456 | C | GLN | A | 194 | 22.935 | -9.900 | -2.112 | 1.00 16.65 |
| ATOM | 1457 | O | GLN | A | 194 | 22.465 | -10.737 | -1.344 | 1.00 16.04 |
| ATOM | 1458 | N | GLN | A | 195 | 22.167 | -9.128 | -2.874 | 1.00 16.22 |
| ATOM | 1459 | CA | GLN | A | 195 | 20.721 | -9.279 | -2.833 | 1.00 17.85 |
| ATOM | 1460 | CB | GLN | A | 195 | 20.046 | -8.170 | -3.635 | 1.00 20.88 |
| ATOM | 1461 | CG | GLN | A | 195 | 20.278 | -6.786 | -3.050 | 1.00 29.48 |
| ATOM | 1462 | CD | GLN | A | 195 | 19.897 | -5.656 | -4.013 | 1.00 35.87 |
| ATOM | 1463 | OE1 | GLN | A | 195 | 18.731 | -5.528 | -4.414 | 1.00 39.94 |
| ATOM | 1464 | NE2 | GLN | A | 195 | 20.885 | -4.829 | -4.389 | 1.00 38.21 |
| ATOM | 1465 | C | GLN | A | 195 | 20.328 | -10.652 | -3.383 | 1.00 16.41 |
| ATOM | 1466 | O | GLN | A | 195 | 19.538 | -11.374 | -2.774 | 1.00 16.29 |
| ATOM | 1467 | N | VAL | A | 196 | 20.878 | -11.017 | -4.536 | 1.00 14.87 |
| ATOM | 1468 | CA | VAL | A | 196 | 20.578 | -12.313 | -5.133 | 1.00 13.08 |
| ATOM | 1469 | CB | VAL | A | 196 | 21.306 | -12.470 | -6.494 | 1.00 13.55 |
| ATOM | 1470 | CG1 | VAL | A | 196 | 21.144 | -13.892 | -7.019 | 1.00 12.16 |
| ATOM | 1471 | CG2 | VAL | A | 196 | 20.737 | -11.451 | -7.498 | 1.00 12.39 |

Figure 9-24

```
ATOM   1472  C    VAL A 196     20.988 -13.458  -4.190  1.00 12.91
ATOM   1473  O    VAL A 196     20.222 -14.401  -3.988  1.00 11.87
ATOM   1474  N    LYS A 197     22.187 -13.376  -3.616  1.00 12.83
ATOM   1475  CA   LYS A 197     22.653 -14.406  -2.691  1.00 12.89
ATOM   1476  CB   LYS A 197     24.068 -14.088  -2.206  1.00 14.26
ATOM   1477  CG   LYS A 197     24.654 -15.174  -1.310  1.00 18.10
ATOM   1478  CD   LYS A 197     26.084 -14.871  -0.896  1.00 21.70
ATOM   1479  CE   LYS A 197     27.022 -14.920  -2.089  1.00 22.88
ATOM   1480  NZ   LYS A 197     28.454 -14.796  -1.678  1.00 22.79
ATOM   1481  C    LYS A 197     21.681 -14.523  -1.496  1.00 13.09
ATOM   1482  O    LYS A 197     21.319 -15.629  -1.089  1.00 13.11
ATOM   1483  N    ALA A 198     21.246 -13.391  -0.950  1.00 13.07
ATOM   1484  CA   ALA A 198     20.301 -13.412   0.165  1.00 12.86
ATOM   1485  CB   ALA A 198     20.077 -12.002   0.688  1.00 12.87
ATOM   1486  C    ALA A 198     18.966 -14.032  -0.278  1.00 13.60
ATOM   1487  O    ALA A 198     18.388 -14.839   0.447  1.00 13.19
ATOM   1488  N    GLU A 199     18.469 -13.671  -1.464  1.00 12.83
ATOM   1489  CA   GLU A 199     17.208 -14.241  -1.947  1.00 12.37
ATOM   1490  CB   GLU A 199     16.758 -13.596  -3.274  1.00 12.45
ATOM   1491  CG   GLU A 199     15.295 -13.937  -3.608  1.00 14.34
ATOM   1492  CD   GLU A 199     14.759 -13.294  -4.887  1.00 14.40
ATOM   1493  OE1  GLU A 199     13.581 -13.562  -5.232  1.00 14.44
ATOM   1494  OE2  GLU A 199     15.500 -12.516  -5.538  1.00 16.01
ATOM   1495  C    GLU A 199     17.321 -15.763  -2.127  1.00 12.27
ATOM   1496  O    GLU A 199     16.389 -16.506  -1.815  1.00 12.11
ATOM   1497  N    ILE A 200     18.463 -16.235  -2.624  1.00 11.71
ATOM   1498  CA   ILE A 200     18.655 -17.662  -2.812  1.00 11.54
ATOM   1499  CB   ILE A 200     20.001 -17.973  -3.551  1.00 11.63
ATOM   1500  CG2  ILE A 200     20.295 -19.479  -3.508  1.00 11.07
ATOM   1501  CG1  ILE A 200     19.936 -17.475  -4.999  1.00 11.39
ATOM   1502  CD1  ILE A 200     21.278 -17.532  -5.718  1.00 10.74
ATOM   1503  C    ILE A 200     18.681 -18.341  -1.441  1.00 12.29
ATOM   1504  O    ILE A 200     18.103 -19.413  -1.255  1.00 12.09
ATOM   1505  N    ALA A 201     19.338 -17.692  -0.485  1.00 12.93
ATOM   1506  CA   ALA A 201     19.476 -18.239   0.864  1.00 13.91
ATOM   1507  CB   ALA A 201     20.468 -17.389   1.676  1.00 11.40
ATOM   1508  C    ALA A 201     18.149 -18.406   1.620  1.00 14.01
ATOM   1509  O    ALA A 201     18.099 -19.148   2.613  1.00 14.93
ATOM   1510  N    THR A 202     17.087 -17.729   1.178  1.00 13.23
ATOM   1511  CA   THR A 202     15.775 -17.898   1.822  1.00 12.49
ATOM   1512  CB   THR A 202     14.691 -16.945   1.287  1.00 12.35
ATOM   1513  OG1  THR A 202     14.516 -17.164  -0.123  1.00 12.40
ATOM   1514  CG2  THR A 202     15.041 -15.507   1.568  1.00 12.62
ATOM   1515  C    THR A 202     15.242 -19.305   1.559  1.00 12.67
ATOM   1516  O    THR A 202     14.326 -19.765   2.246  1.00 13.32
ATOM   1517  N    GLY A 203     15.803 -19.975   0.548  1.00 11.46
ATOM   1518  CA   GLY A 203     15.369 -21.312   0.199  1.00 10.46
ATOM   1519  C    GLY A 203     14.213 -21.332  -0.790  1.00  9.85
ATOM   1520  O    GLY A 203     13.824 -22.394  -1.279  1.00 11.01
ATOM   1521  N    ALA A 204     13.657 -20.165  -1.099  1.00 10.69
ATOM   1522  CA   ALA A 204     12.521 -20.103  -2.018  1.00 11.58
ATOM   1523  CB   ALA A 204     12.013 -18.678  -2.119  1.00 10.58
ATOM   1524  C    ALA A 204     12.864 -20.629  -3.419  1.00 12.85
ATOM   1525  O    ALA A 204     13.929 -20.321  -3.963  1.00 12.04
ATOM   1526  N    ILE A 205     11.955 -21.428  -3.981  1.00 12.43
ATOM   1527  CA   ILE A 205     12.138 -21.963  -5.324  1.00 13.82
ATOM   1528  CB   ILE A 205     11.061 -23.023  -5.646  1.00 13.65
ATOM   1529  CG2  ILE A 205     11.024 -23.312  -7.154  1.00 14.66
ATOM   1530  CG1  ILE A 205     11.341 -24.282  -4.832  1.00 14.52
ATOM   1531  CD1  ILE A 205     10.201 -25.268  -4.826  1.00 16.23
ATOM   1532  C    ILE A 205     12.036 -20.787  -6.298  1.00 14.36
ATOM   1533  O    ILE A 205     12.912 -20.586  -7.143  1.00 15.59
ATOM   1534  N    ASP A 206     10.990 -19.983  -6.165  1.00 13.78
ATOM   1535  CA   ASP A 206     10.844 -18.842  -7.051  1.00 14.24
```

Figure 9-25

```
ATOM   1536  CB  ASP A 206       9.468 -18.204  -6.904  1.00 15.24
ATOM   1537  CG  ASP A 206       9.306 -17.000  -7.802  1.00 17.51
ATOM   1538  OD1 ASP A 206       9.302 -17.189  -9.041  1.00 18.09
ATOM   1539  OD2 ASP A 206       9.206 -15.872  -7.274  1.00 17.88
ATOM   1540  C   ASP A 206      11.905 -17.800  -6.737  1.00 14.46
ATOM   1541  O   ASP A 206      12.145 -17.489  -5.572  1.00 14.57
ATOM   1542  N   GLN A 207      12.536 -17.255  -7.775  1.00 13.18
ATOM   1543  CA  GLN A 207      13.571 -16.242  -7.603  1.00 13.29
ATOM   1544  CB  GLN A 207      14.954 -16.846  -7.842  1.00 13.15
ATOM   1545  CG  GLN A 207      15.393 -17.891  -6.822  1.00 12.99
ATOM   1546  CD  GLN A 207      15.738 -17.291  -5.459  1.00 14.09
ATOM   1547  OE1 GLN A 207      16.525 -16.344  -5.354  1.00 14.16
ATOM   1548  NE2 GLN A 207      15.151 -17.854  -4.403  1.00 14.90
ATOM   1549  C   GLN A 207      13.340 -15.107  -8.581  1.00 14.18
ATOM   1550  O   GLN A 207      13.206 -15.335  -9.778  1.00 15.38
ATOM   1551  N   SER A 208      13.299 -13.884  -8.078  1.00 13.62
ATOM   1552  CA  SER A 208      13.056 -12.729  -8.927  1.00 15.01
ATOM   1553  CB  SER A 208      13.097 -11.438  -8.093  1.00 15.55
ATOM   1554  OG  SER A 208      14.390 -11.183  -7.573  1.00 16.55
ATOM   1555  C   SER A 208      14.059 -12.627 -10.075  1.00 15.59
ATOM   1556  O   SER A 208      13.669 -12.410 -11.226  1.00 16.04
ATOM   1557  N   TRP A 209      15.342 -12.793  -9.767  1.00 14.91
ATOM   1558  CA  TRP A 209      16.392 -12.691 -10.780  1.00 14.31
ATOM   1559  CB  TRP A 209      17.783 -12.767 -10.131  1.00 14.42
ATOM   1560  CG  TRP A 209      17.987 -13.989  -9.278  1.00 14.99
ATOM   1561  CD2 TRP A 209      18.518 -15.258  -9.697  1.00 15.11
ATOM   1562  CE2 TRP A 209      18.424 -16.138  -8.589  1.00 15.24
ATOM   1563  CE3 TRP A 209      19.064 -15.739 -10.898  1.00 16.00
ATOM   1564  CD1 TRP A 209      17.608 -14.148  -7.965  1.00 14.47
ATOM   1565  NE1 TRP A 209      17.865 -15.433  -7.550  1.00 14.73
ATOM   1566  CZ2 TRP A 209      18.842 -17.468  -8.651  1.00 14.37
ATOM   1567  CZ3 TRP A 209      19.479 -17.064 -10.957  1.00 15.27
ATOM   1568  CH2 TRP A 209      19.369 -17.913  -9.838  1.00 15.85
ATOM   1569  C   TRP A 209      16.277 -13.767 -11.857  1.00 15.03
ATOM   1570  O   TRP A 209      16.590 -13.525 -13.027  1.00 14.63
ATOM   1571  N   LEU A 210      15.838 -14.956 -11.458  1.00 13.36
ATOM   1572  CA  LEU A 210      15.695 -16.071 -12.388  1.00 14.07
ATOM   1573  CB  LEU A 210      15.530 -17.378 -11.602  1.00 13.21
ATOM   1574  CG  LEU A 210      15.449 -18.691 -12.380  1.00 14.03
ATOM   1575  CD1 LEU A 210      16.520 -18.738 -13.467  1.00 14.74
ATOM   1576  CD2 LEU A 210      15.627 -19.843 -11.400  1.00 14.39
ATOM   1577  C   LEU A 210      14.492 -15.819 -13.294  1.00 14.55
ATOM   1578  O   LEU A 210      14.555 -16.038 -14.510  1.00 14.02
ATOM   1579  N   ASP A 211      13.401 -15.348 -12.694  1.00 14.00
ATOM   1580  CA  ASP A 211      12.185 -15.030 -13.436  1.00 15.45
ATOM   1581  CB  ASP A 211      11.098 -14.533 -12.483  1.00 16.05
ATOM   1582  CG  ASP A 211      10.565 -15.629 -11.589  1.00 16.66
ATOM   1583  OD1 ASP A 211       9.972 -15.284 -10.538  1.00 18.51
ATOM   1584  OD2 ASP A 211      10.729 -16.820 -11.935  1.00 16.13
ATOM   1585  C   ASP A 211      12.447 -13.946 -14.478  1.00 15.62
ATOM   1586  O   ASP A 211      11.956 -14.026 -15.603  1.00 16.77
ATOM   1587  N   LYS A 212      13.214 -12.932 -14.098  1.00 15.81
ATOM   1588  CA  LYS A 212      13.514 -11.836 -15.014  1.00 17.08
ATOM   1589  CB  LYS A 212      14.424 -10.823 -14.328  1.00 18.63
ATOM   1590  CG  LYS A 212      14.562  -9.518 -15.085  1.00 24.05
ATOM   1591  CD  LYS A 212      15.529  -8.570 -14.385  1.00 27.24
ATOM   1592  CE  LYS A 212      15.762  -7.304 -15.207  1.00 29.57
ATOM   1593  NZ  LYS A 212      16.901  -6.490 -14.672  1.00 32.49
ATOM   1594  C   LYS A 212      14.184 -12.358 -16.292  1.00 17.14
ATOM   1595  O   LYS A 212      13.769 -12.040 -17.407  1.00 16.59
ATOM   1596  N   VAL A 213      15.219 -13.170 -16.119  1.00 16.04
ATOM   1597  CA  VAL A 213      15.953 -13.749 -17.242  1.00 15.76
ATOM   1598  CB  VAL A 213      17.148 -14.571 -16.717  1.00 15.12
ATOM   1599  CG1 VAL A 213      17.759 -15.402 -17.836  1.00 14.46
```

Figure 9-26

```
ATOM   1600  CG2 VAL A 213      18.185 -13.626 -16.121  1.00 15.08
ATOM   1601  C   VAL A 213      15.084 -14.644 -18.130  1.00 16.08
ATOM   1602  O   VAL A 213      15.050 -14.490 -19.352  1.00 14.68
ATOM   1603  N   LEU A 214      14.382 -15.585 -17.511  1.00 15.21
ATOM   1604  CA  LEU A 214      13.544 -16.512 -18.256  1.00 16.13
ATOM   1605  CB  LEU A 214      12.995 -17.586 -17.315  1.00 15.78
ATOM   1606  CG  LEU A 214      13.742 -18.921 -17.246  1.00 18.81
ATOM   1607  CD1 LEU A 214      15.187 -18.757 -17.620  1.00 17.33
ATOM   1608  CD2 LEU A 214      13.570 -19.524 -15.860  1.00 15.73
ATOM   1609  C   LEU A 214      12.401 -15.812 -18.977  1.00 16.95
ATOM   1610  O   LEU A 214      12.084 -16.142 -20.118  1.00 16.97
ATOM   1611  N   GLU A 215      11.782 -14.843 -18.320  1.00 16.82
ATOM   1612  CA  GLU A 215      10.680 -14.126 -18.940  1.00 18.90
ATOM   1613  CB  GLU A 215      10.005 -13.205 -17.921  1.00 20.78
ATOM   1614  CG  GLU A 215       9.198 -13.954 -16.880  1.00 24.49
ATOM   1615  CD  GLU A 215       8.772 -13.072 -15.716  1.00 29.64
ATOM   1616  OE1 GLU A 215       8.126 -13.590 -14.782  1.00 31.18
ATOM   1617  OE2 GLU A 215       9.086 -11.864 -15.726  1.00 32.68
ATOM   1618  C   GLU A 215      11.172 -13.315 -20.130  1.00 19.43
ATOM   1619  O   GLU A 215      10.539 -13.306 -21.186  1.00 19.16
ATOM   1620  N   LYS A 216      12.297 -12.633 -19.965  1.00 19.61
ATOM   1621  CA  LYS A 216      12.824 -11.830 -21.050  1.00 21.12
ATOM   1622  CB  LYS A 216      14.075 -11.080 -20.602  1.00 23.10
ATOM   1623  CG  LYS A 216      14.623 -10.147 -21.671  1.00 28.01
ATOM   1624  CD  LYS A 216      15.905  -9.470 -21.215  1.00 31.73
ATOM   1625  CE  LYS A 216      16.380  -8.427 -22.220  1.00 33.95
ATOM   1626  NZ  LYS A 216      17.574  -7.703 -21.691  1.00 37.61
ATOM   1627  C   LYS A 216      13.160 -12.706 -22.257  1.00 21.25
ATOM   1628  O   LYS A 216      13.007 -12.283 -23.402  1.00 21.63
ATOM   1629  N   ALA A 217      13.597 -13.935 -22.005  1.00 19.04
ATOM   1630  CA  ALA A 217      13.971 -14.825 -23.088  1.00 18.72
ATOM   1631  CB  ALA A 217      15.070 -15.763 -22.616  1.00 18.54
ATOM   1632  C   ALA A 217      12.811 -15.638 -23.642  1.00 18.92
ATOM   1633  O   ALA A 217      12.996 -16.420 -24.571  1.00 19.01
ATOM   1634  N   GLY A 218      11.620 -15.467 -23.081  1.00 18.29
ATOM   1635  CA  GLY A 218      10.483 -16.249 -23.541  1.00 18.79
ATOM   1636  C   GLY A 218      10.580 -17.707 -23.109  1.00 19.82
ATOM   1637  O   GLY A 218       9.963 -18.602 -23.710  1.00 19.64
ATOM   1638  N   LEU A 219      11.347 -17.960 -22.050  1.00 18.51
ATOM   1639  CA  LEU A 219      11.527 -19.323 -21.562  1.00 18.96
ATOM   1640  CB  LEU A 219      13.027 -19.646 -21.472  1.00 17.67
ATOM   1641  CG  LEU A 219      13.799 -19.758 -22.789  1.00 18.00
ATOM   1642  CD1 LEU A 219      15.279 -19.929 -22.512  1.00 18.07
ATOM   1643  CD2 LEU A 219      13.278 -20.936 -23.576  1.00 17.81
ATOM   1644  C   LEU A 219      10.872 -19.597 -20.203  1.00 20.17
ATOM   1645  O   LEU A 219      11.258 -20.546 -19.519  1.00 19.78
ATOM   1646  N   ALA A 220       9.888 -18.794 -19.805  1.00 21.11
ATOM   1647  CA  ALA A 220       9.248 -19.027 -18.506  1.00 23.87
ATOM   1648  CB  ALA A 220       8.595 -17.747 -18.006  1.00 22.46
ATOM   1649  C   ALA A 220       8.223 -20.160 -18.554  1.00 25.66
ATOM   1650  O   ALA A 220       7.711 -20.460 -19.656  1.00 27.82
ATOM   1651  OXT ALA A 220       7.944 -20.740 -17.481  1.00 28.23
END
```

Figure 10

SLPGSRIYPSPPQAPRSLLDAFQNVVTPHISDNLGRHIGARGLTRYNHTGKLVGTALTVKTRPGDNLYIYKALTL

IEPGHVLVIDAQGDATNAVIGELIKLYAQQRGCVGFVVDGAIRDVASFEDTPCYARSVVHCGPYKSGPGEINVPV

SIGGMIINPGDIIVGDEDGLVAFSPDHAEQVLVKAREHDAHEQQVKAEIATGAIDQSWLDKVLEKAGLA

Figure 15

PcALD
PtALD

I-GFRVLSAARKVSPEWVARYRDVPVANVSDSMNDMTAGGSRLRPMHRAGVLAGPALTVKARPGDDLMLAYAIDI
LPGSRIYPSPPQAPRSLLDAFQNVVTPHISDNLGE-HIGARGLTRYNHTGKLVGTALTVKTRPGDQLYIYKALTL
* * * * * * * * **** *

AQPGDVIVVDAGGDLTNALIGENAYAYAVKRGVAGIVINGAIRDAASIGAGDFPMFAAGVSHRGPYKDGPGEINV
IEPGHVLVIDAQGDATNAVIGELIKLYAQQRGCVGFVVDGAIRDVASFE--DTPCYARSVVHCGPYKSGPGEINV
  *** * ** * * * *** *

PIAIDGMVIEAGDLVIGDDDGLLCVPYDQVAEVYDRAAAKHHAEQKQLEQIAKGENDRSIVLESLKKGCQ
PVSIGGMIINPGDIIVGDEDGLVAFSPDHAEQVLVKAREKDAHFQQVKAEIATGAIDQSILDKVLEKAGLA
*   * *  ** *

Figure 16

PcmE
PtALD

```
                                                               37
I----ERPDPADVKR--LSQFG---VATIHEAMGRVGLLRPYIRPAYTGAKLCGPAVTVLLQPGDWMFAVAAEQ
LPGSRIYPSPPQAPRSLLDAFQNVVTPHISDNLGHHIGARGLTRYNHTG-KLVGTALTVKTRPGDALYIKKALTL
*           *          *          *     **   ****** *   *

99                         120
VQEGDVIVAGCTTESEDGFFGELATSLTARGCKGLVIDGGVRDVADLEKMDFPVFSRAVNAKGFVKATLGSVNI
IEPGHVLVIDAQGDATNAVIGELKLYAQQRGCVGFVVDGAIRDVASFE--DTPCYARSVVHCGPYKSGPGEINV
 * *** *           **      * ***  **  **  *    *  *    *    *

PVVVANAVVNPGDVVVADVDGVVVVPRELVGAVADASQKREDKEEAKRVKFREGVLGLDVYGMRGPLAKAGLE
PVSIGGMIINPGDIIVGDEDGLVAFSPDHAEQVLVKAREKDAHEQQVKAEIATG--AIDQSHLDKVLEKAGLA
**      **** *     *           *               *                  ****  *
```

Figure 17

ProA    L--GVVYRNIQRADRAAADGLAALGSATVHEAMGRVGLLKPYMRPIYAGKQVSGTAVTVLLQPGDWMMWVAAEQ
PtALD   LPGSRIYPSPPQAPRSLLDAFQNVVTPHISDNLGRHIGARGLTRYNHTGKLV-GTALTVKTRPGDMLYIYKALTL
         *   *** *      *     *  *   *  *     *  *   * *   *     *    *

ProA    IQPGDIVVAAVTAECTDGYFGRLATSFQARGARALIIDAGVRDVKTLQEMDFPVWSKAISSKGTIKATLGSVNI
PtALD   IEPGHVLVIDAQGDATNAVIGELKLYAQQRGCVGFVVDGAIRDVASFE--DTPCYARSVVHCGPYKSGPGEINV
         * *  ** *   *    *       *  ** * *    *  *      *       *  *  **  *

ProA    PIVCAGMLVTPGDVIVADDDGVVCVPAARAVEVLAAAQKRESFEGEKRAKLASGVLGLDMYKMREPLEKAGLK
PtALD   PVSIGGMIINPGDIIVGDEDGLVAFSPDHAEQVLVKAREHDAHEQQVKAEIATG--AIDQSHLDKVLEKAGLA

SEQUENCE LISTING

<160> NUMBER OF SEQ ID NOS: 25

<210> SEQ ID NO 1
<211> LENGTH: 1296
<212> TYPE: DNA
<213> ORGANISM: Pseudomonas taetrolens
<220> FEATURE:
<221> NAME/KEY: CDS
<222> LOCATION: (456)..(1118)

<400> SEQUENCE: 1

```
gtacaccgtc ctgactcagg gcgcgctcgg cacgggttga tctatgagcg ctgtttgccc      60
agaatgacgt cggggtcacg tacgatcaaa gcaactacct gatcgcccag tgggcctgac     120
ctgtccggtg tcggcatcag ctacctgcct cgccaagtgt ctctcgccat ggtggaccat     180
gggtcgggct actagtcatc gaaaccgagc ctgcgctgcc tcccatccaa tacatcgccg     240
tacaccgcgc cgatcgtctt cagggcctca gcgtcgaggt tgcacgtctg gcagctcgtt     300
gctgtgattt cagccgcatg gtgtggtaac acaggcgctg gatacgagaa aaaaagcgat     360
gtattttcat agataaatat cgctaatagt gccaagcgac ctttcttact atgaacgcat     420
agcccacaag ggttcagtca ttcatggagg tcgct atg tca ttg ccc ggt tca       473
                                    Met Ser Leu Pro Gly Ser
                                      1               5 cgc atc tac cct tct ccg ccc cag gca cca cgc tca ctg ctg gac gcg       521
Arg Ile Tyr Pro Ser Pro Pro Gln Ala Pro Arg Ser Leu Leu Asp Ala
         10                  15                  20 ttt cag aac gta gtg acg ccg cat atc agt gat aac ctc ggg cgt cac       569
Phe Gln Asn Val Val Thr Pro His Ile Ser Asp Asn Leu Gly Arg His
     25                  30                  35 atc ggt gcc cgg ggg ctg acg cgc tat aac cac acc ggc aaa ctg gtg       617
Ile Gly Ala Arg Gly Leu Thr Arg Tyr Asn His Thr Gly Lys Leu Val
 40                  45                  50 ggc acc gcc ctg acg gtg aag act cgc ccc ggc gac aac ctc tac atc       665
Gly Thr Ala Leu Thr Val Lys Thr Arg Pro Gly Asp Asn Leu Tyr Ile
55                  60                  65                  70 tac aaa gca ctg acg ctg atc gaa ccc gga cac gtg ctg gtg atc gac       713
Tyr Lys Ala Leu Thr Leu Ile Glu Pro Gly His Val Leu Val Ile Asp
                 75                  80                  85 gct cag ggt gac gcg acc aac gcg gtc att ggt gag ctg atc aag ctc       761
Ala Gln Gly Asp Ala Thr Asn Ala Val Ile Gly Glu Leu Ile Lys Leu
             90                  95                 100 tac gcg cag caa cgt ggc tgt gtc ggc ttc gtc gtc gac ggc gcc atc       809
Tyr Ala Gln Gln Arg Gly Cys Val Gly Phe Val Val Asp Gly Ala Ile
        105                 110                 115 cgc gat gtc gcc agt ttt gaa gat acg cct tgc tat gcc cgt agc gtg       857
Arg Asp Val Ala Ser Phe Glu Asp Thr Pro Cys Tyr Ala Arg Ser Val
    120                 125                 130 gtg cat tgc ggt ccc tac aaa agc ggc cca ggg gaa atc aat gtc ccg       905
Val His Cys Gly Pro Tyr Lys Ser Gly Pro Gly Glu Ile Asn Val Pro
135                 140                 145                 150 gtg tca atc ggc ggg atg atc atc aat ccg ggc gac atc att gtc ggt       953
Val Ser Ile Gly Gly Met Ile Ile Asn Pro Gly Asp Ile Ile Val Gly
                155                 160                 165 gac gag gat ggg ctg gtt gcc ttc tcg ccc gac cat gcc gag cag gtg      1001
Asp Glu Asp Gly Leu Val Ala Phe Ser Pro Asp His Ala Glu Gln Val
            170                 175                 180 ttg gtc aag gcg cga gag cat gac gcg cat gaa cag cag gtc aaa gcc      1049
Leu Val Lys Ala Arg Glu His Asp Ala His Glu Gln Gln Val Lys Ala
        185                 190                 195
```

-continued

```
                      185                 190                 195
gaa atc gcc act ggc gcc atc gat cag tca tgg ctg gac aaa gtg ctg    1097
Glu Ile Ala Thr Gly Ala Ile Asp Gln Ser Trp Leu Asp Lys Val Leu
        200                 205                 210 gaa aag gct ggc ctg gcg aac tgaaaaacac tgtgtaatcg ccttgctgca       1148
Glu Lys Ala Gly Leu Ala Asn
215                 220 gcgacattgc tgtcggacag gatgatctga cgcttcagtt acgcgttctt gggtgcaccg    1208
cgccacgtca ggaagtggct gctgccgcat gcaggtgaca tgtcatgtac catggcagca    1268
gcacgtgaca tgcacgatgt gctcacgc                                       1296

<210> SEQ ID NO 2
<211> LENGTH: 221
<212> TYPE: PRT
<213> ORGANISM: Pseudomonas taetrolens

<400> SEQUENCE: 2

Met Ser Leu Pro Gly Ser Arg Ile Tyr Pro Ser Pro Gln Ala Pro
1               5                   10                  15

Arg Ser Leu Leu Asp Ala Phe Gln Asn Val Val Thr Pro His Ile Ser
            20                  25                  30

Asp Asn Leu Gly Arg His Ile Gly Ala Arg Gly Leu Thr Arg Tyr Asn
        35                  40                  45

His Thr Gly Lys Leu Val Gly Thr Ala Leu Thr Val Lys Thr Arg Pro
    50                  55                  60

Gly Asp Asn Leu Tyr Ile Tyr Lys Ala Leu Thr Leu Ile Glu Pro Gly
65                  70                  75                  80

His Val Leu Val Ile Asp Ala Gln Gly Asp Ala Thr Asn Ala Val Ile
                85                  90                  95

Gly Glu Leu Ile Lys Leu Tyr Ala Gln Gln Arg Gly Cys Val Gly Phe
            100                 105                 110

Val Val Asp Gly Ala Ile Arg Asp Val Ala Ser Phe Glu Asp Thr Pro
        115                 120                 125

Cys Tyr Ala Arg Ser Val Val His Cys Gly Pro Tyr Lys Ser Gly Pro
    130                 135                 140

Gly Glu Ile Asn Val Pro Val Ser Ile Gly Gly Met Ile Ile Asn Pro
145                 150                 155                 160

Gly Asp Ile Ile Val Gly Asp Glu Asp Gly Leu Val Ala Phe Ser Pro
                165                 170                 175

Asp His Ala Glu Gln Val Leu Val Lys Ala Arg Glu His Asp Ala His
            180                 185                 190

Glu Gln Gln Val Lys Ala Glu Ile Ala Thr Gly Ala Ile Asp Gln Ser
        195                 200                 205

Trp Leu Asp Lys Val Leu Glu Lys Ala Gly Leu Ala Asn
    210                 215                 220

<210> SEQ ID NO 3
<211> LENGTH: 40
<212> TYPE: DNA
<213> ORGANISM: Artificial Sequence
<220> FEATURE:
<223> OTHER INFORMATION: Synthetic DNA

<400> SEQUENCE: 3
gtatcacgag gccctagctg tggtgtcatg gtcggtgatc                          40
```

<210> SEQ ID NO 4
<211> LENGTH: 40
<212> TYPE: DNA
<213> ORGANISM: Artificial Sequence
<220> FEATURE:
<223> OTHER INFORMATION: Synthetic DNA

<400> SEQUENCE: 4
ttcggggatt ccatatgata ccctttttac gtgaacttgc            40

<210> SEQ ID NO 5
<211> LENGTH: 38
<212> TYPE: DNA
<213> ORGANISM: Artificial Sequence
<220> FEATURE:
<223> OTHER INFORMATION: Synthetic DNA

<400> SEQUENCE: 5
ggggggggca tatgcgacct ccttattacg tgaacttg              38

<210> SEQ ID NO 6
<211> LENGTH: 28
<212> TYPE: DNA
<213> ORGANISM: Artificial Sequence
<220> FEATURE:
<223> OTHER INFORMATION: Synthetic DNA

<400> SEQUENCE: 6
ccgaagcttt cagttcgcca ggccagcc                         28

<210> SEQ ID NO 7
<211> LENGTH: 33
<212> TYPE: DNA
<213> ORGANISM: Artificial Sequence
<220> FEATURE:
<223> OTHER INFORMATION: Synthetic DNA

<400> SEQUENCE: 7
atggaggtcc attagtcatt gcccggttca cgc                   33

<210> SEQ ID NO 8
<211> LENGTH: 30
<212> TYPE: DNA
<213> ORGANISM: Artificial Sequence
<220> FEATURE:
<223> OTHER INFORMATION: Synthetic DNA

<400> SEQUENCE: 8
gctctagaga aatgacgtgt tgacaattaa                       30

<210> SEQ ID NO 9
<211> LENGTH: 34
<212> TYPE: DNA
<213> ORGANISM: Artificial Sequence
<220> FEATURE:
<223> OTHER INFORMATION: Synthetic DNA

<400> SEQUENCE: 9
cagtgataac ctcgggtatc acatcggtgc ccgg                  34

<210> SEQ ID NO 10
<211> LENGTH: 34
<212> TYPE: DNA
<213> ORGANISM: Artificial Sequence
<220> FEATURE:
<223> OTHER INFORMATION: Synthetic DNA

```
<400> SEQUENCE: 10
cagtgataac ctcgggtggc acatcggtgc ccgg                                34

<210> SEQ ID NO 11
<211> LENGTH: 34
<212> TYPE: DNA
<213> ORGANISM: Artificial Sequence
<220> FEATURE:
<223> OTHER INFORMATION: Synthetic DNA

<400> SEQUENCE: 11
cagtgataac ctcgggcatc acatcggtgc ccgg                                34

<210> SEQ ID NO 12
<211> LENGTH: 34
<212> TYPE: DNA
<213> ORGANISM: Artificial Sequence
<220> FEATURE:
<223> OTHER INFORMATION: Synthetic DNA

<400> SEQUENCE: 12
cagtgataac ctcgggcctc acatcggtgc ccgg                                34

<210> SEQ ID NO 13
<211> LENGTH: 34
<212> TYPE: DNA
<213> ORGANISM: Artificial Sequence
<220> FEATURE:
<223> OTHER INFORMATION: Synthetic DNA

<400> SEQUENCE: 13
cagtgataac ctcgggtttc acatcggtgc ccgg                                34

<210> SEQ ID NO 14
<211> LENGTH: 33
<212> TYPE: DNA
<213> ORGANISM: Artificial Sequence
<220> FEATURE:
<223> OTHER INFORMATION: Synthetic DNA

<400> SEQUENCE: 14
gcggtcattg gtgaggacat caagctctac gcg                                 33

<210> SEQ ID NO 15
<211> LENGTH: 33
<212> TYPE: DNA
<213> ORGANISM: Artificial Sequence
<220> FEATURE:
<223> OTHER INFORMATION: Synthetic DNA

<400> SEQUENCE: 15
gcggtcattg gtgagtggat caagctctac gcg                                 33

<210> SEQ ID NO 16
<211> LENGTH: 33
<212> TYPE: DNA
<213> ORGANISM: Artificial Sequence
<220> FEATURE:
<223> OTHER INFORMATION: Synthetic DNA

<400> SEQUENCE: 16
gcggtcattg gtgagtacat caagctctac gcg                                 33

<210> SEQ ID NO 17
<211> LENGTH: 33
```

<210> SEQ ID NO 17
<211> LENGTH: 33
<212> TYPE: DNA
<213> ORGANISM: Artificial Sequence
<220> FEATURE:
<223> OTHER INFORMATION: Synthetic DNA

<400> SEQUENCE: 17
gcggtcattg gtgaggggat caagctctac gcg          33

<210> SEQ ID NO 18
<211> LENGTH: 33
<212> TYPE: DNA
<213> ORGANISM: Artificial Sequence
<220> FEATURE:
<223> OTHER INFORMATION: Synthetic DNA

<400> SEQUENCE: 18
gcggtcattg gtgagaagat caagctctac gcg          33

<210> SEQ ID NO 19
<211> LENGTH: 34
<212> TYPE: DNA
<213> ORGANISM: Artificial Sequence
<220> FEATURE:
<223> OTHER INFORMATION: Synthetic DNA

<400> SEQUENCE: 19
gacggcgcca tccgcgctgt cgccagtttt ggag         34

<210> SEQ ID NO 20
<211> LENGTH: 33
<212> TYPE: DNA
<213> ORGANISM: Artificial Sequence
<220> FEATURE:
<223> OTHER INFORMATION: Synthetic DNA

<400> SEQUENCE: 20
gcggtcattg gtgaggagat caagctctac gcg          33

<210> SEQ ID NO 21
<211> LENGTH: 33
<212> TYPE: DNA
<213> ORGANISM: Artificial Sequence
<220> FEATURE:
<223> OTHER INFORMATION: Synthetic DNA

<400> SEQUENCE: 21
gcggtcattg gtgagcacat caagctctac gcg          33

<210> SEQ ID NO 22
<211> LENGTH: 33
<212> TYPE: DNA
<213> ORGANISM: Artificial Sequence
<220> FEATURE:
<223> OTHER INFORMATION: Synthetic DNA

<400> SEQUENCE: 22
gcggtcattg gtgaggtgat caagctctac gcg          33

<210> SEQ ID NO 23
<211> LENGTH: 248
<212> TYPE: PRT
<213> ORGANISM: Pseudomonas coronafaciens

<400> SEQUENCE: 23

Met Lys Cys His Ser Val Ile Trp Phe Ser Ala Trp Pro His Pro Ile
 1               5                  10                  15

```
Ile Ser Arg Glu Lys Ser His Met Thr Ile Gly Phe Arg Val Leu Ser
            20                  25                  30

Ala Ala Arg Lys Val Ser Pro Glu Trp Val Ala Arg Tyr Arg Asp Val
        35                  40                  45

Pro Val Ala Asn Val Ser Asp Ser Met Asn Arg Met Thr Ala Gly Gly
    50                  55                  60

Ser Arg Leu Arg Pro Met His Arg Ala Gly Val Leu Ala Gly Pro Ala
65                  70                  75                  80

Leu Thr Val Lys Ala Arg Pro Gly Asp Asn Leu Met Leu His Tyr Ala
                85                  90                  95

Ile Asp Ile Ala Gln Pro Gly Asp Val Ile Val Asp Ala Gly Gly
            100                 105                 110

Asp Leu Thr Asn Ala Leu Ile Gly Glu Met Met Val Ala Tyr Ala Val
        115                 120                 125

Lys Arg Gly Val Ala Gly Ile Val Ile Asn Gly Ala Ile Arg Asp Ala
130                 135                 140

Ala Ser Ile Gly Ala Gly Asp Phe Pro Met Phe Ala Ala Gly Val Ser
145                 150                 155                 160

His Arg Gly Pro Tyr Lys Asp Gly Pro Gly Glu Ile Asn Val Pro Ile
                165                 170                 175

Ala Ile Asp Gly Met Val Ile Glu Ala Gly Asp Leu Val Ile Gly Asp
            180                 185                 190

Asp Asp Gly Leu Leu Cys Val Pro Tyr Asp Gln Val Ala Glu Val Tyr
        195                 200                 205

Asp Arg Ala Ala Ala Lys His His Ala Glu Gln Lys Gln Leu Glu Gln
    210                 215                 220

Ile Ala Lys Gly Glu Asn Asp Arg Ser Trp Val Leu Glu Ser Leu Lys
225                 230                 235                 240

Lys Lys Gly Cys Gln Leu Pro Glu
                245

<210> SEQ ID NO 24
<211> LENGTH: 230
<212> TYPE: PRT
<213> ORGANISM: Arthrobacter keyseri

<400> SEQUENCE: 24

Met Arg Leu Asn Asn Leu Gly Ile Val Arg Thr Asn Ile Glu Arg Pro
1               5                   10                  15

Asp Pro Ala Asp Val Lys Arg Leu Ser Gln Phe Gly Val Ala Thr Ile
            20                  25                  30

His Glu Ala Met Gly Arg Val Gly Leu Leu Arg Pro Tyr Ile Arg Pro
        35                  40                  45

Ala Tyr Thr Gly Ala Lys Leu Cys Gly Pro Ala Val Thr Val Leu Leu
    50                  55                  60

Gln Pro Gly Asp Asn Trp Met Phe His Val Ala Ala Glu Gln Val Gln
65                  70                  75                  80

Glu Gly Asp Val Ile Val Ala Gly Cys Thr Thr Glu Ser Glu Asp Gly
                85                  90                  95

Phe Phe Gly Glu Leu Leu Ala Thr Ser Leu Thr Ala Arg Gly Cys Lys
            100                 105                 110

Gly Leu Val Ile Asp Gly Gly Val Arg Asp Val Ala Asp Leu Glu Lys
        115                 120                 125

Met Asp Phe Pro Val Phe Ser Arg Ala Val Asn Ala Lys Gly Thr Val
```

-continued

```
            130                 135                 140
Lys Ala Thr Leu Gly Ser Val Asn Ile Pro Val Val Ala Asn Ala
145                 150                 155                 160

Val Val Asn Pro Gly Asp Val Val Ala Asp Val Asp Gly Val Val
                165                 170                 175

Val Val Pro Arg Glu Leu Val Gly Ala Val Ala Asp Ala Ser Gln Lys
            180                 185                 190

Arg Glu Asp Asn Glu Glu Ala Lys Arg Val Lys Phe Arg Glu Gly Val
                195                 200                 205

Leu Gly Leu Asp Val Tyr Gly Met Arg Gly Pro Leu Ala Lys Ala Gly
210                 215                 220

Leu Glu Tyr Val Glu Asn
225                 230

<210> SEQ ID NO 25
<211> LENGTH: 227
<212> TYPE: PRT
<213> ORGANISM: Pseudomonas ochraceae

<400> SEQUENCE: 25

Met Tyr Glu Leu Gly Val Val Tyr Arg Asn Ile Gln Arg Ala Asp Arg
1               5                   10                  15

Ala Ala Ala Asp Gly Leu Ala Ala Leu Gly Ser Ala Thr Val His Glu
                20                  25                  30

Ala Met Gly Arg Val Gly Leu Leu Lys Pro Tyr Met Arg Pro Ile Tyr
            35                  40                  45

Ala Gly Lys Gln Val Ser Gly Thr Ala Val Thr Val Leu Leu Gln Pro
        50                  55                  60

Gly Asp Asn Trp Met Met His Val Ala Ala Glu Gln Ile Gln Pro Gly
65                  70                  75                  80

Asp Ile Val Val Ala Ala Val Thr Ala Glu Cys Thr Asp Gly Tyr Phe
                85                  90                  95

Gly Asp Leu Leu Ala Thr Ser Phe Gln Ala Arg Gly Ala Arg Ala Leu
            100                 105                 110

Ile Ile Asp Ala Gly Val Arg Asp Val Lys Thr Leu Gln Glu Met Asp
        115                 120                 125

Phe Pro Val Trp Ser Lys Ala Ile Ser Ser Lys Gly Thr Ile Lys Ala
130                 135                 140

Thr Leu Gly Ser Val Asn Ile Pro Ile Val Cys Ala Gly Met Leu Val
145                 150                 155                 160

Thr Pro Gly Asp Val Ile Val Ala Asp Asp Gly Val Val Cys Val
                165                 170                 175

Pro Ala Ala Arg Ala Val Glu Val Leu Ala Ala Gln Lys Arg Glu
            180                 185                 190

Ser Phe Glu Gly Glu Lys Arg Ala Lys Leu Ala Ser Gly Val Leu Gly
        195                 200                 205

Leu Asp Met Tyr Lys Met Arg Glu Pro Leu Glu Lys Ala Gly Leu Lys
            210                 215                 220

Tyr Ile Asp
225
```

         *  *    *  ** *    * * **  *   *    *  **    *     *  * ****** *

VARIANT ALDOLASE AND PROCESSES FOR PRODUCING AN OPTICALLY ACTIVE IHOG AND AN OPTICALLY ACTIVE MONATIN USING THE SAME

CROSS-REFERENCE TO RELATED APPLICATIONS

The present application claims priority to JP 2004-075256, filed on Mar. 16, 2004, which is hereby incorporated by reference in its entirety.

BACKGROUND OF THE INVENTION

1. Field of the Invention

The present invention provides a variant aldolase that selectively produces a (4R)- or (4S)-isomer of a monatin precursor, 4-(indol-3-ylmethyl)-4-hydroxy-2-oxoglutaric acid. The present invention also provides a process for producing an optically active IHOG as well as a process for producing an optically active monatin using the same.

2. Discussion of the Background 4-(Indol-3-ylmethyl)-4-hydroxy-glutamic acid (3-(1-amino-1,3-dicarboxy-3-hydroxy-butan-4-yl)-indole) (hereinafter referred to as "monatin") represented by the formula shown below is a compound having a very strong sweetness, which is contained in the root of a plant *Schlerochitom ilicifolius*. Monatin is particularly expected to be a low-calorie sweetening agent (see JP-A 64-25757/1989).

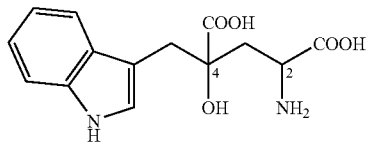

4-(Indol-3-ylmethyl)-4-hydroxy-glutamic acid

Monatin has two asymmetric centers (positions 2 and 4), and it has been reported that the naturally occurring stereoisomer is a (2S,4S)-isomer. In addition, it has been confirmed there are three additional stereo-isomers, each of which has been shown to be several ten to several thousand times as sweet as sucrose (see Table 1).

TABLE 1

Sweetness of the respective isomers of monatin

| Optical isomer | Sweetness (compared to sucrose) |
| --- | --- |
| 2R,4R | 2700-fold |
| 2R,4S | 1300-fold |
| 2S,4R | 300-fold |
| 2S,4S | 50-fold |

As indicated in Table 1, any stereo-isomers other than (2S,4S)-monatin has a high degree of sweetness. Particularly notable is the sweetness of (2R,4R)-monatin which is 2700 times as high as sucrose. Accordingly, this compound is particularly attractive as a sweetening agent or a sweetening component (sweetener). Therefore, it is desirable to develop a process for efficiently producing (2R,4R)-monatin.

The present inventors have developed a novel process for synthesizing monatin which comprises the following reactions (a) and (b) using indolepyruvic acid and pyruvic acid, both of which are commercially available as chemical reagents (WO 03/056026).

(a) synthesizing a precursor keto acid (4-(indol-3-ylmethyl)-4-hydroxy-2-oxoglutaric acid: IHOG) by aldol condensation of indolepyruvic acid with pyruvic acid (or oxalacetic acid);

(b) amination of IHOG at the position 2.

A method of monatin production can be summarized by the following reaction scheme:

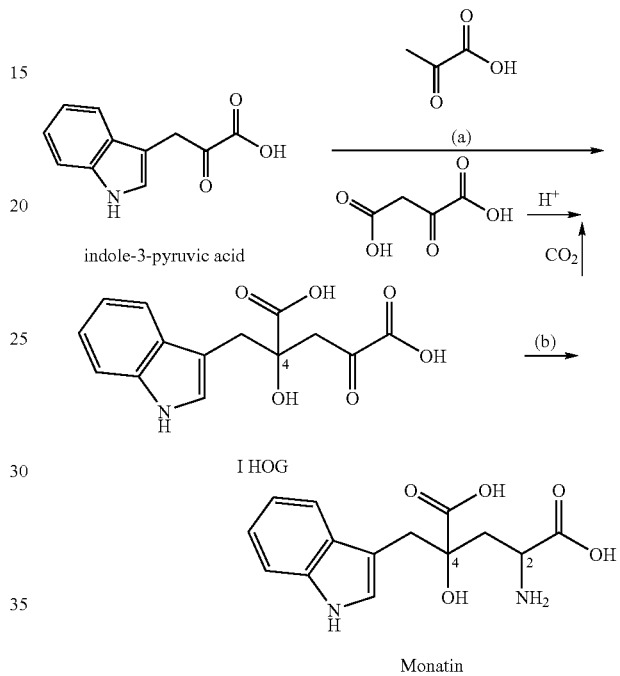

WO 03/056026 discloses aldolases derived from *Pseudomonas taetrolens* and *Psudomonas coronafaciens* as enzymes that can catalyze production of a keto acid (IHOG) precursor from indole-pyruvic acid and pyruvic acid (or oxalacetic acid) by an aldol condensation reaction in the abovementioned synthetic route of monatin (a). These aldolases have been known to catalyze the reaction yielding such a keto acid as 4-phenylmethyl-4-hydroxy-2-oxoglutaric acid (PHOG) in addition to IHOG.

There are two isomers in IHOG, i.e., 4R-isomer and 4S-isomer. In order to produce the sweetest isomer, (2R,4R)-monatin efficiently, it is desired that 4R-IHOG is preferentially prepared, i.e. to yield a 4R-rich IHOG product in the aldol condensation reaction (a) in the above-mentioned synthetic route for monatin. In many cases, chiral molecules have different physiological activities in their respective isomers, and there is a possibility that IHOGs have different properties in their respective isomers, accordingly. Thus, it is considered that the 4R-isomer and 4S-isomer separately provided can be applied to other uses than the precursor for monatin. Therefore, it is industrially very important to develop a process for producing predominantly one of the isomers, 4R-IHOG and 4S-IHOG.

In the conventional chemical synthetic system, however, the product IHOG was a mixture of 4R-isomer and 4S-isomer (racemate). In addition, though the present inventors have isolated an aldolase from *Pseudomonas taetrolens* suitable for the synthesis of IHOG, it has been elucidated that the IHOG produced by a wild-type of aldolase is not rich in the 4R-isomer, but the IHOG relatively rich in the 4S-isomer is produced depending on the reaction condition. (WO 03/056026 and WO 04/018672). There is no report on aldolase predominantly producing 4R-IHOG. At present, accordingly, a process for producing efficiently an optically active IHOG, particularly 4R-rich IHOG, has not yet been established.

The present invention was made in this situation for the purpose of providing a variant aldolase, which selectively produces the 4R-isomer and 4S-isomer of IHOG or PHOG as well as a process for producing an optically active IHOG and a process for producing an optically active monatin using the variant aldolase.

SUMMARY OF THE INVENTION

It is an object of the present invention to provide to solve the aforementioned problems and to provide variant aldolases that selectively produces the 4R-isomer and 4S-isomer of IHOG or PHOG as well as a process for producing an optically active IHOG and a process for producing an optically active monatin using the variant aldolase The present inventors worked assiduously to solve the above-mentioned problems, and as a result they found that an aldolase derived from *Pseudomonas taetrolens* ATCC4683 (PtALD) has sites involved in the recognition of chirality at the position 4 of the product (IHOG, PHOG) in the proximity of the active center of PTALD based on the PTALD structural information obtained by X-ray crystallography. They further found that the substitution of an amino acid residue at a particular position gives an aldolase in which optical selectivity is improved. Thus, they thought of the present invention. That is, the present invention is characterized in that the variant aldolase has been improved so that it produces predominantly one of the 4R-isomer and 4S-isomer. In this specification, "optical selectivity" is referred to the property of producing an optically active product by generating predominantly one of the 4R-isomer and 4S-isomer. Thus, the "selectivity for 4R-isomer" means the property of generating predominantly the 4R-isomer, and the "selectivity for 4S-isomer" does the property of generating predominantly the 4R-isomer.

Further the present inventors also found from information of the PtALD structure obtained by X-ray crystallography that other aldolases belonging to the same enzyme family as PtALD can be modified by homologous amino acid variation into variant aldolases which are able to generate IHOG optically selectively.

Thus, the invention is as follows.

[1] A protein having an aldolase activity which catalyzes at least one of the following aldol condensation reactions, one in which indole-3-pyruvic acid is allowed to react with pyruvic acid to yield 4-(indol-3-ylmethyl)-4-hydroxy-2-oxoglutaric acid having an optical activity due to the 4-asymmetric carbon, and the other in which phenylpyruvic acid is allowed to react with pyruvic acid to yield 4-phenylmethyl-4-hydroxy-2-oxoglutaric acid having an optical activity due to the 4-asymmetric carbon, wherein in the amino acid sequence of the above-mentioned protein, when the three-dimensional structure is aligned by the Threading method on an aldolase derived from *Pseudomonas taetrolens* having the amino acid sequence of SEQ ID NO: 2 as a template protein, at least one of the amino acid residues corresponding to the 37rd arginine residue and the 99th leucine residue on the above-mentioned template protein is substituted by a different amino acid residue from that of the above-mentioned template protein, and the homology score of the amino acid sequence of the above-mentioned protein shows the SeqFold Total Score (bit) of 100 or more as compared to the above-mentioned template protein.

[2] A protein, wherein when the three-dimensional structure of the protein as described in [1] is superimposed on that of the above-mentioned template protein, the deviation of the backbone Cα atom position is 4 angstrom or less as a root mean square error between the amino acid residues locating at the positions 37, 67, 71, 97, 98, 99, 100, 119, 120, 139, 141, 189, 192, 193, and 209 constituting the substrate-binding sites of the above-mentioned template protein and the amino acid residues of the protein corresponding to the above-mentioned substrate-binding sites of the template protein.

[3] A protein as described in [1], wherein in the amino acid sequence of the above-mentioned protein, when the three-dimensional structure is aligned by the Threading method on the above-mentioned template protein, at least one of the amino acid residues corresponding to the amino acid residues locating at the positions 67, 71, 97, 98, 100, 119, 139, 141, 189, 192, 193, and 209 of the above-mentioned template protein is substituted by a different amino acid residue from that of the above-mentioned template protein.

[4] A protein as described in [1] which comprises the following amino acid sequences (A) or (B):

(A) in the amino acid sequence of SEQ ID NO: 2, an amino acid sequence substituted by at least one amino acid residue selected from the following items (a) and (b):

(a) substitution of another amino acid residue for the 37th arginine residue;

(c) substitution of another amino acid residue for the 99th leucine residue;

(B) in the amino acid sequence of (A), an amino acid sequence having the substitution, deletion, insertion, addition and/or inversion of one or several amino acid residues at the positions other than 37, 67, 71, 97, 98, 99, 100, 119, 120, 139, 141, 189, 192, 193, and 209.

[5] A protein as described in [4] in which the substitution of the above-mentioned item (a) comprises substitution of the following item (a'):

(a') substitution of a tyrosine, tryptophan, histidine, phenylalanine or proline residue for the 37th arginine residue.

[6] A protein as described in [4] in which the substitution of the above-mentioned item (b) comprises substitution of the following item (b'):

(b') substitution of a aspartic acid, glutamic acid, lysine, tryptophan, tyrosine or glycine residue for the 99th leucine residue.

[7] A protein as described in any one of [1] to [6], which is characterized by having an aldolase activity which catalyzes at least one of the following aldol condensation reactions, one in which indole-3-pyruvic acid is allowed to react with pyruvic acid to yield predominantly the 4R-isomer of 4-(indol-3-ylmethyl)-4-hydroxy-2-oxoglutaric acid, and the other in which phenylpyruvic acid is allowed to react with pyruvic acid to yield predominantly the 4R-isomer of 4-phenylmethyl-4-hydroxy-2-oxoglutaric acid.

[8] A protein as described in any one of [1] to [6], which is characterized by having an aldolase activity which catalyzes at least one of the following aldol condensation reactions, one in which indole-3-pyruvic acid is allowed to react with pyruvic acid to yield predominantly the 4S-isomer of 4-(indol-3-ylmethyl)-4-hydroxy-2-oxoglutaric acid, and the other in which phenylpyruvic acid is allowed to react with pyruvic acid to yield predominantly the 4S-isomer of 4-phenylmethyl-4-hydroxy-2-oxoglutaric acid.

[9] A polynucleotide coding for the protein as described in any one of [1] to [8].

[10] A recombinant DNA comprising a polynucleotide as described in [9].

[11] A microorganism containing a recombinant DNA as described in [10].

[12] A process for producing an optically active 4-(indol-3-ylmethyl)-4-hydroxy-2-oxoglutaric acid which comprises making a protein as described in any one of [1] to [8] or a microorganism containing the same act on indole-3-pyruvic acid and pyruvic acid or oxalacetic acid to yield an optically active 4-(indol-3-ylmethyl)-4-hydroxy-2-oxoglutaric acid and recovering the resulting optically active 4-(indol-3-ylmethyl)-4-hydroxy-2-oxoglutaric acid.

[13] A process for producing the 4R-4-(indol-3-ylmethyl)-4-hydroxy-2-oxoglutaric acid which comprises making a protein as described in [7] or a microorganism containing the same act on indole-3-pyruvic acid and pyruvic acid or oxalacetic acid to yield predominantly the 4R-isomer of 4-(indol-3-ylmethyl)-4-hydroxy-2-oxoglutaric acid and recovering the resulting 4R-4-(indol-3-ylmethyl)-4-hydroxy-2-oxoglutaric acid.

[14] A process for producing the 4S-4-(indol-3-ylmethyl)-4-hydroxy-2-oxoglutaric acid which comprises making a protein as described in [8] or a microorganism containing the same act on indole-3-pyruvic acid and pyruvic acid or oxalacetic acid to yield predominantly the 4S-isomer of 4-(indol-3-ylmethyl)-4-hydroxy-2-oxoglutaric acid and recovering the resulting 4S-4-(indol-3-ylmethyl)-4-hydroxy-2-oxoglutaric acid.

[15] A process for producing 4R-monatin which comprises making a protein as described in [7] or a microorganism containing the same act on indole-3-pyruvic acid and pyruvic acid or oxalacetic acid to yield predominantly the 4R-isomer of 4-(indol-3-ylmethyl)-4-hydroxy-2-oxoglutaric acid (1st step), and aminating the 4R-isomer of 4-(indol-3-ylmethyl)-4-hydroxy-2-oxoglutaric acid obtained in the 1st step to yield 4R-monatin, followed by recovering the resulting 4R-monatin (2nd step).

[16] A process for producing 4R-monatin as described in [15], wherein (2R,4R)-monatin is predominantly produced in the above-mentioned 2nd step.

[17] A process for producing 4R-monatin as described in [15] or [16], wherein 4-(indol-3-ylmethyl)-4-hydroxy-2-oxoglutaric acid is aminated with action of an enzyme in the above-mentioned 2nd step.

[18] A process for producing 4R-monatin which comprises making a protein as described in [7] or a microorganism containing the same act on indole-3-pyruvic acid and pyruvic acid or oxalacetic acid to yield predominantly the 4R-isomer of 4-(indol-3-ylmethyl)-4-hydroxy-2-oxoglutaric acid, obtaining a reaction mixture containing 4-(indol-3-ylmethyl)-4-hydroxy-2-oxoglutaric acid (1st step);

reacting 4-(indol-3-ylmethyl)-4-hydroxy-2-oxoglutaric acid contained in the above-mentioned reaction mixture with an amine compound of the general formula (1):

H$_2$N—OR  (1)

(in the above-mentioned general formula (1), R represents a hydrogen atom, alkyl group, aryl group or aralkyl group)

or a salt thereof in a neutral or alkaline condition to yield 4-hydroxy-4-(3-indolylmethyl)-2-hydroxyiminoglutaric acid, and crystallizing the 4R-isomer of 4-hydroxy-4-(3-indolylmethyl)-2-hydroxyiminoglutaric acid or a salt thereof (2nd step); and reducing the resulting 4R-isomer of 4-hydroxy-4-(3-indolylmethyl)-2-hydroxyiminoglutaric acid or a salt thereof, followed by recovering the resulting 4R-monatin or a salt thereof (3rd step).

[19] A process for producing 4R-monatin as described in [18], wherein the amine compound represented by the general formula (1) is at least one selected from the group consisting of hydroxylamine, methoxyamine, and benzyloxyamine.

[20] A process for producing 4R-monatin as described in [18] or [19], wherein the reduction in the 3rd step is achieved in the presence of hydrogen and a hydrogenation catalyst.

[21] A process for producing 4R-monatin as described in any one of [18] to [20], wherein (2R,4R)-monatin is recovered by crystallization in the above-mentioned 3rd step.

[22] A process for producing 4R-monatin as described in any one of [18] to [21], wherein water, an alcohol solvent or aqueous alcohol solvent is used as a solvent for crystallization in the 2nd step.

[23] A process for producing 4S-monatin which comprises making a protein as described in [8] or a microorganism containing the same act on indole-3-pyruvic acid and pyruvic acid or oxalacetic acid to yield predominantly the 4S-isomer of 4-(indol-3-ylmethyl)-4-hydroxy-2-oxoglutaric acid (1st step), and aminating the 4S-isomer of 4-(indol-3-ylmethyl)-4-hydroxy-2-oxoglutaric acid obtained in the 1st step to yield 4S-monatin, followed by recovering the resulting 4S-monatin (2nd step).

[24] A process for preparing a variant aldolase by substituting a part of the amino acid residues of an aldolase active protein to yield a variant aldolase in which the aldolase activity is improved, which comprises introducing substitution, deletion, insertion, addition and/or inversion of an amino acid into at least one of the amino acid residues corresponding to those locating at the positions 37, 67, 71, 97, 98, 99, 100, 119, 139, 141, 189, 192, 193, and 209 in the above-mentioned template protein when the three-dimensional structure is aligned by the Threading method on an aldolase derived from *Pseudomonas taetrolens* having the amino acid sequence of SEQ ID NO: 2 in the amino acid sequence of the aldolase active protein as a template protein.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 9-1 shows an atomic coordinate (1) in the PtALD native crystals.

FIG. 9-2 shows an atomic coordinate (2) in the PtALD native crystals.

FIG. 9-3 shows an atomic coordinate (3) in the PtALD native crystals.

FIG. 9-4 shows an atomic coordinate (4) in the PtALD native crystals.

FIG. 9-5 shows an atomic coordinate (5) in the PtALD native crystals.

FIG. 9-6 shows an atomic coordinate (6) in the PtALD native crystals.

FIG. 9-7 shows an atomic coordinate (7) in the PtALD native crystals.

FIG. 9-8 shows an atomic coordinate (8) in the PtALD native crystals.

FIG. 9-9 shows an atomic coordinate (9) in the PtALD native crystals.

FIG. 9-10 shows an atomic coordinate (10) in the PtALD native crystals.

FIG. 9-11 shows an atomic coordinate (11) in the PtALD native crystals.

FIG. 9-12 shows an atomic coordinate (12) in the PtALD native crystals.

FIG. 9-13 shows an atomic coordinate (13) in the PtALD native crystals.

FIG. 9-14 shows an atomic coordinate (14) in the PtALD native crystals.

FIG. 9-15 shows an atomic coordinate (15) in the PtALD native crystals.

FIG. 9-16 shows an atomic coordinate (16) in the PtALD native crystals.

FIG. 9-17 shows an atomic coordinate (17) in the PtALD native crystals.

FIG. 9-18 shows an atomic coordinate (18) in the PtALD native crystals.

FIG. 9-19 shows an atomic coordinate (19) in the PtALD native crystals.

FIG. 9-20 shows an atomic coordinate (20) in the PtALD native crystals.

FIG. 9-21 shows an atomic coordinate (21) in the PtALD native crystals.

FIG. 9-22 shows an atomic coordinate (22) in the PtALD native crystals.

FIG. 9-23 shows an atomic coordinate (23) in the PtALD native crystals.

FIG. 9-24 shows an atomic coordinate (24) in the PtALD native crystals.

FIG. 9-25 shows an atomic coordinate (25) in the PtALD native crystals.

FIG. 9-26 shows an atomic coordinate (26) in the PtALD native crystals.

FIG. 10 shows a secondary structure assigned for the amino acid sequence of PtALD. The thick double line indicates α-helix and the thick single line does β-strand. In addition, the 2nd to 220th amino acid sequence of SEQ ID NO: 2, the three-dimensional structure of which has been determined is also shown.

FIG. 11 shows the result of performing the Threading method by a program SeqFold for the PtALD amino acid sequence.

FIG. 12 shows the result of performing the Threading method by a program SeqFold for the amino acid sequence of an aldolase derived from *Pseudomonas coronafaciens*.

FIG. 13 shows the result of performing the Threading method by a program SeqFold for the amino acid sequence of an aldolase derived from *Arthrobacter keyseri*.

FIG. 14 shows the result of performing the Threading method by a program SeqFold for the amino acid sequence of an aldolase derived from *Pseudomonas ochraceae*.

FIG. 15 shows the alignment of the amino acid sequences of PtALD and of an aldolase derived from *Pseudomonas coronafaciens* (residues 26-245 of SEQ ID NO: 23) aligned with PtALD (residues 3-220 of SEQ ID NO: 2). A part of the N-terminal and C-terminal sequences for which no alignment is made is not shown.

FIG. 16 shows the alignment of the amino acid sequences of PtALD and of an aldolase derived from *Arthrobacter keyseri* (residues 13-226 of SEQ ID NO: 24) aligned with PtALD (residues 3-220 of SEQ ID NO: 2). A part of the N-terminal and C-terminal sequences for which no alignment is made is not shown.

FIG. 17 shows the alignment of the amino acid sequences of PtALD and of an aldolase derived from *Pseudomonas ochraceae* (residues 4-224 of SEQ ID NO: 25) aligned with PtALD (residues 3-220 of SEQ ID NO: 2). A part of the N-terminal and C-terminal sequences for which no alignment is made is not shown.

DETAILED DESCRIPTION OF THE INVENTION

Figure 1:
FIG. 1 shows a ribbon model of the three-dimensional structure of a PtALD subunit in the native crystals.

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

By using the variant aldolase of the invention, an optically active IHOG can be produced from indolepyruvic acid and pyruvic acid (or oxalacetic acid), and amination of the resulting optically active IHOG yields an optically active monatin.

The variant aldolase of the invention first enables efficient introduction of asymmetry during an aldol condensation reaction, and one of 4R-IHOG and 4S-IHOG can be produced predominantly using an aldolase of the invention.

In the amination step (b) in the synthetic route for monatin, if the 4R-IHOG can be produced predominantly to reduce generation of the side-product 4S-IHOG in the aldol condensation reaction (a), the yield of (2R,4R)-monatin could be increased, since it is considered that 4S-IHOG might act competitively and inhibitively on 4R-IHOG when the reaction is conducted in the presence of an enzyme such as aminotransferase.

In the prior art, in order to separate the 4R-isomer from a racemic IHOG (4R,4S-IHOG), it was necessary to crystallize 4R-IHOG-oxime on the reaction with an chiral amine after oxime formation of 4R,4S-IHOG. According to the invention, however, since a 4R-rich IHOG can be produced at the step of an aldol condensation reaction, optical resolution with any chiral amine is not necessary during crystallization, and thus the 4R-IHOG-oxime can be crystallized in situ after the oxime formation. Therefore, the process for purification of 4R-IHOG can be reduced.

As mentioned above, PtALD is an aldolase isolated from *Pseudomonas taetrolens* ATCC4683 strain. The base sequence of a wild-type PtALD gene is shown in SEQ ID NO: 1 of Sequence Listing, and the amino acid sequence of the wild-type PtALD in SEQ ID NO: 2. SEQ ID NO: 2 of Sequence Listing corresponds to that of PtALD encoded by the base sequence of the base numbers 456 to 1118 among the base sequence described in SEQ ID NO: 1 of Sequence Listing. In this specification, the position of the PtALD amino acid residues is designated on the basis of the amino acid sequence described in SEQ ID NO: 2 of Sequence Listing.

According to the study by the present inventors, it has been found that PtALD can catalyze the aldol condensation reaction of indolepyruvic acid with pyruvic acid (or oxalacetic acid) to yield 4-(indol-3-ylmethyl)-4-hydroxy-2-oxoglutaric acid (IHOG), and the reaction of phenylpyruvic acid with pyruvic acid to yield 4-phenylmethyl-4-hydroxy-2-oxoglutaric acid (PHOG).

When IHOG is produced with a wild-type PTALD, there is a tendency to generate IHOG slightly rich in the S-isomer depending on the reaction condition. The production ratio of S-IHOG to R-IHOG cannot be determined unconditionally because it varies depending on the substrate concentration and other reaction conditions. For example, however, in a reaction condition in which 50 mM of indole-3-pyruvic acid and 250 mM of pyruvic acid are used as substrates, it has been confirmed that PtALD generates S-IHOG and R-IHOG in the ratio of about 65:35 (see Example 3).

When PHOG is produced with a wild-type PtALD, it has also been confirmed that the R-isomer and the S-isomer are generated in the ratio of approximately 50:50 (see Example 3).

In addition, the present inventors determined the three-dimensional structure of the wild-type PtALD to elucidate the amino acid residues constituting the active site of PtALD and to identify the amino acid residues involved in the recognition of chirality at the position 4 of the products (IHOG, PHOG). Thus, the inventors successfully obtained a variant aldolase by introducing a site-specific mutation into such an amino acid residue.

In addition, the inventors found from the analyzed PtALD structural information that other aldolases belonging to the same enzyme family as PtALD can be converted by homologous amino acid mutation into variant aldolases by which IHOG is generated optically selectively.

Hereinafter, the mode for carrying out the invention will be described according to the following items.
[I] Three-dimensional structure of a wild-type PtALDs
[II] Variant aldolases
(A) The amino acid sequences of variant aldolases
(B) Production of variant aldolases
[III] Production of an optically active IHOG
[IV] Production of an optically active monatin

[I] Three-Dimensional Structure of a Wild-Type PtALDs

The three-dimensional structure of proteins by X-ray crystallography is carried out according to the following procedures (1) to (3).

(1) Protein is crystallized. Crystallization is essential for determination of the three-dimensional structure, in addition, it is an industrially very useful technique for purification to obtain highly pure proteins, or dense and stable protein preservation resisting to proteases.

(2) X-Ray is irradiated to the prepared crystals to collect the diffraction data. In this stage, the protein crystals are sometimes damaged by X-ray irradiation to deteriorate diffraction capacity. In such a case, the crystals are rapidly cooled down to approximately −173° C., at which temperature the diffraction data is collected according to a recently widely distributed technique for measuring at lower temperatures. Finally, in order to collect the high resolution data to be utilized in structural determination, a synchrotron radiation of high luminance is utilized.

(3) In order to carry out the crystallography, phase information is required in addition to the diffraction data.

Since the crystal structure of proteins homologous to PtALD has not yet been known, the phase problem has to be solved by a heavy atom isomorphous replacement method. The heavy atom isomorphous replacement method comprises introducing a large atomic number metal atom such as mercury or platinum into crystal and utilizing contribution of a large X-ray scattering capacity of the metal atom to the X-ray diffraction data to obtain the phase information. Thus determined phase can be improved by smoothing the electron density of a solvent area in the crystal.

Since the water molecules contained in the solvent area fluctuate so largely that it cannot be observed, the electron density of this area can be approximated to 0 to approach the real electron density, resulting in improvement of the phase. A protein model is constructed to the electron density map calculated from this improved phase. This process can be achieved on a computer graphics using a computer program such as QUANTA (Accelrys Co., USA). Subsequently, the structure is refined with a program such as CNX (Accelrys Co.) to complete the structural analysis. Once the crystal (native crystal) structure of the protein per se is determined, the crystal structure of a complex between the protein and its substrate can relatively easily be determined by means of molecular replacement or a differential Fourier method utilizing the native crystal structure.

The present inventors performed crystallization using a large quantity of PtALD which was expressed in *Escherichia coli* and obtained crystals suitable for crystallography (Example 9). The crystals were applied to a heavy atom isomorphous replacement method for crystallography and succeeded in determining the three-dimensional structure of PtALD (Example 10). Further, crystallization was performed on the complex between PtALD and one of the aimed products, PHOG, or another product, i.e., IHOG homolog 4-hydroxy-4-(3-indolylmethyl)-2-hydroxyiminogluaric acid (IHOG-oxime) (Example 9). X-ray crystallography of these crystals was performed and their three-dimensional structures were determined (Examples 11 and 12).

FIG. 1 shows the three-dimensional structure of PtALD in the native crystal determined in the invention, represented by a ribbon model. In FIG. 1, the α-helix and β-sheet are indicated by a helically curled ribbon and an extended ribbon, respectively.

Figure 2:
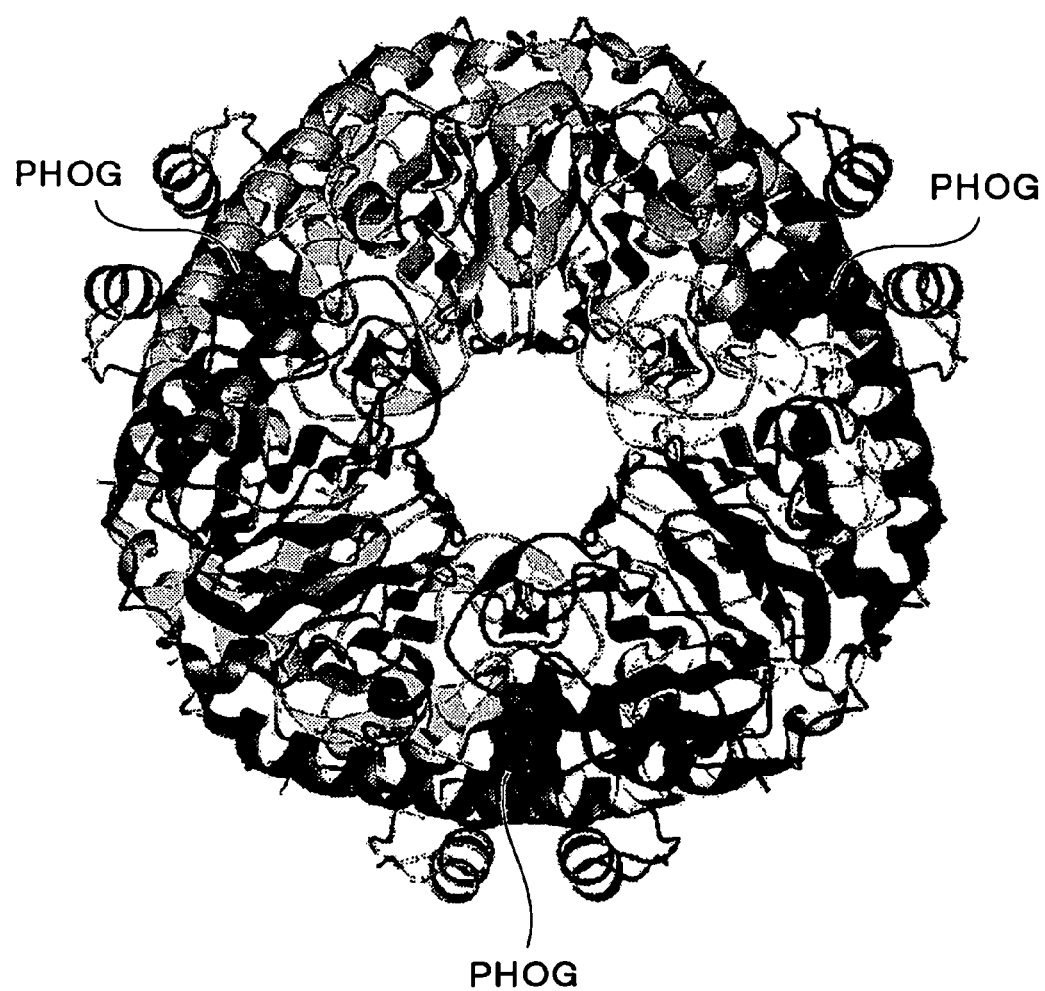
FIG. 2 shows the three-dimensional structure of the PtALD hexamer complexed with PHOG, wherein the PtALD molecule is represented by a ribbon model and the PHOG molecule by a space-filling model.
Figure 3:
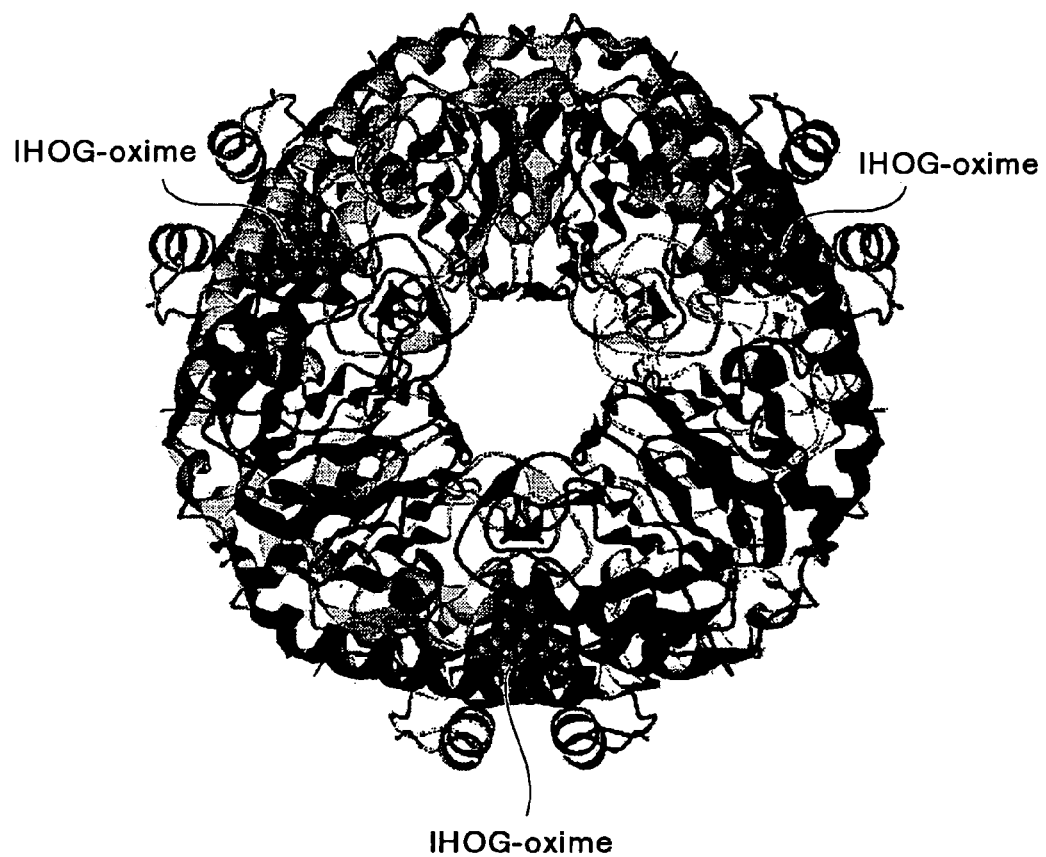
FIG. 3 shows the three-dimensional structure of the PtALD hexamer complexed with IHOG-oxime, wherein the PtALD molecule is represented by a ribbon model and the IHOG-oxime molecule by a space-filling model.
Figure 4:
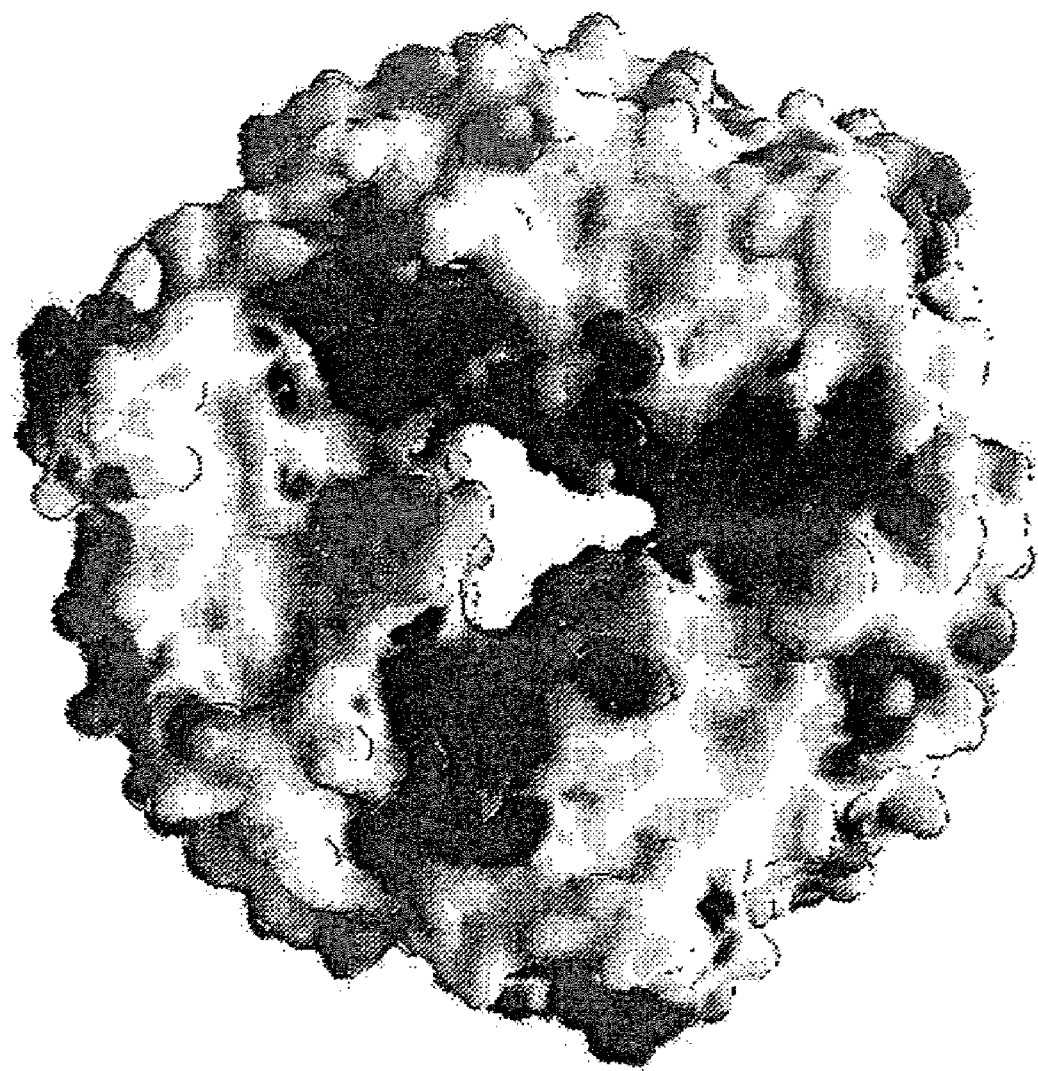
FIG. 4 shows the three-dimensional structure of the PtALD hexamer in the native crystals, wherein the hexamer is viewed from the same direction as in FIG. 2.

The monomolecular part of PtALD, as shown in FIG. 1, exhibits a form similar to a comma-shaped ornamental scent bag, in which the N-terminal end forms the head of the bag and the C-terminal end forms the tail. Practically, 6 monomolecular parts as subunits gather to form a hexamer, which functions as an aldolase. FIGS. 2 and 3 show hexamer ribbon models in the crystal structure of PHOG complex and that of IHOG-oxime complex. In both figures, space-filling models represent PHOG and IHOG-oxime, respectively. The hexamer of PtALD is in a cylindrical form of about 80 angstrom in diameter and about 75 angstrom in height. Two trimers comprised of subunits related by threefold rotation axis are associated with twofold rotation axis to form a hexamer. When one subunit in the trimer is defined as subunit A and the other in the same trimer as subunit B, the head portion of subunit A interacts with the tail portion of subunit B, at which interaction site PHOG and IHOG-oxime are binding. FIG. 4 shows a molecular surface of the hexamer in the native crystal structure of PtALD, observed from the direction of cylinder axis. The area having a charge is indicated by dark color and that having no charge by thin color.

Figure 5:
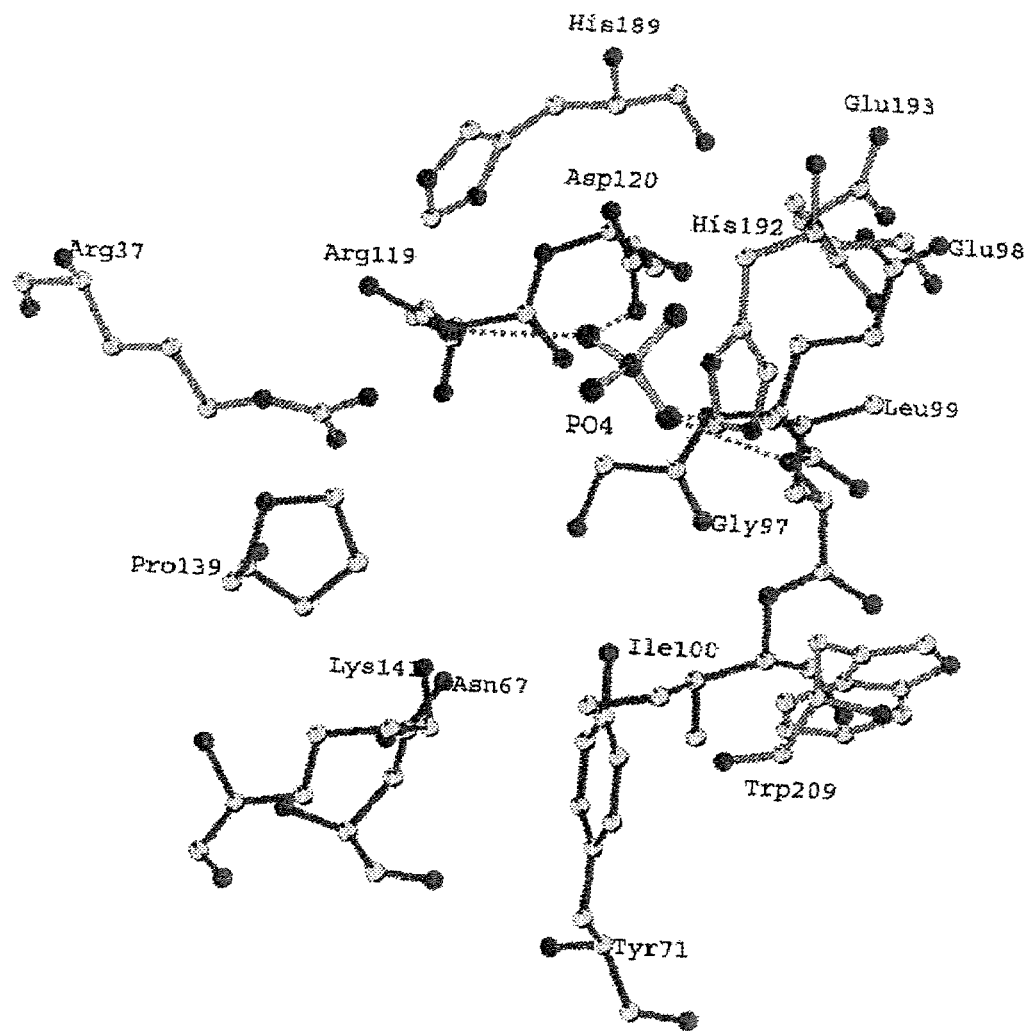
FIG. 5 shows the three-dimensional structure near the active site of PtALD in the native crystals, represented by a ball-and-stick model. The bond of the binding phosphate ion is represented as a relatively thick stick. The interaction of hydrogen bond or salt bridge is indicated by a dotted line.
Figure 6:
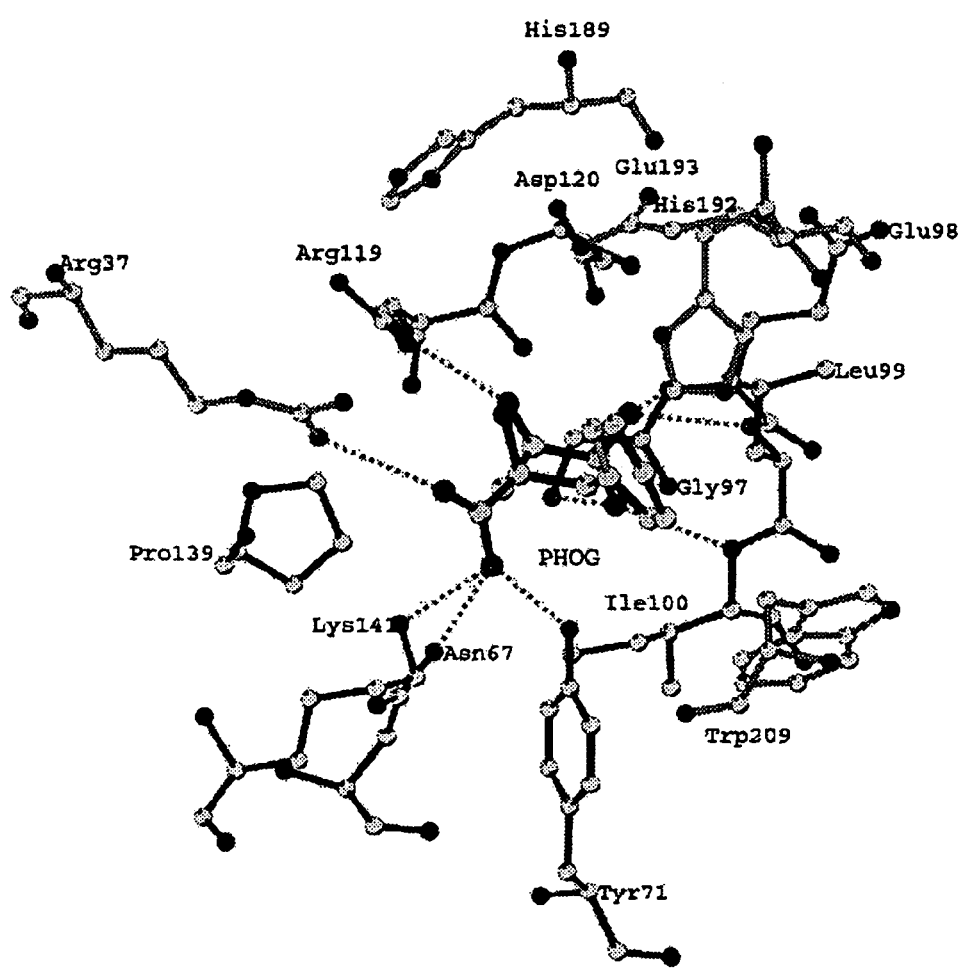
FIG. 6 shows the three-dimensional structure near the active site of PtALD in the crystal of a PtALD-PHOG complex, represented by a ball-and-stick model. The bond of the binding PHOG molecule is represented as a relatively thick stick. The interaction of hydrogen bond or salt bridge is indicated by a dotted line.
Figure 7:
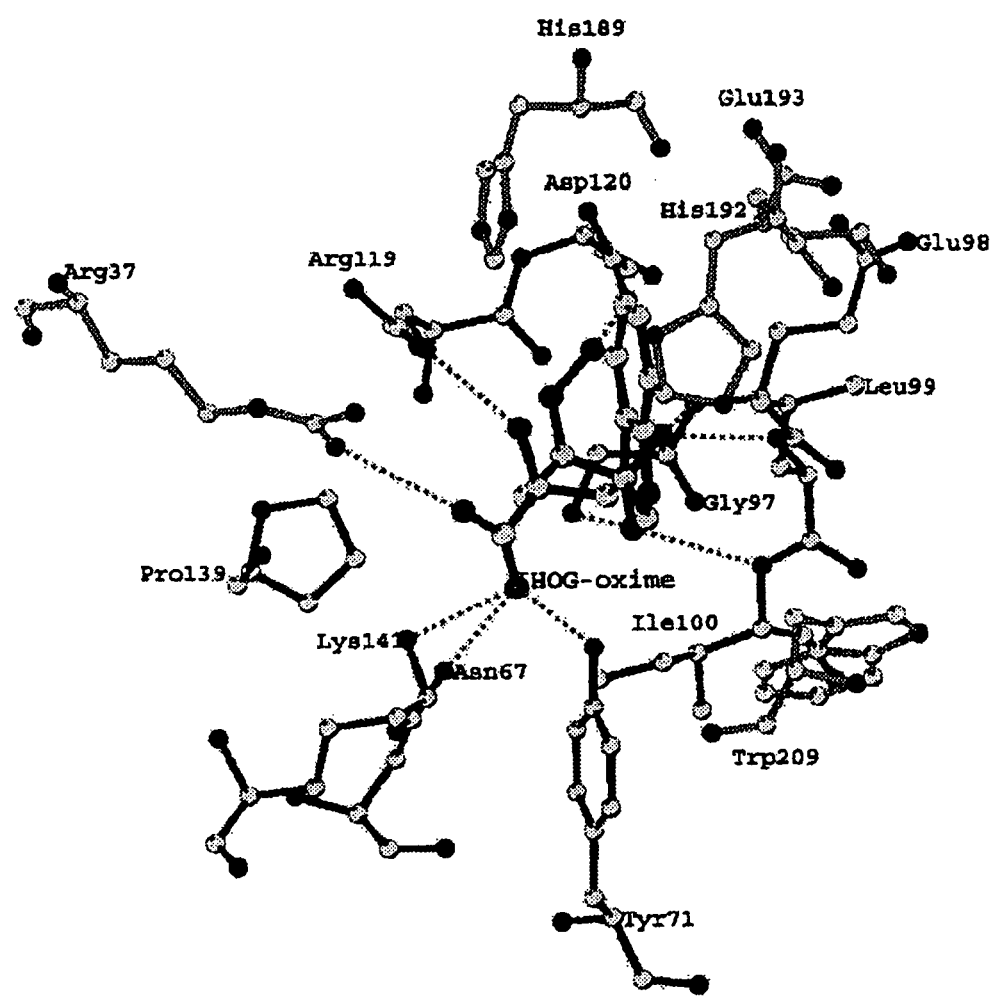
FIG. 7 shows the three-dimensional structure near the active site of PtALD in the crystal of a PtALD-IHOG-oxime complex, represented by a ball-and stick-model. The bond of the binding IHOG-oxime molecule is represented as a relatively thick stick. The interaction of hydrogen bond or salt bridge is indicated by a dotted line.

FIG. 5 to FIG. 7 show the enlarged surrounding areas of the binding sites of PHOG and IHOG-oxime in PtALD as ball and stick models. FIG. 5 shows the native crystal structure, FIG. 6 the crystal structure of PHOG complex, and FIG. 7 the crystal structure of IHOG-oxime complex, each showing the enlarged surrounding area of a substrate-binding site. In FIGS. 5 to 7, only 15 amino acid residues of the substrate-binding site in PtALD are represented. In FIG. 6, the 4R-isomer of PHOG binds to PtALD, and in FIG. 7, the 4R-isomer of IHOG-oxime binds to PtALD. In the native crystals, a phosphate ion that is used as a precipitant for crystallization binds to PtALD, and in the crystal structure of both complexes, 4R-PHOG and 4R-IHOG-oxime bind respectively to PtALD.

Within 4 angstrom of the area surrounding both molecules, there are 15 amino acid residues, i.e., Arg 37, Asn 67, Tyr 71, Gly 97, Glu 98, Leu 99, Ile 100, Arg 119, Asp 120, Pro 139, Lys 141, His 189, His 192, Glu 193, and Trp 209. Among them, 10 residues, i.e., Asn 67, Tyr 71, Gly 97, Glu 98, Leu 99, Ile 100, Arg 119, Asp 120, Pro 139, and Lys 141 are originally from the subunit A, and the remaining 5 residues (Arg 37, His 189, His 192, Glu 193, and Trp 209) are from the subunit B. Therefore, when the three-dimensional structure of a protein is superimposed on the above 15 amino acids constituting the substrate-constituting site, the protein in which the deviation of the backbone Cα atom position between the amino acids is within 4 angstrom or less as a root mean square error can reasonably be estimated to be an aldolase which has an activity binding to 4R-PHOG and 4R-IHOG-oxime similarly in PtALD. Among them, if Asp 120 is replaced with the other residue, the enzymatic activity sometimes might completely be lost (Example 3). Thus, it is preferred to avoid substitution of another amino acid at Asp 120.

The above-mentioned amino acid residues can capture PHOG or IHOG-oxime through hydrogen bond, electrostatic interaction (salt bridge), hydrophobic interaction, π-π interaction (interaction between the magnetic fields generated by the ring current on the aromatic rings), CH/π interaction (interaction between the magnetic fields generated by the ring current on the aromatic ring and the electron of methyl group), and the like. Therefore, it would be possible to create a variant enzyme by which the 4R-isomer or 4S-isomer of PHOG or IHOG is selectively produced as well as a variant enzyme in which the generation of PHOG and IHOG is improved, if the structure of the complexes is observed well and an appropriate improvement is made in designing for these amino acid residues.

For example, in the crystal structure of the complexes, one of the two oxygen atoms of 4-carboxyl group in 4R-PHOG or 4R-IHOG-oxime forms a hydrogen bond or salt bridge with the Nη1 atom of Arg 37, and the other does a hydrogen bond with Asn 67 Nδ, Tyr 71 Oη or Lys 141 Nζ (possibly salt bridge in a case of Lys 141 Nζ). It is also expected that, when the substrate phenylpyruvic acid or indolepyruvic acid binds at a configuration to generate an R-isomer as a product (pro-R-configuration), the carboxyl group may form the interaction with PtALD as mentioned above. On the contrary, when 4S-PHOG or 4S-IHOG binds, the situation between the 4-carboxyl group and hydroxyl group is reversed.

In such a case, it is considered that the interaction between the Nη1 atom of Arg 37 and the 4-carboxyl group is remaining unchanged, but the interaction between Asn 67 Nδ, Tyr 71 Oη or Lys 141 Nζ and the carboxyl group disappears. On the other hand, the oxygen atom of hydroxyl group is directed toward Asn 67 Nδ, Tyr 71 Oη or Lys 141 Nζ, but it cannot approach these residues as the oxygen atom of carboxyl group can do so, and accordingly it cannot form so highly polar interaction as hydrogen bond. It is considered that, when the substrate phenylpyruvic acid or indolepyruvic acid binds with the enzyme at a configuration to generate an S-isomer as a product (pro-S-configuration), the residue on the enzyme side involved in the interaction with the carboxyl group is Arg 37 alone. Therefore, if an improvement is made for the Arg 37 residue so that it is unable to have a hydrogen bond interaction with the carboxyl group of the substrate binding through a pro-S-configuration, it would become difficult to cause binding of the substrate at the same configuration. It is considered that the binding of the substrate through a pro-R-configuration has almost no influence on the generation of the 4R-isomer even though the interaction with the 37th residue disappears, since a strong interaction of the carboxyl group with Asn 67, Tyr 71 or Lys 141 can be maintained. As a result, it is possible to obtain an improved enzyme, which produces predominantly one of 4R-IHOG or 4R-PHOG.

In the proximity of the 4-carbon atom of 4R-PHOG and 4R-IHOG-oxime, there is Leu 99 near the just opposite position of Arg 37. Conversion of this amino acid into a charged amino acid may induce an electrostatic repulsion or abstraction between the carboxyl group of phenylpyruvic acid or indolepyruvic acid to make both substrates bind through a pro-R-configuration. Alternatively, it is also considered that a modification of the side-chain bulkiness of this amino acid possibly makes the surface shape of the substrate-binding site change so that both substrates bind through a pro-R-configuration.

Such modification is not limited to the two residues of Arg 37 and Leu 99, and thus, all of the amino acid residues surrounding PHOG or IHOG-oxime may be chosen as an object for introduction of variation. Since modification of Asp 120 having an important role for the activity is expected to make the activity lose, it is preferred to prepare a variant having no such modification.

[II] Variant Aldolase

The variant aldolase of the invention may be prepared by introducing a variation into a particular amino acid residue of a wild-type aldolase so that IHOG can optically selectively be produced.

As mentioned above, as a result of analysis of the information on the three-dimensional structure of PtALD, it was found that the binding site of the PtALD substrate is constituted by a space surrounded by 15 amino acid residues, i.e., Arg 37, Asn 67, Tyr 71, Gly 97, Glu 98, Leu 99, Ile 100, Arg 119, Asp 120, Pro 139, Lys 141, His 189, His 192, Glu 193, and Trp 209. That is, the space surrounded by these 15 amino acid residues makes an environment suitable for binding the substrates (indolepyruvic acid and pyruvic acid).

Thus, in the amino acid sequence of a wild-type aldolase, the activity of a wild-type aldolase can be improved by introducing a substitution, deletion, insertion, addition and/or inversion into any of the amino acid residues among those corresponding to the 15 amino acid residues constituting the substrate-binding site of PtALD, except Asp 120 which is considered to have an important action on the activity. The improvement of the aldolase activity as mentioned herein means the broad sense of improvement, such as improvement of selective production of the 4R- or 4S-isomer of PHOG or IHOG, improvement of the productivity of PHOG or IHOG, as well as improvement of the substrate specificity.

Among the 15 amino acid residues constituting the substrate-binding site of PtALD, the amino acid residues involved in the chirality of the position 4 of the product (IHOG and PHOG) include two amino acids, i.e., Arg 37 and Leu 99. The variant aldolases selectively generating the 4R- or 4S-isomer are useful in production of an optically active monatin. Hereinafter, explanation will be made mainly on such variant aldolases, accordingly.

(A) Amino Acid Sequence of a Variant Aldolase

In order to obtain an optically active variant aldolase, the site participating in chirality at the position 4 of the product may be identified in the amino acid sequence of a wild-type aldolase and the amino acid residue at the identified position may be replaced with another amino acid residue. A wild-type aldolase as an object into which a variation is introduced includes in addition to PTALD other aldolases having three-dimensional structure similar to that of PtALD. The amino acid sequences of variant aldolases will be explained (i) in a case in which PtALD is used as a wild-type aldolase and (ii) in a case in which other aldolases than PtALD are used, separately.

(i) A case of determining the amino acid sequence of a variant aldolase from PtALD PtALD is a protein having the amino acid sequence as described in SEQ ID NO: 2. In order to modify the optical selectivity of PtALD, at least one of Arg 37 and Leu 99 amino acid residues in the 221 amino acid residues described in SEQ ID NO: 2 of Sequence Listing may be introduced with a variation. That is, in the amino acid sequence as shown in SEQ ID NO: 2, at least one amino acid residue of the 37th arginine residue and 99th leucine residue may be replaced with another amino acid residue to give a variant aldolase having optical selectivity.

When a modification is made for Arg 37 so that a hydrogen bond interaction is specifically induced for the substrate carboxyl group through which phenylpyruvic acid or indolepyruvic acid binds in a pro-S-configuration, it may be possible to selectively generate 4S-PHOG or 4S-IHOG. On the other hand, when a modification is made for the substrate carboxyl group through which both substrates bind in a pro-S-configuration so that the hydrogen bond interaction is not induced, the substrates easily bind in the pro-R-configuration with relatively high frequency to give 4R-PHOG and 4R-IHOG, selectively. For example, the amino acid residue that disturbs binding of the substrate in a pro-S-configuration includes tyrosine residue, tryptophan residue, histidine residue, phenylalanine residue, proline residue, and the like.

When Lue 99 is converted into a charged amino acid, electrostatic abstraction or repulsion is induced to the carboxyl group of phenylpyruvic acid or indolepyruvic acid. Alternatively, it is also possible to vary the side-chain bulkiness of the amino acid residue to alter the surface shape of the substrate-binding site, so that both substrates bind easily in either pro-R-configuration or pro-S-configuration. For example, the amino acid residue which promotes binding of the substrate in a pro-R-configuration includes aspartic acid residue, glutamic acid residue, lysine residue, tryptophan residue, tyrosine residue, glycine residue, and the like.

Therefore, in order to obtain a 4R-selective variant aldolase, the 37th arginine residue in the amino acid sequence as shown in SEQ ID NO: 2 may preferably be replaced with a tyrosine residue, tryptophan residue, histidine residue, phenylalanine residue or proline residue. It is also preferred to introduce an aspartic acid residue, glutamic acid residue, lysine residue, tryptophan residue, tyrosine residue or glycine residue in place of the 99th leucine residue. In addition, it is also preferred to introduce these substitutions in place of both of the amino acid residues of the 37th arginine and 99th leucine residues.

In combination of the above-mentioned variant introduction into Arg 37 and Leu 99, the remaining amino acid residues except Asp 120, that is, at least one of Asn 67, Tyr 71, Gly 97, Glu 98, Ile 100, Arg 119, Pro 139, Lys 141, His 189, His 192, Glu 193, and Trp 209 may be altered by substitution, deletion, insertion, addition and/or inversion. Since these 12 amino acid residues constitute a substrate-binding site, it may be expected that productivity or substrate specificity of PHOG or IHOG may be modified by introducing a variation into these sites. When a variation is introduced into the above-mentioned 12 amino acid residues, however, it may be conducted within the range that the aldolase activity and optical selectivity obtained by the substitution of Arg 37 or Leu 99 by another amino acid residue will not be disturbed considerably.

In addition to the substitution of Arg 37 or Leu 99 by another amino acid residue, the portion other than the amino acid residues constituting the substrate-binding site, that is, the amino acid residues other than Arg 37, Asn 67, Tyr 71, Gly 97, Glu 98, Leu 99, Ile 100, Arg 119, Asp 120, Pro 139, Lys 141, His 189, His 192, Glu 193, and Trp 209 may be altered by substitution, deletion, insertion, addition and/or inversion; in such a case, when the aldolase activity and the optical selectivity obtained by the substitution of Arg 37 or Leu 99 by another amino acid residue is not disturbed considerably, such aldolases are included in the variant aldolases of the invention.

The term "one or several" as mentioned herein means the number within which range the three-dimensional whole structure of protein, the aldolase activity, and the optical selectivity obtained by the substitution of Arg 37 or Leu 99 by another amino acid residue is not disturbed considerably, and specifically includes 1 to 50, preferably 1 to 30, and more preferably 1 to 10 amino acids. In such a case, the aldolase activity in the protein having the amino acid sequence as described in SEQ ID NO: 2 of Sequence Listing, and variants thereof, is maintained in a condition of 33° C. and pH 9 by 1% or more, preferably 5% or more, more preferably 20% or more, even more preferably 50% or more, particularly preferably 70% or more, and especially preferably 100% or more.

Figure 8:
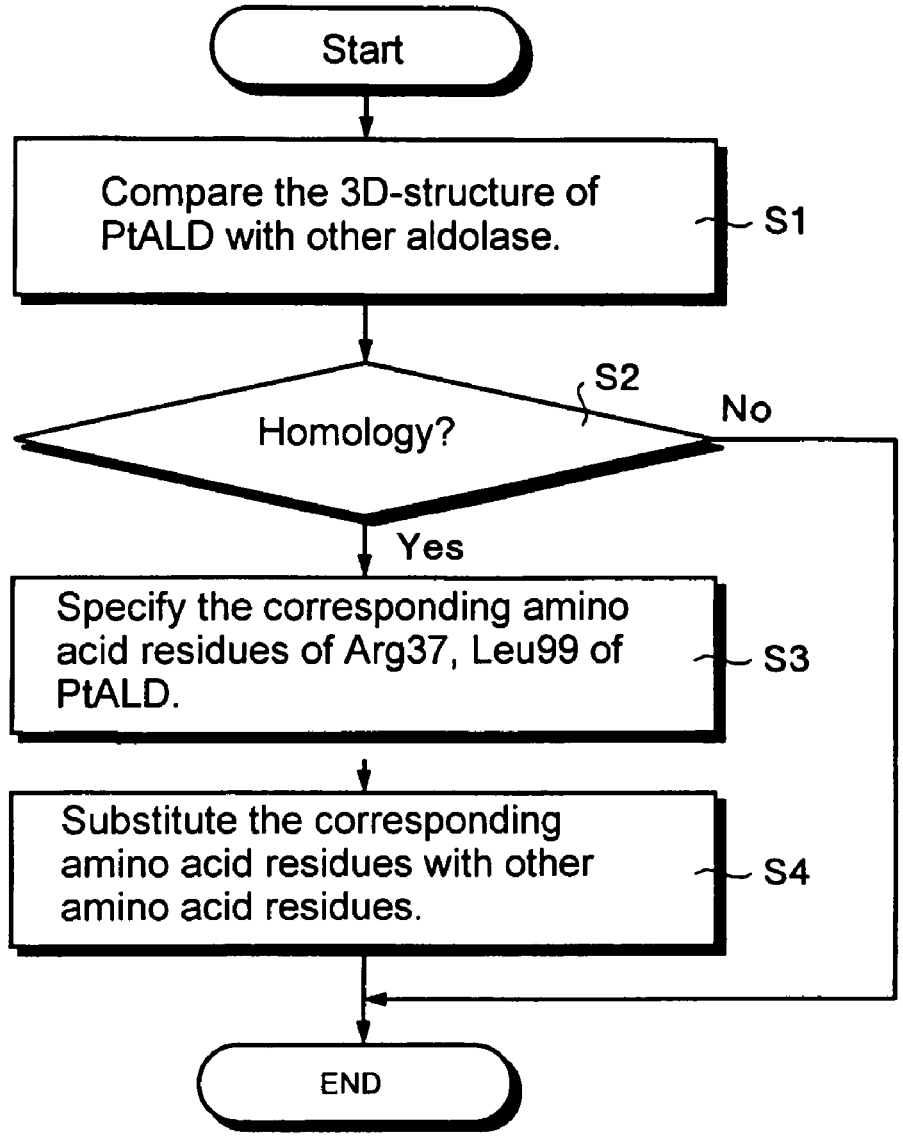
FIG. 8 shows a flow chart for determining the amino acid sequence of a variant aldolase using the other aldolase than PtALD.
Figure 11:
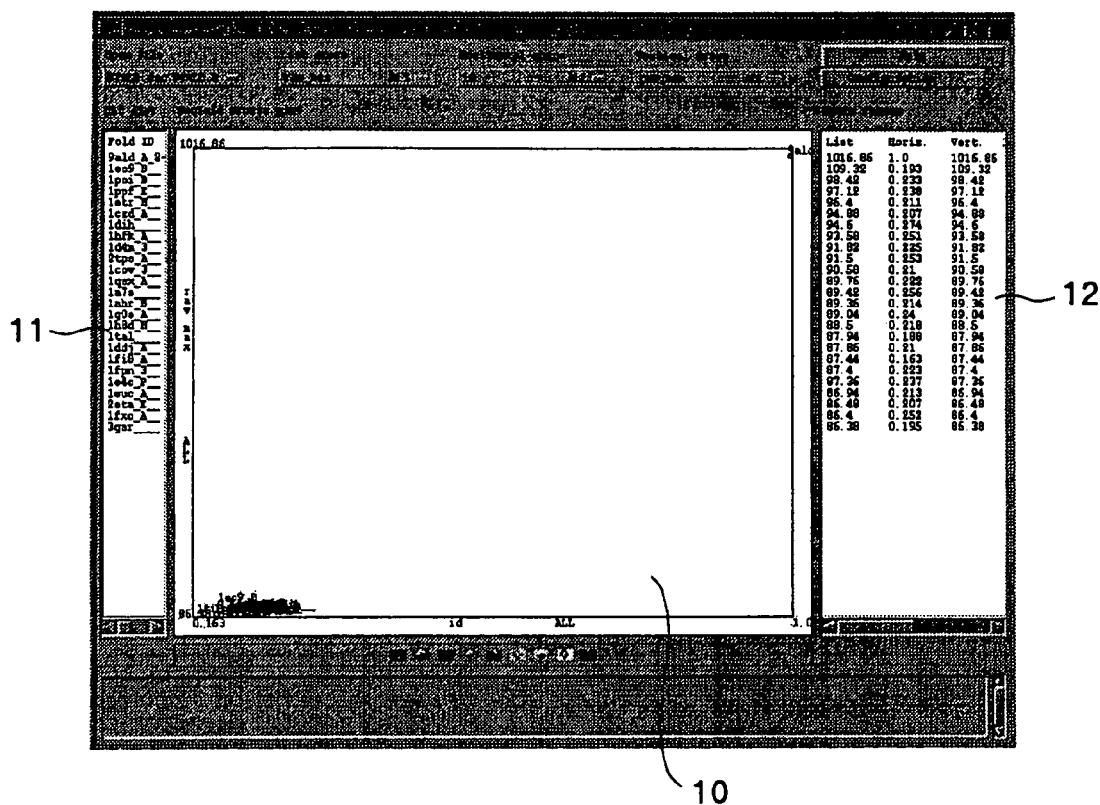
Figure 12:
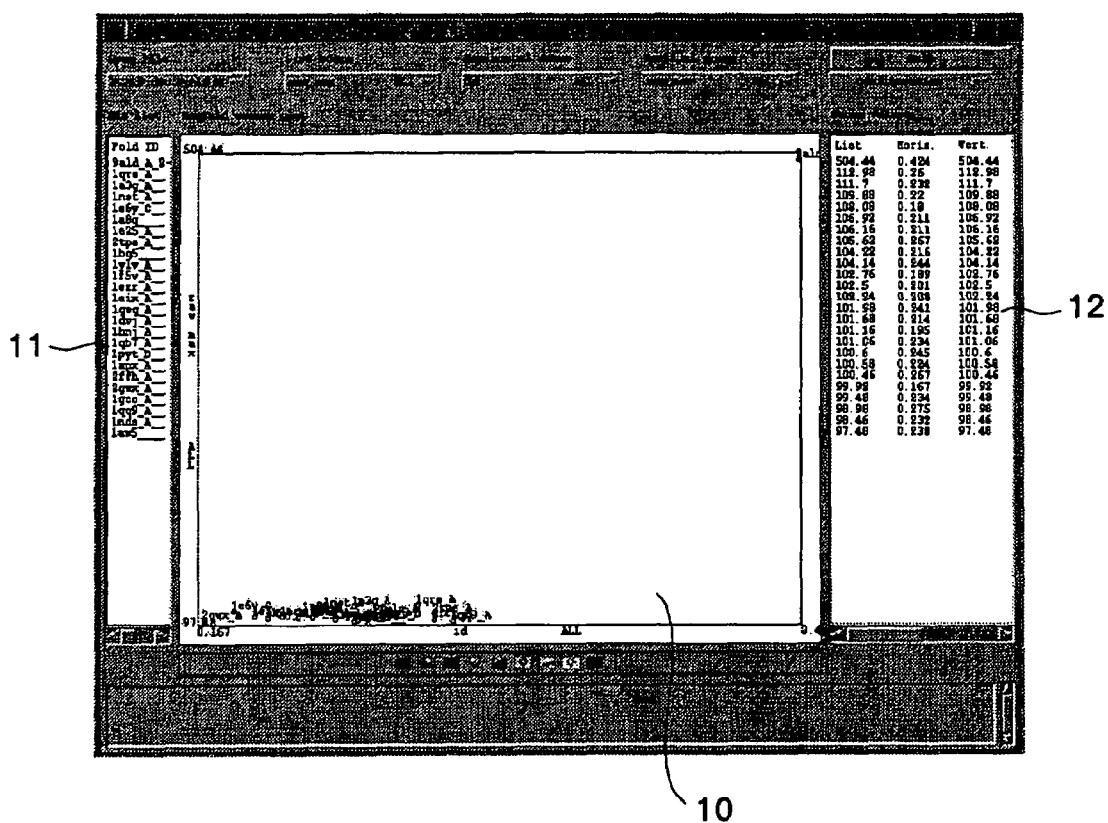
Figure 13:
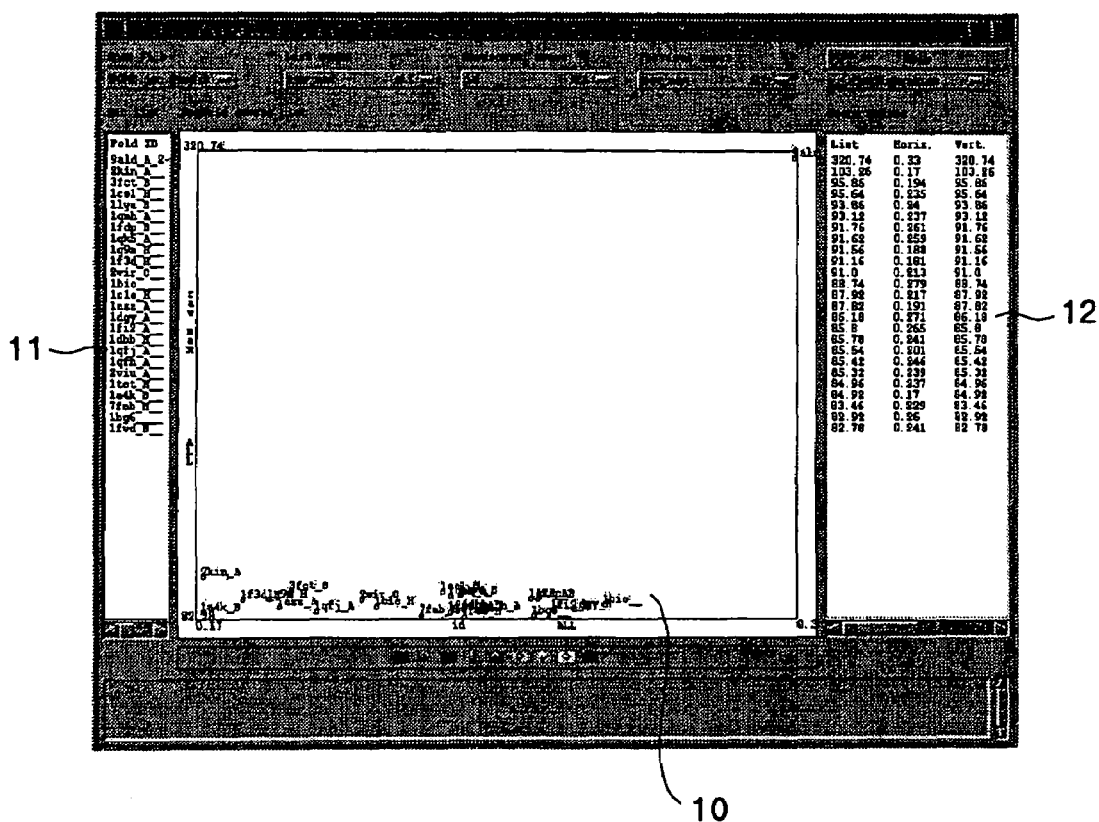
Figure 14:
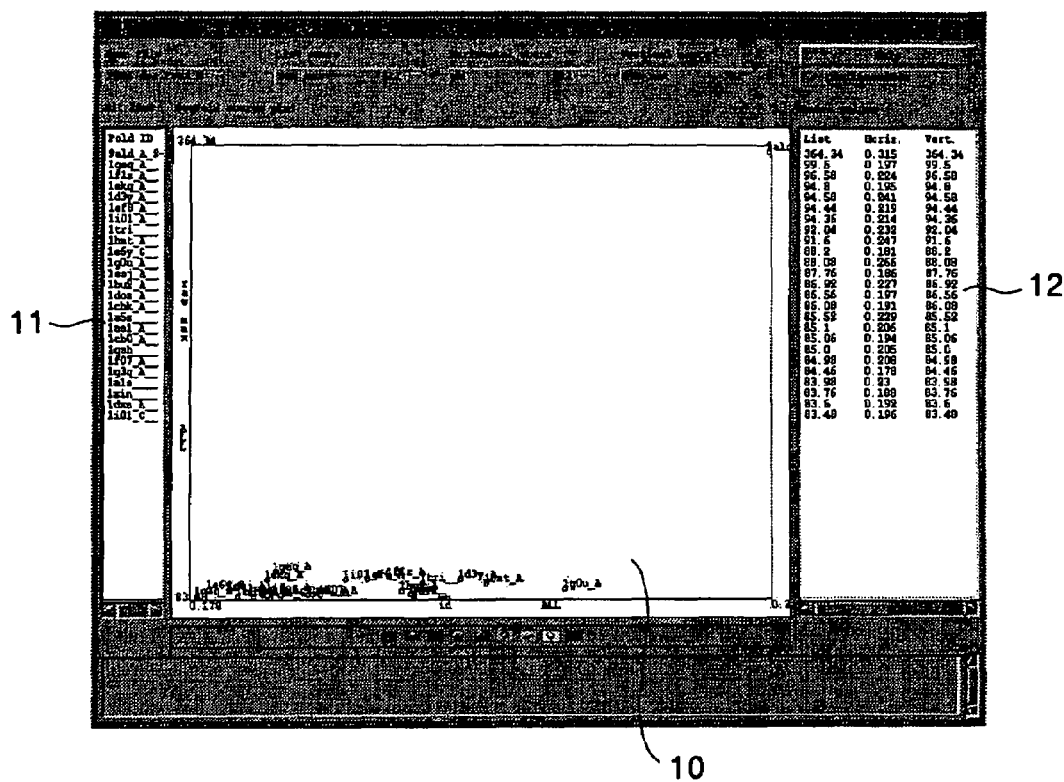

(ii) A case of determining the amino acid sequence of a variant aldolase from other aldolases than PtALD Hereinafter, a method for amino acid variation in the same manner as in PTALD will be explained on other aldolases than PtALD referring to FIG. 8, based on information of the PtALD structure obtained by X-ray crystallography. As for other aldolases, it is preferred to use a protein of which the amino acid sequence is known and the aldolase activity has been confirmed. In particular, it is preferred to use a protein of which the aldolase activity has been confirmed to catalyze at least one of the aldol condensation of indole-3-pyruvic acid with pyruvic acid to yield IHOG and the aldol condensation of phenylpyruvic acid with pyruvic acid to yield PHOG.

First, the three-dimensional structure of the other aldolase is compared to that of PtALD to find similarity to that of PtALD (Step S1).

In this connection, whether the other aldolase and PtALD have the similar three-dimensional structure or not may preferably be determined by the Threading method. In the Threading method, a certain amino acid is estimated and deduced which type of three-dimensional structure is applicable in the similarity to the known structure in a database (Science, 253, 164-170 (1991)). Specifically, the amino acid sequence of the other aldolase is superimposed on the three-dimensional structure of PtALD described in a Database to calculate the objective function quantifying the compatibility of both aldolases concerning easiness of forming a secondary structure, and the results are compared for evaluation. As the three-dimensional structural data for PtALD used by Threading method, those described in FIG. 9-1 to FIG. 9-26 can be used.

The Threading method can be performed according to a program such as INSIGHT II, LIBRA, etc. INSIGHT II is commercially available from Accelrys Co., USA. In order to perform the Threading method, a SeqFold module contained in the program is utilized. LIBRA may be used through an internet.

As a standard for judging whether a certain protein has similarity to the three-dimensional structure of PtALD, for example, in a case of using INSIGHT II-SeqFold, it is preferred to use SeqFold Total Score (bits) calculated by summing up all of the estimation functions by the Threading method. By calculating SeqFold Total Score (bits), it is possible to determine whether the three-dimensional structure of a protein totally resembles in that of PtALD. When the Threading method is carried out using a program SeqFold, a variety of estimation values such as SeqFold(LIB) P-Value, SeqFold(LEN) P-Value, SeqFold(LOW) P-Value, SeqFold (High) P-Value, SeqFold Total Score (raw), SeqFold Alignment Score (raw), etc., are calculated; SeqFold Total Score (bits) is a total estimation value calculated by summing up all of these estimation values. Thus, the higher SeqFold Total Score (bits) indicates higher similarity of the three-dimensional structure between two compared proteins. For example, when INSIGHT II is used in the Threading method, the threshold for determining that a protein has a three-dimensional structure similar to that of PtALD is considered to be approximately 100 as a proper SeqFold Total Score (bits). That is, if the SeqFold Total Score (bits) is 100 or more, the three-dimensional structure of the other aldolase could be determined to have similarity to that of PtALD. More preferred threshold is 105 or more, more preferably 120 or more, and particularly 150 or more to the SeqFold Total Score value.

In addition, it is preferred that PtALD and the other aldolase have much higher similarity to each other at the substrate-binding site. Thus, when the three-dimensional structure of the other aldolase has been determined, the similarity of the three-dimensional structure of a protein at the substrate-binding site may be determined in view of the general similarity of the three-dimensional structure of the protein using SeqFold Total Score (bits).

High similarity between PtALD and the other aldolase at the substrate-binding site may be determined if the deviation of the backbone Cα atom position in the 15 amino acid residues constituting the substrate-binding site is less than a predetermined threshold as a root mean square error when the three-dimensional structure of the other aldolase is superimposed on that of PtALD. As the threshold of determining the high similarity at the substrate-binding site, it is reasonable that the deviation of the backbone Cα atom position is approximately 4 angstrom as a root mean square error. That is, when the deviation of the backbone Cα atom position is 4 angstrom or less, it may be determined that PtALD and the other aldolase have higher similarity at the substrate-binding site. Specifically, the three-dimensional structure of the other aldolase is superimposed on that of PtALD. Then, it is judged whether the deviation of the backbone Cα atom position is less than the predetermined threshold between the 15 amino acid residues (Arg 37, Asn 67, Tyr 71, Gly 97, Glu 98, Leu 99, Ile 100, Arg 119, Asp 120, Pro 139, Lys 141, His 189, His 192, Glu 193, and Trp 209) constituting the substrate-binding site of PtALD and the corresponding 15 amino acid residues of the other aldolase, when both three-dimensional structures are superimposed to each other. Thus, when SeqFold Total Score (bits) is over the predetermined threshold or when the deviation of the backbone Cα atom position in the 15 amino acid residues constituting the substrate-binding site is lower than the predetermined threshold, the other aldolase may be judged to be a protein having the three-dimensional structure similar to PtALD.

When the other aldolase is judged to have the three-dimensional structure similar to PtALD (Step S2 Yes), the amino acid residues corresponding to Arg 37 and Leu 99 of PtALD are identified in the amino acid sequence of the other aldolase (Step S3). The amino acid residues corresponding to Arg 37 and Leu 99 of PTALD may be identified by conducting alignment of PtALD and other aldolase based on the tertiary structure by the Threading method.

Subsequently, the amino acid sequence of a variant aldolase is determined by substituting at least one of the amino acid residue corresponding to Arg 37 of PTALD and the residue corresponding to Leu 99 of PtALD in the above-mentioned protein (Step S4). The substitution of an amino acid residue as mentioned herein may be achieved with the same amino acid residues as those used in PtALD.

For example, in order to obtain the amino acid sequence of a variant aldolase having selectivity for a 4R-isomer, in the amino acid sequence of the other aldolase in which a high score is given relative to the similarity to PtALD, the amino acid residue corresponding to Arg 37 of PtALD may preferably be replaced with another amino acid residue such as tyrosine residue, tryptophan residue, histidine residue, phenylalanine residue, and proline residue. In addition, in the amino acid sequence of the other aldolase in which a high score is given relative to the similarity to PtALD, the amino acid residue corresponding to Leu 99 of PtALD may preferably be replaced with another amino acid residue such as aspartic acid residue, glutamic acid residue, lysine residue, tryptophan residue and glycine residue. The above-mentioned substitution may be made on both the amino acid residue corresponding to Arg 37 of PtALD and the amino acid residue corresponding to Leu 99 of PtALD.

The present inventors have applied the Threading method using INSIGHT II to three species of aldolases derived from *Pseudomonas coronafaciens*, *Arthrobacter keyseri*, and *Pseudomonas ochraceae* and found that these aldolases have a three-dimensional structure similar to that of PtALD (Example 13).

The SeqFold Total Score (bits) between the amino acid sequences of the aldolase derived from *Pseudomonas coronafaciens* (PcALD) and of PtALD is 165.94.

The amino acid sequence of PcALD is shown in SEQ ID NO: 23 of Sequence Listing, and the result of alignment of PcALD and PtALD is shown in FIG. 15. In FIG. 15, the upper line indicates the amino acid sequence of PcALD and the lower line is that of PTALD; the asterisk (*) indicates the portion at which both amino acid residues are identical. Further, in FIG. 15, the double-hatched portion indicates the active site of PtALD comprised of 15 amino acid residues (Arg 37, Asn 67, Tyr 71, Gly 97, Glu 98, Leu 99, Ile 100, Arg 119, Asp 120, Pro 139, Lys 141, His 189, His 192, Glu 193, and Trp 209). As for Asp 120 at which the modification is likely to disturb the aldolase activity, it is found that the same amino acid residue in PcALD as that of PtALD participates therein.

In PcALD, the amino acid residue corresponding to Arg 37 of PtALD is Arg, and the amino acid residue corresoponding to Leu 99 is Met. Therefore, at least one of these two amino acid residues may be introduced thereinto. Though Met corresponding to Leu 99 in PtALD is different from that of PtALD in species, in this case, it may be substituted by an amino acid residue other than Met and Leu to modify the optical selectivity of a wild-type PcALD.

The SeqFold Total Score (bits) between the amino acid sequences of the aldolase derived from *Arthrobacter keyseri* (PcmE) and of PtALD is 105.51.

The amino acid sequence of PcmE is shown in SEQ ID NO: 24 of Sequence Listing, and the result of alignment of PcmE and PtALD is shown in FIG. 16. In FIG. 16, the upper line indicates the amino acid sequence of PcmE and the lower line is that of PtALD; the asterisk (*) indicates the portion at which both amino acid residues are identical. Further, in FIG. 16, the double-hatched portion also indicates the active site of PtALD comprised of 15 amino acid residues. As for Asp 120 at which the modification is likely to disturb the aldolase activity, it is found that the same amino acid residue in PcmE as that of PTALD participates therein.

In PcmE, the amino acid residue corresponding to Arg 37 of PtALD is Arg, and the amino acid residue corresponding to Leu 99 of PtALD is Leu. Therefore, in the amino acid sequence of PcmE, when a substitution is made on at least one of these two amino acid residues, optical selectivity may be given.

The SeqFold Total Score (bits) between the amino acid sequences of the aldolase derived from *Pseudomonas ochraceae* (ProA) and of PtALD is 119.85.

The amino acid sequence of ProA is shown in SEQ ID NO: 25 of Sequence Listing, and the result of alignment of ProA and PtALD is shown in FIG. 17. In FIG. 17, the upper line indicates the amino acid sequence of ProA and the lower line is that of PtALD; the asterisk (*) indicates the portion at which both amino acid residues are identical. Further, in FIG. 17, the double-hatched portion also indicates the active site of PtALD comprised of 15 amino acid residues. As for Asp 120 of PtALD at which the modification is likely to disturb the aldolase activity, it is found that the same amino acid residue in ProA as that of PtALD participates therein.

In ProA, the amino acid residue corresponding to Arg 37 of PtALD is Arg, and the amino acid residue corresponding to Leu 99 of PtALD is Leu. Therefore, in the amino acid sequence of ProA, when a substitution is made on at least one of these two amino acid residues, optical selectivity may be given.

Aldolases of which the three-dimensional structure is similar to PtALD, however, are not limited to PcALD, PcmE, and ProA, and thus, it need scarcely be said that aldolases derived from other strains may be modified by substitution with the same amino acid residues as far as the three-dimensional structure of them is similar to that of PtALD.

With respect to aldolases similar to PTALD in the three-dimensional structure, in combination of the above-mentioned variant introduction into the amino acid residues corresponding to Arg 37 and Leu 99, the remaining amino acid residues constituting the substrate-binding site of PtALD except Asp 120, that is, at least one of the amino acid residues corresponding to Asn 67, Tyr 71, Gly 97, Glu 98, Ile 100, Arg 119, Pro 139, Lys 141, His 189, His 192, Glu 193, and Trp 209 may be modified by substitution, deletion, insertion, addition and/or inversion. Since the amino acid residues corresponding to these 12 amino acid residues constitute a substrate-binding site, it may be expected that productivity or substrate specificity of PHOG or IHOG may be modified by substitution with the amino acid residues different from those of PtALD. When the amino acid residues corresponding to these 12 amino acid residues are originally different from those of PtALD, they may be substituted by the same amino acid residues as those of PtALD. In the amino acid residues constituting the substrate-binding site of PtALD, the amino acid residues different from those of PtALD may be substituted by the same amino acid residues as those of PtALD, sometimes resulting in improvement of the productivity of PHOG or IHOG. When a variation is introduced into the amino acid residues corresponding to the above-mentioned 12 amino acid residues, however, it may be conducted within the range that the aldolase activity and optical selectivity obtained by the substitution of Arg 37 or Leu 99 by another amino acid residue will not be disturbed considerably.

As for the amino acid sequence of aldolases similar to PtALD in the three-dimensional structure, the aldolases in which one or several of the other amino acid residues not corresponding to those constituting the substrate-binding site of PtALD are modified by substitution, deletion, insertion, addition and/or inversion are included in the variant aldolases of the invention as far as the aldolase activity and optical selectivity obtained by the substitution of Arg 37 or Leu 99 by another amino acid residue is not disturbed considerably.

The term "one or several" as mentioned herein means the number within which range the three-dimensional whole structure of protein, the aldolase activity, and the optical selectivity obtained by the substitution of Arg 37 or Leu 99 by another amino acid residue is not disturbed considerably, and specifically includes 1 to 50, preferably 1 to 30, and more preferably 1 to 10 amino acids. In such a case, the aldolase activity in the protein having the amino acid sequence as described in SEQ ID NO: 2 of Sequence Listing, and variants thereof, is maintained in a condition of 33° C. and pH 9 by 1% or more, preferably 5% or more, more preferably 20% or more, even more preferably 50% or more, particularly preferably 70% or more, and especially preferably 100% or more.

(B) Process for Production of a Variant Aldolase

A variant of aldolase of the invention may be produced by introducing a variation into a gene coding for an amino acid sequence of the wild-type of aldolase to yield a gene coding for a variant of aldolase and then expressing the variant gene in a suitable host.

A variant aldolase may also be produced by expressing in a suitable host a variant aldolase gene isolated from a variant strain which produces a variant of aldolase.

(i) Acquisition of a Wild-Type Aldolase Gene

When a variant aldolase is prepared using PtALD, a wild-type aldolase gene may be cloned from *Pseudomonas taetrolens* ATCC4683 cells.

When a variant aldolase is prepared from another aldolase of which the three-dimensional structure is similar to that of PtALD, a wild-type aldolase gene may be cloned from the cells of microorganisms that produce the objective enzyme. Examples of bacteria producing the other aldolase of which the three-dimensional structure is similar to that of PtALD include but are not limited to *Pseudomonas coronafaciens*, *Arthrobacter keyseri*, and *Pseudomonas ochraceae*. Among them, *Pseudomonas coronafaciens* is more preferred. This strain has been deposited as follows.

*Pseudomonas coronafaciens* AJ2791 strain
(a) Accession Number. FERM BP-8246 (moved to an international deposit on Nov. 22, 2002 from FERM P-18881 deposited on Jun. 10, 2002)
(b) Date of Acceptance: Jun. 10, 2002
(c) Depository Institution:
International Patent Organism Depository,
National Institute of Advanced Industrial Science and Technology (Tsukuba Central 6, 1-1, Higashi 1-chome, Tsukuba-shi, Ibaraki-ken, Japan)

*Arthrobacter keyseri* and *Pseudomonas ochraceae* are described in the following documents and known to be aldolase active bacteria.

*Arthrobacter keyseri* 12B strain
(a) Document: Eaton, R. W., Plasmid-encoded phthalate catabolic pathway in *Arthrobacter keyseri* 12B, J. Bacteriol. 183(12), 3689-3703 (2001)
(b) Genebank Accession Number: AF331043

*Pseudomonas ochraceae* NGJ 1 strain
(a) Document: Maruyama, K., Miwa, M., Tsujii, N., Nagai, T., Tomita, N., Harada, T., Sobajima, H. and Sugisaki, H., Cloning, sequencing, and expression of the gene encoding 4-hydroxy-4-methyl-2-oxoglutarate aldolase from *Pseudomonas ochraceae* NGJ1, Biosci. Biotechnol. Biochem. 65(12), 2791-2709 (2001)
(b) Genebank Accession Number: AB050935

The followings will explain a method for preparing a DNA coding for a wild-type of aldolase from an aldolase-producing bacterium.

Based on the base sequence of a wild-type aldolase gene, a DNA molecule of about 30 base pairs is synthesized. A process for synthesizing the DNA molecule is disclosed in Tetrahedron Letters, 22, 1859 (1981). Alternatively, the DNA molecule may be synthesized by means of a synthesizer (Applied Biosystems).

The DNA molecule of about 30 base pairs can be utilized as a probe for isolating the whole length of DNA coding for an aldolase from a chromosomal gene library of aldolase-producing bacteria. Alternatively, it may be utilized as a primer in amplification of an aldolase-encoding DNA by PCR. The DNA amplified by PCR, however, contains no whole length of DNA coding for an aldolase, and accordingly it may be used as a probe in isolation of the whole length of DNA coding for an aldolase from a chromosomal gene library of aldolase-producing bacteria.

The procedure for PCR is described in White, T. J. et al., Trends Genet. 5, p. 185, etc. (1989). A method of preparing a chromosomal DNA, as well as a method for isolating an objective DNA molecule from a gene library using a DNA molecule as a probe are described in, for example, Molecular Cloning, 2nd edition, Cold Spring Harbor press (1989).

(ii) Preparation of a Variant Aldolase Gene

A variant aldolase gene may be prepared by artificially varying a wild-type aldolase gene isolated from the above-mentioned aldolase-producing bacterium at a predetermined portion. When a variant aldolase gene having optical selectivity is prepared with a wild-type PtALD gene, the wildetype PtALD gene is artificially varied so that a protein in which at least one of the amino acid residues, Arg 37 and Leu 99, is modified by substitution is produced. When a variant aldolase gene having optical selectivity is prepared with a wild-type aldolase gene other than PTALD gene, the gene is artificially mutated so that a protein in which at least one of the amino acid residues corresponding to Arg 37 of PtALD and corresponding to Leu 99 of PtALD is modified by substitution is produced.

As a method for site-specific variation causing an objective variation in DNA at the objective site, there is a method by PCR (Higuchi, R., in PCR technology, 61, Erlich, H. A. Eds., Stockton press, 1989; Carter, P., Meth. in Enzymol., 154, 382 (1987)); and a method using a phage (Kramer, W. and Frits, H. J., Method in Enzymol., 154, 350 (1987); Kunkel, T. A. et al., Meth. in Enzymol., 154, 367 (1987)).

Specific examples of variant aldolase DNAs that are modified so as to selectively generate the 4R-isomer of IHOG include those coding for proteins with the following amino acid sequences.

(1) In the amino acid sequence of SEQ ID NO: 2, the amino acid sequence in which the 37th arginine residue is replaced with a tyrosine residue.

(2) In the amino acid sequence of SEQ ID NO: 2, the amino acid sequence in which the 37th arginine residue is replaced with a tryptophan residue.

(3) In the amino acid sequence of SEQ ID NO: 2, the amino acid sequence in which the 37th arginine residue is replaced with a histidine residue.

(4) In the amino acid sequence of SEQ ID NO: 2, the amino acid sequence in which the 37th arginine residue is replaced with a phenylalanine residue.

(5) In the amino acid sequence of SEQ ID NO: 2, the amino acid sequence in which the 37th arginine residue is replaced with a proline residue.

(6) In the amino acid sequence of SEQ ID NO: 2, the amino acid sequence in which the 99th leucine residue is replaced with an aspartic acid residue.

(7) In the amino acid sequence of SEQ ID NO: 2, the amino acid sequence in which the 99th leucine residue is replaced with a glutamic acid residue.

(8) In the amino acid sequence of SEQ ID NO: 2, the amino acid sequence in which the 99th leucine residue is replaced with a lysine residue.

(9) In the amino acid sequence of SEQ ID NO: 2, the amino acid sequence in which the 99th leucine residue is replaced with a tryptophan residue.

(10) In the amino acid sequence of SEQ ID NO: 2, the amino acid sequence in which the 99th leucine residue is replaced with a tyrosine residue.

(11) In the amino acid sequence of SEQ ID NO: 2, the amino acid sequence in which the 99th leucine residue is replaced with a glycine residue.

(12) In the amino acid sequence of SEQ ID NO: 2, the amino acid sequence in which the 37th arginine residue is replaced with a phenylalanine residue and the 99th leucine residue is replaced with a lysine residue.

(13) In the amino acid sequence of SEQ ID NO: 2, the amino acid sequence in which the 37th arginine residue is replaced with a tyrosine residue and the 99th leucine residue is replaced with a lysine residue.

(14) In the amino acid sequence of SEQ ID NO: 2, the amino acid sequence in which the 37th arginine residue is replaced with a tryptophan residue and the 99th leucine residue is replaced with a lysine residue.

In order to deduce a coding DNA based on the above items (1) to (14), the universal codons of DNA base sequences may be employed.

In addition, the DNA coding for an aldolase which has the amino acid sequence substituted at the site other than the substrate-binding site of these variant aldolases, that is, the amino acid sequence as mentioned in the items (1) to (14), as well as the DNA coding for an aldolase having the amino acid sequence in which one or several of the amino acid residues are modified by substitution, deletion, insertion, addition and/or inversion at the position other than the positions 37, 67, 71, 97, 98, 99, 100, 119, 120, 139, 141, 189, 192, 193 and 209, and having selectivity for the 4R-isomer, are also included. The definition "one or several" as described herein has the same significances as mentioned in Section of (A) the design of a variant of aldolase.

Naturally, the DNAs which code for proteins having the amino acid sequences of the items (1) to (14) and can hybridize in a stringent condition with DNAs having complementary base sequences and coding for variant aldolases having selectivity for the 4R-isomers are also exemplified. The term "stringent condition" as used herein means a condition in which only a specific hybrid is formed but not a non-specific hybrid. Though it is difficult to clearly represent numerically this condition, an example includes a condition wherein DNAs mutually have high homology, for example, 80% or more, preferably 85% or more, more preferably 90% or more, particularly 95% or more, hybridize to each other, but DNAs do not hybridize with those having lower homology (herein, it is desirous to calculate the homology when the two sequences are aligned so that the number of the identical bases is maximum), or a condition in which they hybridize in a washing condition of the Southern hybridization, i.e., at 37° C. in a salt concentration of 0.1×SSC/0.1% SDS, preferably at 60° C. in 0.1×SSC/0.1% SDS, and more preferably at 65° C. in 0.1×SSC/0.1% SDS. However, in a case of the DNAs which code for proteins having the amino acid sequences of the items (1) to (14) and can hybridize in a stringent condition with DNAs having complementary base sequences and coding for variant aldolases having selectivity for the 4R-isomers, it is desirous that the corresponding protein maintains in a condition at 33° C. and pH 9 an aldolase activity of 1% or more, preferably 5% or more, more preferably 20% or more, even more preferably 50% or more, and particularly 100% or more of a protein having the amino acid sequence as described in SEQ ID NO: 2 of Sequence Listing.

Therefore, the substitution of a base in the particular site of a wild-type aldolase gene may be conducted by the above-mentioned specific variation so that it codes for a variant aldolase.

(iii) Preparation of a Variant Aldolase-Producing Bacterium and Culture Thereof

The DNA fragment containing a gene coding for a variant aldolase obtained as mentioned above is again integrated into a suitable vector and introduced into a host cell to yield a transformant expressing a variant aldolase.

A number of processes for producing useful proteins such as enzymes and physiologically active substances utilizing a recombinant DNA technique have been known, and thus, a variety of naturally occurring trace proteins can be produced utilizing a recombinant DNA technique on a large scale. The integrated genes include those as mentioned in the section of (ii) Preparation of a variant aldolase gene.

As a transformant host cell, bacterial cell, actinomycetes cell, yeast cell, fungal cell, plant cell, or animal cell can be used. As for the bacterial cells for which a host-vector system has been developed, bacteria of *Escherichia, Pseudomonas, Corynebacterium, Bacillus*, and the like are exemplified, and *Escherichia coli* is preferably used because there are a large number of findings on the techniques for mass production of proteins using it. The followings will explain a process for producing aldolase with a transformant *Escherichia coli*.

As a promoter for expressing a DNA coding for a variant aldolase, a promoter which has usually been used in production of heterologous proteins in *Escherichia coli* may be used, for example, powerful promoters such as T7 promoter, trp promoter, lac promoter, tac promoter, PL promoter, can be included.

In order to produce a variant aldolase as an inclusion body of fused protein, a gene coding for another protein, preferably a hydrophilic peptide, is linked to the upstream or downstream of an aldolase gene to yield a fused protein gene. As for a gene coding for the other protein, those which promote accumulation of the fused proteins and increase the solubility of them after the steps of variation and regeneration may be used, and, for example, T7 gene 10, β-galactosidase gene, dehydro-folic acid reductase, interferon γ gene, interleukin 2 gene, prochymosin gene, and the like are exemplified as candidates.

In linking these genes with a gene coding for a variant aldolase, they are arranged so that their reading frame coincides with each other. For that purpose, they may be linked at suitable restriction enzyme sites or a synthetic DNA with a suitable sequence may be utilized.

In order to increase the yield, it is preferred to link a terminator, transcription-terminating sequence, to the downstream of a fused protein gene. Such a terminator includes T7 terminator, fd phage terminator, T4 terminator, tetracyclin resistant gene terminator, *Escherichia coli* trpA gene terminator, and the like.

As a vector for introducing a gene coding for a variant of aldolase or a fused protein comprised of a variant aldolase and another protein, a so-called multicopy-type vector is preferred, including a plasmid having an initiation point of replication derived from Col E1, for example, pUC-series or pBR322-series plasmid, or their derivatives. The term "derivative" as described herein means a plasmid modified by substitution, deletion, insertion, addition or inversion of the base. The term modification also includes those by variation with a mutagen or UV irradiation or by natural variation.

In order to select transformants, it is preferred that the vector contains a marker such as ampicillin resistant gene. Such plasmids are commercially available as expression vectors having powerful promoters (pUC series (Takara Shuzo), pPROK series (Clontech), pKK233-2 (Clontech), etc.).

A DNA fragment in which a promoter, a gene coding for a variant of aldolase or a fused protein comprised of a variant aldolase and another protein, and a terminator are linked together in this order, is linked to a vector DNA to yield a recombinant DNA.

This recombinant DNA is transformed into *Escherichia coli*, which is cultured to yield a variant of aldolase or a fused protein comprised of a variant aldolase and another protein as an expression product. The transformed host is used as a strain which is usually used in expression of a heterologous gene; preferred strains are *Escherichia coli* JM109(DE3) and JM109. Method for transformation and a method for selection of transformants are described in Molecular Cloning, 2nd edition, Cold Spring Harbor press (1989), etc.

Though a variant aldolase of the invention can be produced by expressing a variant gene which is obtained by direct variation of a gene coding for a wild-type aldolase as mentioned above, it may also be produced by culturing a variant strain prepared from an aldolase-producing microorganism (e.g., *Pseudomonas*) by UV irradiation or by treatment with a mutagen usually used in artificial variation such as N-methyl-N'-nitro-N-nitrosoguanidine (NTG) and capable of generating IHOG and PHOG in an optically selective way.

The followings will explain a method for culturing a microorganism in the invention. The term "microorganism" as mentioned herein means both a genetic recombination cell which expressed a variant aldolase of the invention and a variant strain which became to produce a variant aldolase. The culture condition described herein can be applied to both a culture for making a microorganism produce a variant aldolase and recovering it, and a culture of a microorganism for producing a variant aldolase and simultaneously allowing the reaction producing IHOG.

The culture of a microorganism in the invention may be conducted in a culture medium usually used in this field, i.e., a medium containing a carbon source, nitrogen source, inorganic salts, trace metal salts, vitamins, etc.

In carrying out the culture of a genetic recombination cell, a drug such as ampicillin, kanamycin, neomycin, chloramphenicol, and the like may be added properly corresponding to a selective marker of vector. It is also possible to increase an amount of expression of the recombinant gene by adding a proper amount of an inducer responding to a promoter integrated in a vector. For example, when a vector is constructed with a lac promoter to which an objective gene is linked at the downstream, it is possible to add properly isopropyl 1-thio-β-D-galactopyranoside (IPTG) at a final concentration of 0.1 mM to 5 mM, or alternatively it is also possible to add properly galactose at a final concentration of 0.1-5 g/dl, desirably 0.5 g/dl-2 g/dl.

The culture may be carried out usually at a temperature at which a microorganism to be utilized can be grown, i.e., 10-45° C., preferably 20° C.-40° C., more preferably 25-37° C. The pH range is adjusted preferably within the range of 2-12, more preferably 3-10, and even more preferably 4-8. Aeration may be set in accordance with a growing condition for a microorganism to be utilized, preferably in an aerobic condition. The culture may be continued usually for a period of 12-120 hours, preferably 24-96 hours.

By culturing a genetically recombinant cell expressing a variant aldolase or a variant stran producing a variant aldolase, a variant aldolase of the invention can be accumulated in the cells or a culture broth.

[III] Process for Production of an Optically Active IHOG

In a process for producing an optically active IHOG of the invention, IHOG is produced by aldol condensation of indolepyruvic acid and pyruvic acid (or oxalacetic acid) using a variant aldolase of the invention of which the optical selectivity is modified. Using a variant of aldolase of the invention, an optically active IHOG can be produced; the resulting optically active IHOG may be aminated to yield an optically active monatin.

The variant aldolase of the invention allows efficient asymmetric induction at the step of aldol condensation reaction. In the prior art process, the resulting IHOG was a mixture of 4R-isomer and 4S-isomer (racemate), but the use of an aldolase of the invention allows the predominant production of either 4R-isomer or 4S-isomer according to the purpose; thus, 4R-rich or 4S-rich IHOG can be produced.

In order to produce (2R,4R)-monatin efficiently, it is preferred to use a variant aldolase producing 4R-IHOG predominantly to yield a 4R-rich IHOG. Examples of such variant aldolases include those having the amino acid sequences as described in the above items (1) to (14).

The variant of aldolase of the invention may be added to the reaction medium directly or as a microorganism containing it, as far as it catalyzes the aldol condensation reaction to yield IHOG from indolepyruvic acid and pyruvic acid (or oxalacetic acid).

The additive containing a variant aldolase specifically includes a cultured product, culture medium (the culture product from which the cells have been removed), cells (including both of cultured cells and washed cells), cells processed by crushing or lysis, an aldolase active composition derived by purification from the above-mentioned culture medium and/or cells (crude enzyme solution, purified enzyme), and the like. For example, when IHOG is produced with a bacterium producing a variant aldolase, the substrates may be added directly to the culture broth during incubation of the bacterium. The cells separated from the culture broth, the washed cells, or the cells processed by crushing or lysis may be added to the reaction mixture, or alternatively an aldolase is recovered from the processed cells and may be added as a crude enzyme solution or purified enzyme to the reaction mixture. That is, any form of fraction containing a variant aldolase may be used in production of IHOG in the invention.

In order to carry out the aldol condensation reaction using a variant aldolase of the invention, a reaction mixture containing indolepyruvic acid, pyruvic acid (or oxalacetic acid), and a variant aldolase of the invention may be adjusted at a temperature of 20-50° C. and allowed to stand, shaken or stirred while keeping at pH 6-12 for a period of 30 minutes to 5 days.

Though the substrate concentration may be increased in the reaction mixture to increase the amount of the product IHOG, the optical purity of the product IHOG might be varied depending on the reaction condition such as substrate concentration. Therefore, if the optical purity of the product IHOG is considered more important than the yield of IHOG, the substrate concentration might be controlled as the occasion demands.

Addition of a divalent cation such as $Mg^{2+}$, $Mn^{2+}$, or $Co^{2+}$ to the reaction mixture may be effective in increase of the reaction rate. In view of the cost, sometimes $Mg^{2+}$ may preferably be used.

When a divalent cation is added to the reaction mixture, any salt may be used as far as the reaction is not disturbed, and sometimes $MgCl_2$, $MgSO_4$, $MnSO_4$, etc. may preferably be used. The amount of the divalent cation to be added may readily be determined by a person skilled in the art based on a simple preliminary test, and it may be added in the range of 0.0 mM to 10 mM, preferably 0.1 mM to 5 mM, and more preferably 0.1 mM to 1 mM.

[IV] Process for Production of an Optically Active Monatin

In a process for producing an optically active monatin in the invention, an optically active IHOG produced with a variant aldolase of the invention is converted into an optically active monatin. 4R-IHOG yields (2R,4R)-monatin and (2S, 4R)-monatin; and 4S-IHOG yields (2R,4S)-monatin and (2S, 4S)-monatin.

Of these 4 isomers of monatin, the sweetest one is (2R,4R)-monatin, which may preferably be produced efficiently from the 4R-rich IHOG. In such a case, it is preferred that the content of 4R-IHOG in the total amount of IHOG is more than 55%, more preferably more than 60%, even more preferably more than 70%, and particularly preferably more than 80%.

The conversion of IHOG into monatin can be achieved in a conventional manner by means of a chemical reaction or by an enzymatic means.

(i) Process by Chemical Reaction

In producing monatin from IHOG by chemical reaction, IHOG is converted into an oxime, and the latter IHOG-oxime or a salt thereof is reduced to yield monatin.

Preferably, a 4R-rich IHOG is converted into an oxime, and the 4R-IHOG-oxime or a salt thereof is isolated from a solution containing the 4R-rich IHOG-oxime by crystallization and chemically reduced to yield 4R-monatin.

Formation of the IHOG oxime is achieved by reacting IHOG with an amine compound of the general formula (1):

$$H_2N-OR \tag{1}$$

wherein R is a hydrogen atom, alkyl group, aryl group or aralkyl group, or a salt thereof in a neutral or alkaline condition.

In this situation, when R is an alkyl group, aryl group or aralkyl group, R is preferably an alkyl group of 1-3 carbon atoms or an aryl or aralkyl group which may have a substituent on the side chain; in view of crystallization, R is preferably selected from methyl group, ethyl group and benzyl group.

The reaction for the oxime formation may be conducted by adding an amine of the general formula (1) directly to the aldolase reaction mixture containing IHOG. From this solution containing 4R-rich IHOG-oxime, 4R-IHOG-oxime or a salt thereof can be crystallized out as a single product. The solvent preferably used in crystallization includes water, an alcohol solvent, or an aqueous alcohol solvent.

4R-IHOG-oxime or a salt thereof obtained by crystallization is reduced to yield 4R-monatin. The reduction of 4R-IHOG-oxime or a salt thereof is carried out in the presence of hydrogen and a hydrogenation catalyst. The catalyst for hydrogenation is exemplified by a metal-carrier catalyst in which a metal such as platinum, rhodium, palladium, nickel or cobalt is kept on a carrier such as silica, alumina, titania, magnesia, zirconia or active carbon.

In the prior art, since an optically active IHOG could not be produced efficiently, in order to isolate 4R-IHOG from IHOG (4R,4S-IHOG), it was necessary to convert 4R,4S-IHOG into an oxime, and then reacting the latter with a chiral amine to crystallize 4R-IHOG-oxime. According to the invention, however, a 4R-rich IHOG can be produced in the stage of the aldol condensation reaction, and optical resolution with a chiral amine is not necessary in crystallization, accordingly; the 4R-rich IHOG is converted into an oxime, from which 4R-IHOG-oxime can be crystallized directly. Therefore, the cost needed for purification of 4R-IHOG can be reduced.

4R-Monatin obtained by the chemical reduction is a racemic mixture of (2R,4R)-monatin and (2S,4R)-monatin. In a case of isolating (2R,4R)-monatin, (2R,4R)-monatin can be precipitated by crystallization. Specifically, a method as described in International Patent Publication Pamphlet No.03/059865 may be utilized.

(ii) Enzymatic Method

When monatin is produced from IHOG by an enzymatic method, IHOG may be aminated with an enzyme capable of catalyzing amination of IHOG at the position 2. The enzyme catalyzing the amination reaction includes, for example, aminotransferase catalyzing the transfer of an amino group in IHOG, or dehydrogenase catalyzing the reductive amination reaction of IHOG; it is more preferable to use an aminotransferase.

When an aminotransferase is used, IHOG is allowed to react in the presence of an aminotransferase and an amino group-donor to yield monatin. Specifically, a method as described in International Patent Publication Pamphlet No.03/056026 may be utilized.

In this reaction, as an aminotransferase, any of L-aminotransferase and D-aminotransferase may be used. When L-aminotransferase is used, 2S-monatin is selectively produced by transferring the amino group of L-amino acid to the position 2 of IHOG. On the other hand, when D-aminotransferase is used, 2R-monatin is selectively produced by transferring the amino group of D-amino acid to the position 2 of IHOG. Therefore, in order to produce selectively the highly sweet (2R,4R)-monatin, it is appropriate to use D-aminotransferase in the reaction of 4R-rich IHOG.

According to the study by the present inventors, it is considered that when the amination is carried out by action of an enzyme such as aminotransferase, 4S-IHOG acts competitively as inhibitor against 4R-IHOG in the step of the amination of IHOH to monatin. When a variant aldolase of the invention is used in the aldol condensation reaction, by-producing 4S-IHOG can be reduced, whereby the inhibitory effect of 4S-IHOG can be inhibited, and the yield of the objective (2R,4R)-monatin is improved.

Summary of Sequences Appearing in Sequence Listing:

SEQ ID NO: 1: DNA of aldolase derived from *Pseudomonas taetrolens*

SEQ ID NO: 2: Aldolase derived from *Pseudomonas taetrolens*

SEQ ID NO: 3: Primer
SEQ ID NO: 4: Primer
SEQ ID NO: 5: Primer
SEQ ID NO: 6: Primer
SEQ ID NO: 7: Primer
SEQ ID NO: 8: Primer
SEQ ID NO: 9: Primer for preparation of R37Y
SEQ ID NO: 10: Primer for preparation of R37W
SEQ ID NO: 11: Primer for preparation of R37H
SEQ ID NO: 12: Primer for preparation of R37P
SEQ ID NO: 13: Primer for preparation of R37F
SEQ ID NO: 14: Primer for preparation of L99D
SEQ ID NO: 15: Primer for preparation of L99W
SEQ ID NO: 16: Primer for preparation of L99Y
SEQ ID NO: 17: Primer for preparation of L99G
SEQ ID NO: 18: Primer for preparation of L99K
SEQ ID NO: 19: Primer for preparation of D120A
SEQ ID NO: 20: Primer for preparation of L99E
SEQ ID NO: 21: Primer for preparation of L99H
SEQ ID NO: 22: Primer for preparation of L99V
SEQ ID NO: 23: Aldolase derived from *Pseudomonas coronafaciens*
SEQ ID NO: 24: Aldolase derived from *Arthrobacter keyseri*
SEQ ID NO: 25: Aldolase derived from *Pseudomonas ochraceae*

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

In the following examples, IHOG and PHOG were quantitatively analyzed by HPLC using Inertsil ODS-2 (5 µm, 4.6×250 mm) (GL Science). Analytical conditions were as follows.

Mobile phase: 40% (v/v) acetonitrile/5 mM tetrabutylammonium dihydrogen phosphate solution Flow rate: 1 ml/min Column temperature: 40° C.

Detection: UV210 nm

The analysis of asymmetry of the 4-position of the product IHOG or PHOG was performed by HPLC using an Inertsil ODS-3 (5 µm, 4.6×250 mm) (GL Science) and SUMICHIRAL OA-710 (5 µm, 4.6×250 mm) (Sumitomo Chemical Analytical Center) connecting in series. Analytical conditions were as follows.

Mobile phase A: 5% (v/v) acetonitrile 20 mM potassium phosphate buffer (pH 6.8)

Mobile phase B: 50% (v/v) acetonitrile 20 mM potassium phosphate buffer (pH 6.8)

Elution with Mobile phase A for 0-90 minutes, then with Mobile phase B for 90-120 minutes, then washing.

Flow rate: 0.4 ml/min

Column temperature: 17° C.

Detection: UV 210 nm

Example 1

Mass Expression of IHOG Aldolase (PtALD) in *E. coli*

(1) Construction of Plasmid pTrp4 in Which trp Promoter and rrnB Terminator are Integrated The promoter domain of trp operon on *E. coli* W3110 chromosomal DNA as the objective gene region was amplified by PCR using oligonucleotides shown in Table 2 (in combination of SEQ ID NOs: 3 and 4) as primers, and the resulting DNA fragment was ligated in pGEM-Teasy vector (Promega). *E. coli* JM109 was transformed with this ligation solution, and a strain containing the objective plasmid was selected from the ampicillin resistant strains, wherein in the objective plasmid the trp promoter is inserted in the reverse direction of lac promoter. Then, this plasmid was treated with EcoO109i/EcoRI, and the resulting DNA fragment containing trp promoter was ligated with a EcoO109i/EcoRI-treated pUC19 (Takara). *E. coli* JM109 was transformed with this ligation solution, and a strain containing the objective plasmid was selected from the ampicillin resistant strains; and this plasmid was designated as pTrp1.

Then, pKK223-3 (Amersham Pharmacia) was treated with HindIII/HincII, and the resulting DNA fragment containing rrnB terminator was ligated with a HindIII/PvuII-treated pTrp1. *E. coli* JM109 was transformed with this ligation solution, and a strain containing the objective plasmid was selected from the ampicillin resistant strains; this plasmid was designated as pTrp2.

Using Trp2 as a template, the trp promoter domain was amplified by PCR using oligonucleotides as shown in Table 2 (in combination of SEQ ID NOs: 3 and 5) as primers. This DNA fragment was treated with Eco109i/NdeI, and ligated with an Eco109i/NdeI-treated pTrp2. *E. coli* JM109 was transformed with this ligation solution, and a strain containing the objective plasmid was selected from the ampicillin resistant strains; this plasmid was designated as pTrp4.

TABLE 2

| | | |
|---|---|---|
| SEQ ID NO: 3 | 5' side EcoO109I | GTATCACG<u>AGGCCCT</u>AGCTGTGGTGTCAT GGTCGGTGATC |
| SEQ ID NO: 4 | 3' side NdeI | TTCGGGGATTC<u>CATATG</u>ATACCCTTTTA CGTGAACTTGC |
| SEQ ID NO: 5 | 3' end NdeI | GGGGGGGG<u>CATATG</u>CGACCTCCTTATTAC GTGAACTTG |

(1) Construction of Plasmid ptrpPtALD Expressing an Aldolase Gene and Expression in *E. coli*

A DNA fragment amplified from *P. taetrolens* ATCC4683 chromosomal DNA using primers as shown in Table 3 (SEQ ID NOs: 6 and 7) was digested with NdeI/HINDIII, and inserted into the NdeI/HindIII site of pTrp4 to construct plasmid ptrpPtALD. This plasmid comprises a gene comprising the 456th ATG as a translation initiation codon in the base sequence as described in SEQ ID NO: 1 and expresses an aldolase gene comprising the amino acid sequence as described in SEQ ID NO: 2. Thus constructed expression plasmid was introduced into *E. coli* JM109, and a platinum loop of the resulting transformant was inoculated on 50 ml of LB medium containing 100 µg/ml of ampicillin and incubated at 37° C. with shaking for 16 hours. After completion of the incubation, the cells were collected, washed, suspended in 1 ml of 20 mM Tris-HCl (pH 7.6), and crushed with a multi-bead shocker (Yasui Kikai). The crushed solution was centrifuged at 15,000 rpm for 10 minutes and the supernatant was used as a crude enzyme solution.

TABLE 3

| | |
|---|---|
| SEQ ID NO: 6 | ALD-3'Hind (5'-CCG AAG CTT TCA GTT CGC CAG GCC AGC C-3') |
| SEQ ID NO: 7 | ALD-5'Nde-2 (5'-ATG GAG GTC CAT TAG TCA TTG CCC GGT TCA CGC-3') |

The aldolase activity was measured using the crude enzyme solution. When measuring the aldolase activity, the degradation activity of aldolase for a substrate was measured according to the following condition.

Reaction condition: 50 mM Tris-HCl (pH 8.0), 2 mM PHOG, 0.2 mM NADH, 0.2 mM KPi, 1 mM $MgCl_2$, 16U/ml lactate dehydrogenase, 3 µl enzyme/600 µl reaction mixture, 30° C., absorption measured at 340 nm.

As a result, no PHOG aldolase activity was detected in *E. coli* (control) into which pTrp4 was introduced, while 36.0 U/mg protein of the PHOG aldolase activity was detected in a ptrpPtALD-transduced strain.

Example 2

Preparation of Variant PtALD (1) Construction of a Variant-Transducing Plasmid pKFPtALD Introduction of site-specific variation into PtADL was conducted using a Mutan-Super Express Km (TaKaRa) according to the protocol attached to the kit. First, a variant-transducing plasmid pKFPtALD was constructed. Using the primers as shown in Table 4 (SEQ ID NOs: 6 and 8), a fragment containing from trp promoter to the whole length of PtALD structural gene was amplified by PCR using ptrpPtALD as template. The amplified fragment was digested with XbaI/HindIII and inserted into the XbaI/HindIII site of pKF18-2 to construct plasmid pKFPtALD.

TABLE 4

| SEQ ID NO: 6 | ALD-3'Hind<br>(5'-CCG AAG CTT TCA GTT CGC CAG GCC AGC C-3') |
|---|---|
| SEQ ID NO: 8 | XbaI TrpF<br>(5'-GCT CTA GAG AAA TGA CGT GTT GAC AAT TAA-3') |

(2) Transduction of a Site-Specific Variation into PtALD

Based on the structural information of PtALD by X-ray crystallography, a site-specific variation was introduced into R37 and L99 of PtALD, which are considered to have an influence on the asymmetry of 4-position in the enzyme reaction product, and directed between the supposed pyruvic acid-binding site and the substrate-(indolepyruvic acid, phenylpyruvic acid, etc.)-binding site in PtALD. The respective synthetic oligo-DNA primers were synthesized, which were designed to introduce the objective base substituent. Table 5 shows the produced variant enzymes and the sequences of the synthetic oligo-DNA primers used for in introduction of variation.

The name of the variant enzymes are represented in order of "the amino acid residue in a wild-type enzyme→residue number→substituted amino acid residue". For example, R37Y variant enzyme means a variant enzyme in which the 37th Arg(R) residue in a wild-type enzyme is replaced with a Tyr(Y) residue. In this regard, in order to identify the residue essential for the catalytic reaction, a variant enzyme concerning Asp 120 located in the proximity of the active center was also prepared.

TABLE 5

| SEQ ID NO: 9 | R37Y<br>(5'-CAG TGA TAA CCT CGG GTA TCA CAT CGG TGC CCG G-3') |
|---|---|
| SEQ ID NO: 10 | R37W<br>(5'-CAG TGA TAA CCT CGG GTG GCA CAT CGG TGC CCG G-3') |
| SEQ ID NO: 11 | R37H<br>(5'-CAG TGA TAA CCT CGG GCA TCA CAT CGG TGC CCG G-3') |
| SEQ ID NO: 12 | R37P<br>(5'-CAG TGA TAA CCT CGG GCC TCA CAT CGG TGC CCG G-3') |

TABLE 5-continued

| SEQ ID NO: 13 | R37F<br>(5'-CAG TGA TAA CCT CGG GTT TCA CAT CGG TGC CCG G-3') |
|---|---|
| SEQ ID NO: 14 | L99D<br>(5'-GCG GTC ATT GGT GAG GAC ATC AAG CTC TAC GCG-3') |
| SEQ ID NO: 15 | L99W<br>(5'-GCG GTC ATT GGT GAG TGG ATC AAG CTC TAC GCG-3') |
| SEQ ID NO: 16 | L99Y<br>(5'-GCG GTC ATT GGT GAG TAC ATC AAG CTC TAC GCG-3') |
| SEQ ID NO: 17 | L99G<br>(5'-GCG GTC ATT GGT GAG GGG ATC AAG CTC TAC GCG-3') |
| SEQ ID NO: 18 | L99K<br>(5'-GCG GTC ATT GGT GAG AAG ATC AAG CTC TAC GCG-3') |
| SEQ ID NO: 19 | D120A<br>(5'-GAC GGC GCC ATC CGC GCT GTC GCC AGT TTT GGA G-3') |
| SEQ ID NO: 20 | L99E<br>(5'-GCG GTC ATT GGT GAG GAG ATC AAG CTC TAC GCG-3') |
| SEQ ID NO: 21 | L99H<br>(5'-GCG GTC ATT GGT GAG CAC ATC AAG CTC TAC GCG-3') |
| SEQ ID NO: 22 | L99V<br>(5'-GCG GTC ATT GGT GAG GTG ATC AAG CTC TAC GCG-3') |

According to the method as described in the kit, a variant plasmid was prepared using pKFPtALD as a template. First, the 5' end of the synthetic oligo-DNA primer was phosphorylated at 37° C. for 30 minutes in the following condition, and after incubation at 70° C. for 5 minutes, the reaction was stopped.

| 10 × T4 polynucleotide kinase buffer | 2 µl |
|---|---|
| Synthetic oligo-DNA primer (100 pmol/L) | 1 µl |
| 10 mM ATP | 2 µl |
| T4 polynucleotide kinase | 1 µl |
| DW | 14 µl |

Using the phosphorylated oligo-DNA primer and the attached selection primer, a variant PtALD expression plasmid was amplified in the following condition. For example, in preparing pKFR37Y, pKFPtALD was used as a template to carry out PCR using the 5'-end phosphorylated primer R37Y, and E. coli JM109 was transformed with the resulting reaction mixture. Plasmid was recovered from the transformant and the base sequence was determined to confirm the successful introduction of the objective base substitution.

| 94° C. | 1 minute | |
|---|---|---|
| 55° C. | 1 minute | |
| 72° C. | 3 minutes | ×30 cycles |

Preparation of a double variant plasmid was performed by using the previously prepared single variant expression plasmid as a template coupled with introduction of one of the variation-transducing primers. For example, R37Y/L99K variant enzyme expression plasmid was prepared by PCR using pKFR37Y as a template and the 5'-end phosphorylated primer L99K. In preparing a double variant plasmid, in order to enhance the production efficiency of the variant-transducing plasmid, the template plasmid was cleaved by treating with a restriction enzyme DpnI which recognizes and cleaves a methylated DNA in a post-PCR DNA; and then *E. coli* JM109 was transformed with the resulting reaction mixture. Plasmid was recovered from the transformant and the base sequence was determined to confirm the successful introduction of the objective base substitution.

(3) Preparation of Variant PtALD Expression *E. coli*

*E. coli* transformants containing a variety of variant PtALD gene-integrated plasmids or pKFPtALD, each was inoculated on 3 ml of LB medium (Bactotripton 1 g/dl, yeast extract 0.5 g/dl, and NaCl 1 g/dl) containing 0.1 mg/ml of ampicillin and 0.1 mM isopropyl-1-thio-β-D-galactopyranoside (IPTG), and cultured at 37° C. with shaking for 16 hours. The cells were collected from the culture broth and washed to yield PtALD expression *E. coli*. Expression of the respective variant PtALDs was confirmed by SDS-PAGE. The cells collected from 250 μl of the culture broth by centrifugation were suspended into 500 μl of SDS-PAGE sample buffer and boiled for 10 minutes to lyse and denature. The supernatant (5-10 μl) obtained by centrifugation (10,000×g, 10 min) was applied on SDS-PAGE; it was confirmed that a specific band appeared at about 25 kDa in all of the strains transduced with wild-type and variant PtALD expression plasmids, confirming the expression of wild-type and variant PtALDs.

prepared from 400 μl of the culture broth by centrifugation were suspended in 200 μl of a reaction mixture of the following components, respectively.

Reaction mixture for IHOG synthesis: 100 mM Hepes-KOH (pH 8.5), 50 mM indolepyruvic acid, 200 mM sodium pyruvate, 1 mM $MgCl_2$, and 5 mM potassium phosphate buffer (pH 8.5)

Reaction mixture for PHOG synthesis: 100 mM Hepes-KOH (pH 8.5), 50 mM sodium phenylpyruvate, 200 mM sodium pyruvate, 1 mM $MgCl_2$, and 5 mM potassium phosphate buffer (pH 8.5)

The reaction mixture was incubated at 37° C. for 6 hours, and the produced IHOG or PHOG were quantitatively analyzed and their asymmetry at the position 4 was analyzed. The result is shown in Table 6. In comparison with the pKFPtALD-transduced strain (parent enzyme expression strain), the selectivity for 4R-IHOG or 4R-PHOG was recognized to improve in the variant PtALD expression strain.

With respect to the pKFD120-transduced strain, the aldol degradation activity was measured using a cell extract as an enzyme source and PHOG as a substrate in the above-mentioned condition, but no activity was detected, indicating that the transduction of variation into Asp120 eliminates the aldolase activity.

TABLE 6

| | Synthetic reaction for IHOG | | | | Synthetic reaction for PHOG | | | |
|---|---|---|---|---|---|---|---|---|
| | Yield of IHOG (mM) | 4R-isomer (mM) | 4S-isomer (mM) | 4R/4R + 4S (%) | PHOG production (mM) | 4R-isomer (mM) | 4S-isomer (mM) | 4R/4R + 4S (%) |
| R37Y | 11.4 | 6.6 | 4.8 | 58 | 14.1 | 8.3 | 5.8 | 59 |
| R37W | 9.1 | 5.6 | 3.5 | 61 | 11.2 | 6.5 | 4.7 | 58 |
| R37H | 9.9 | 5.5 | 4.4 | 56 | 8.9 | 5.3 | 3.6 | 59 |
| R37P | 9.3 | 5.8 | 3.5 | 62 | 14.1 | 8.8 | 5.3 | 62 |
| R37F | 10.7 | 6.3 | 4.4 | 59 | 12.0 | 8.0 | 4.0 | 67 |
| L99D | 9.7 | 7.4 | 2.3 | 76 | 16.2 | 11.4 | 4.8 | 71 |
| L99W | 8.8 | 5.2 | 3.6 | 59 | 7.3 | 4.9 | 2.4 | 67 |
| L99Y | 7.3 | 4.3 | 3.0 | 59 | 6.3 | 4.2 | 2.2 | 66 |
| L99G | 6.8 | 4.3 | 2.5 | 64 | 17.0 | 10.7 | 6.3 | 63 |
| L99K | 11.1 | 5.9 | 5.2 | 53 | 15.1 | 9.0 | 6.1 | 59 |
| L99E | 12.8 | 9.2 | 3.6 | 72 | 13.1 | 9.3 | 3.8 | 71 |
| R37F/L99K | 8.4 | 7.0 | 1.3 | 84 | 13.4 | 11.7 | 1.7 | 87 |
| R37Y/L99K | 10.0 | 8.0 | 2.0 | 80 | 26.1 | 22.9 | 3.2 | 88 |
| R37W/L99K | 6.3 | 4.8 | 1.5 | 76 | 14.2 | 11.9 | 2.3 | 84 |
| pKFPtALD | 10.7 | 3.7 | 7.0 | 35 | 19.5 | 10.1 | 9.4 | 52 |
| ptrp2 (control) | 2.1 | 1.2 | 0.9 | 55 | 3.1 | 1.6 | 1.5 | 51 |

Example 3

Synthetic Reaction for IHOG and PHOG using a Variant pKFPtALD-Transduced *E. coli*

IHOG and PHOG were produced with *E. coli* expressing a variety of variant PtALD prepared in Example 2. The cells Example 4

Construction of a Variant ptrapPtALD and Synthetic Reaction for IHOG and PHOG (1) Construction of a Variant ptrapPtALD and Preparation of *E. coli* Expressing a Variant PtALD A variant PtALD gene prepared using pKFPtALD as a template was linked to pTrp4 to yield a high-expression plasmid of pTrp4. This was introduced into *E. coli* to yield *E. coli* highly expressing a variant PtALD, by which the reaction for IHOG synthesis was carried out in a condition in which the initial concentration of indolepyruvic acid or phenylpyruvic acid was increased up to 300 mM; thus, the asymmetry at the position 4 was analyzed.

Using the primers as shown in Table 3 (SEQ ID NOs: 6 and 7), a DNA fragment was amplified from the plasmid DNAs of a variety of variant pKFPtALD prepared in Example 2, then digested with NdeI/HindIII, and inserted into the NdeI/HindIII of pTrp4 to construct a plasmid ptrpPtALD. For example, DNA amplified using pKFR37Y as a template was linked to pTrp4, and the resulting R37Y high-expression plasmid was designated as ptrpR37Y.

Thus constructed expression plasmid was introduced into *E. coli* JM109, and a platinum loop of the resulting transformant was inoculated on 3 ml of LB medium containing 100 μg/ml of ampicillin, and shaken at 37° C. for 16 hours. The expression of a variety of variant PtALD was confirmed by SDS-PAGE. The cells collected from 250 μl of the culture broth by centrifugation were suspended into 500 μl of SDS-PAGE sample buffer and boiled for 10 minutes to lyse and denature. The supernatant (5-10 μl) obtained by centrifugation (10,000×g, 10 min) was applied on SDS-PAGE; it was confirmed that a specific band appeared at about 25 kDa in all of the strains transduced with wild-type and variant PtALD expression plasmids, confirming the expression of wild-type and variant PtALDs.

(2) Synthetic Reaction for IHOG and PHOG Using a Variant ptrpPtALD-Transduced *E. coli*

From 1 ml of the culture broth of a variety of variant ptrpPtALD-transduced *E. coli* prepared in (1), the cells was separated by centrifugation, and suspended into 500 μl of a reaction mixture having the following components.

Reaction mixture for IHOG synthesis: 100 mM Hepes-KOH (pH 8.5), 300 mM indolepyruvic acid, 750 mM sodium pyruvate, 1 mM $MgCl_2$, and 5 mM potassium phosphate buffer (pH 8.5) (pH adjusted with 6N KOH)

Reaction mixture for PHOG synthesis: 100 mM Hepes-KOH (pH 8.5), 300 mM sodium phenylpyruvate, 750 mM sodium pyruvate, 1 mM $MgCl_2$, and 5 mM potassium phosphate buffer (pH 8.5) (pH adjusted with 6N KOH)

The reaction mixture for IHOG synthesis was incubated at 37° C. for 24 hours, and the mixture for PHOG was incubated at 37° C. for 6 hours, respectively. The produced IHOG or PHOG were quantitatively analyzed and their asymmetry at the position 4 was analyzed. The result is shown in Table 7. In comparison with the ptrpPtALD-transduced strain (parent enzyme expression strain), the selectivity for 4R-IHOG or 4R-PHOG was recognized to improve in the variant PtALD expression strain thus produced.

Example 5

Synthesis of IHOG by R37Y/L99K Variant Aldolase

The cells of *E. coli* JM109/ptrpR37Y/L99K strain that had been incubated on a LB-amp plate at 37oC for 16 hours were picked up with a platinum loop and inoculated on 50 ml of LB-amp medium placed in each of 20 flasks of 500 ml-volume, and incubated at 37° C. with shaking for 16 hours. The cells were collected from the culture broth by centrifugation, then suspended in Buffer A (20 mM Hepes-KOH, pH 7.6) for washing, and again collected by centrifugation. The cells (wet weight: about 5 g) collected by centrifugation was suspended in 500 ml of a reaction mixture of the following components.

Reaction mixture for IHOG synthesis: 50 mM Hepes-KOH (pH 8.5), 200 mM indolepyruvic acid, 500 mM sodium pyruvate, 1 mM $MgCl_2$, and 5 mM potassium phosphate buffer (pH 8.5) (adjusted at pH 8.5 with 6N KOH)

Argon gas was passed through the cell-suspended reaction mixture, and thereafter the reaction was conducted under argon atmosphere. The reaction was continued at 37° C. with stirring for 21 hours. After the reaction completion, the cells were removed by centrifugation to give 495 ml of aldol reaction mixture.

Example 6

Oxime Formation for the Aldol Reaction Mixture and Isolation of 4R-IHOG-oxime

The aldol reaction mixture obtained in Example 5 was kept at pH 9 with 8N sodium hydroxide aqueous solution, to which 27.1 g (391 mmol) of hydroxylamine hydrochloride was added and stirred at 5° C. for 20 hours. The amount of IHOG-oxime produced in the reaction mixture was quantitatively analyzed by HPLC. As a result, it was found that 26 mmol of 4-hydroxy-4-(3-indolylmethyl)-2-hydroxyiminoglutaric acid (IHOG-oxime) was produced. Analysis of the asymmetry at the position 4 indicated that the product contained 21.3

TABLE 7

| | Synthetic reaction for IHOG | | | | Synthetic reaction for PHOG | | | |
|---|---|---|---|---|---|---|---|---|
| | Yield of IHOG (mM) | 4R-isomer (mM) | 4S-isomer (mM) | 4R/4R + 4S (%) | Yield of PHOG (mM) | 4R-isomer (mM) | 4S-isomer (mM) | 4R/4R + 4S (%) |
| ptrpR37F | 119.6 | 66.6 | 53.0 | 56 | 202.3 | 101.5 | 100.7 | 50 |
| ptrpR37Y | 22.2 | 11.3 | 10.9 | 51 | 81.0 | 44.5 | 36.5 | 55 |
| ptrpR37W | 42.9 | 29.8 | 13.1 | 69 | 196.8 | 99.1 | 97.7 | 50 |
| ptrpR37P | 26.1 | 14.9 | 11.2 | 57 | 180.6 | 97.3 | 83.3 | 54 |
| ptrpR37H | 141.6 | 70.2 | 71.4 | 50 | 199.5 | 99.6 | 99.9 | 50 |
| ptrpL99D | 95.1 | 65.5 | 29.6 | 69 | 210.9 | 107.4 | 103.5 | 51 |
| ptrpL99H | 128.5 | 65.3 | 63.2 | 51 | 205.0 | 103.5 | 101.4 | 51 |
| ptrpL99W | 66.0 | 38.8 | 27.2 | 59 | 173.8 | 89.2 | 84.6 | 51 |
| ptrpL99Y | 124.5 | 63.6 | 60.8 | 51 | 206.2 | 103.8 | 102.4 | 50 |
| ptrpL99K | 111.7 | 66.6 | 45.1 | 60 | 194.7 | 101.9 | 92.8 | 52 |
| ptrpL99G | 30.8 | 19.5 | 11.3 | 63 | 201.4 | 105.1 | 96.3 | 52 |
| ptrpL99V | 101.0 | 50.9 | 50.1 | 50 | 187.2 | 93.7 | 93.5 | 50 |
| ptrpL99E | 108.8 | 64.7 | 44.1 | 59 | 199.3 | 102.9 | 96.4 | 52 |
| ptrpR37F/L99K | 49.7 | 39.8 | 9.9 | 80 | 188.5 | 145.5 | 43.0 | 77 |
| ptrpR37W/L99K | 22.7 | 12.2 | 10.5 | 54 | 167.9 | 129.3 | 38.6 | 77 |
| ptrpR37Y/L99K | 76.1 | 63.4 | 12.7 | 83 | 184.8 | 159.9 | 24.9 | 87 |
| ptrpPtALD | 116.2 | 57.9 | 58.2 | 50 | 206.4 | 103.5 | 102.9 | 50 |
| ptrp4 (control) | 23.6 | 12.5 | 11.1 | 53 | 72.1 | 36.0 | 36.1 | 50 | mmol of 4R-IHOG-oxime and 4.7 mmol of 4S-IHOG-oxime, demonstrating that the 4R-isomer was predominantly produced in e.e.=64.2%.

The resulting reaction mixture was adjusted at pH 2 with conc. hydrochloric acid, and the organic materials were extracted with ethyl acetate. The organic layer was condensed to yield a residue. To the residue was added 20 ml of 28% ammonia water and 15 ml of water. There was added 170 ml of 2-propanol for crystallization to yield 11.18 g (wet weight) of 4-hydroxy-4-(3-indolylmethyl)-2-hydroxyiminoglutaric acid 2 ammonium salt as crystals. Thus obtained crystals were dissolved in 60 ml of water, to which was added 200 ml of 2-propanol for recrystallization. Recrystallization was repeated twice to yield 4.54 g (13.4 mmol) of IHOG-oxime 2 ammonium salt. The resulting crystals were analyzed on asymmetry at the position 4, indicating that the e.e. value as 4R-isomer was 99.7%. Thus, the 4R-IHOG-oxime ammonium salt was isolated by crystallization from 2-propanol.

Example 7

Production of 4R-monatin from 4R-IHOG-oxime by Chemical Reduction (4R)-4-Hydroxy-4-(3-indolylmethyl)-2-hydroxyiminoglutaric acid ammonium salt (4.39 g; 12.9 mmol) obtained in Example 6 was dissolved in 45 ml of 28% ammonia water, to which was added 2.31 g of 5% rhodium carbon (50% water content), and the mixture was hydrogenated at 25° C. under pressure of 1 MPa. After a lapse of 24 hours, the catalyst was filtered off (0.2 micron filter) to give filtrate, in which potassium carbonate was dissolved. The solution was condensed, and the condensate (10.9 g) was added 6.7 ml of water and 15 ml ethanol. The mixture was stirred at 25° C., to which was dropwise added 20 ml of ethanol over 3 hours, and further stirred at 25° C. for 20 hours.

The resulting wet crystals (3.26 g) were dissolved in 4 ml of water, and after addition of 8 ml of ethanol, there was further dropwise added 17 ml of ethanol over 3 hours. The ethanol solution was cooled to 15° C. over 4 hours, and stirred at 15° C. for 10 hours. The resulting wet crystals (2.36 g) were dried under reduced pressure to yield 1.9 g of the objective (2R,4R)-monatin K salt.

Example 8

Purification of a Recombinant Aldolase Enzyme Derived from *Pseudomonas taetrolens* ATCC4683 Strain From the soluble fraction of *E. coli* that highly expressed an aldolase (hereinafter, PtALD) derived from *Pseudomonas taetrolens* ATCC4683, a recombinant PtALD was purified as follows. The aldolase activity was measured based on the aldol degradation activity using PHOG as a substrate in the following condition.

Reaction condition: 50 mM Tris-HCl (pH 8.0), 2 mM PHOG, 0.2 mM NAD, 0.2 mM Kpi, 1 mM $MgCl_2$, 16 U/ml lactate dehydrogenase, 3 μl enzyme/600 μl reaction mixture, 30° C., absorption measured at 340 nm (1) Preparation of a Soluble Fraction:

The cells of *E. coli* JM 109/ptrpALD that had been incubated on an LB-amp plate at 37oC for 16 hours were picked up with a platinum loop, inoculated on 3 ml of LB-amp medium placed in a test tube, and incubated at 37° C. with shaking for 16 hours. 0.5 ml portions of the culture broth were inoculated to ten 500 ml-volume flasks containing 50 ml of LB-amp medium and incubated at 37° C. with shaking for 16 hours. The cells were collected from the culture broth by centrifugation, suspended in and washed with Buffer A (20 mM Hepes-KOH; pH 7.6), and again centrifuged. The washed cells were suspended in 25 ml of Buffer A and crushed by ultra-sonication at 4° C. for 30 minutes. The crushed solution was centrifuged (×8000 rpm, 10 min×2) to remove the cells residue, and the supernatant was used as a crude extract fraction.

(2) Anion Exchange Chromatography: Q-Sepharose FF

The above-mentioned crude extract fraction (23 ml) was adsorbed on an anion exchange column Q-Sepharose FF 26/10 for chromatography (Pharmacia; CV=20 ml) equilibrated with Buffer A. The proteins which were not adsorbed on the carrier (non-adsorbed proteins) were washed out with Buffer A, and then the adsorbed protein was eluted with 0M to 0.7M linear gradient concentration of KCl (total 140 ml). The PHOG aldolase activity of each fraction was detected, and it was found that the fraction corresponding to about 0.5M showed the peak of PHOG aldolase activity.

(3) Hydrophobic Chromatography: Phenyl Sepharose HP HR 16/10

The solution in which the aldolase activity was detected was dialyzed to Buffer B (20 mM Hepes-KOH (pH 7.6), 1M ammonium sulfate; pH 7.6) at 4° C. overnight, then centrifuged at 10000 rpm for 10 minutes, and the supernatant was filtered through a 0.45 μm filter. The resulting filtrate was applied to a hydrophobic chromatography using a column Phenyl Sepharose HP HR 16/10 (Pharmacia) equilibrated with Buffer B. In this operation, aldolase was adsorbed on the carrier.

Non-adsorbed proteins that were not adsorbed on carrier were washed out with Buffer B, and then the aldolase was eluted with 1M to 0M linear gradient concentration of ammonium sulfate. The aldolase activity of each eluted fraction was detected, and it was found that the fraction corresponding to about 0.2M ammonium sulfate concentration showed the peak of PHOG aldolase activity.

The fraction purified by column chromatography as mentioned above was applied to SDS-PAGE; as a result, a single band stained by CBB was detected at the position corresponding to about 25 kDa. Thus obtained recombinant PtALD solution was dialyzed to Buffer A at 4° C. overnight. In the above operation, 17 ml of 350 U/ml PtALD solution was obtained.

Example 9

Crystallization of PtALD

The purified enzyme solution of PtALD obtained in Example 8 was condensed at 4° C. by ultrafiltration using Centriprep 10 (fractionation molecular weight 10 kDa). As for the resulting condensed enzyme solution (20.3 mg/ml), a condition for crystallization was searched using a crystal screen kit (Hampton Research). A variety of precipitants (2 μL) was blended with a PtALD solution (2 μL), and crystallization was attempted by a sitting drop vapor diffusion method. As a result, when 1M ammonium phosphate and 0.1M sodium citrate (pH 5.6) were used as precipitants at 4° C., columnar crystals (0.1 mm×0.1 mm×1 mm) were obtained within a period of 2-3 days.

In addition, the crystals of the complex of PtALD with PHOG or IHOG-oxime were obtained. PHOG and IHOG-oxime were prepared according to the methods of Reference Examples 1 and 2 as mentioned below. A condensed enzyme solution (20 mg/ml; 2 µL), a solution of the above-mentioned precipitant solution (2 µL), and 10 mM PHOG solution or IHOG-oxime/2NH$_3$ solution (1 µL) were blended and crystallized by a sitting drop vapor diffusion method, and incubated at 4° C. for 2-3 days to yield crystals.

Example 10

X-Ray Crystallography of PtALD Native Crystals

Since the crystals of PtALD are degraded by X-ray damage at room temperature and the diffractivity is gradually decreased, the diffraction intensity by X-ray was measured in a condition of lower temperature. The crystals were moved into 0.15M sodium citrate buffer (pH 5.6) containing 25% glycerol and 1.5M ammonium phosphate, and rapidly cooled to −173° C. by blowing nitrogen gas. The X-ray diffraction data of PtALD native crystals was collected using an X-ray diffractometer R-AXIS V++ (Rigaku Co., Ltd.) at the Photon Factory Beamline 6B of the High Energy Accelerator Research Organization (Tsukuba, Japan). The X-ray wavelength was fixed at 1.0 angstrom and the distance from the crystal to an imaging plate detector was 180 mm. Exposure time and an oscillation angle per one imaging plate frame were 120 sec and 0.8°, respectively, and the data for 150 frames was collected. In the crystallographic parameters, the space group was P6$_3$22, and the lattice constants were a=94.38 angstrom and c=111.49 angstrom. The asymmetric unit contains one aldolase molecule, and the water content of the crystal was 60%. The crystal was diffracted to approximately 1.5 angstrom resolution. The data processing was made with a program Crystal Clear (Rigaku Co., Ltd.). The R$_{merge}$, which indicates the quality of the data, was 0.097 between 40.0-1.5 angstrom resolution, and 0.260 between 1.55-1.50 angstrom resolution in the most outer shell. The completeness of the data was 99.2% between 40.0-1.5 angstrom resolution, and 99.9% between 1.55-1.50 angstrom resolution in the most outer shell.

Subsequently, the PtALD crystals were soaked in a heavy metal salt solution, and the heavy metal derivative crystal was screened. The X-ray diffraction data of the crystal soaked in a heavy metal salt solution was also collected using an X-ray diffractometer R-AXIS V++ (Rigaku Co., Ltd.) at the Photon Factory Beamline 6B of the High Energy Accelerator Research Organization (Tsukuba, Japan). Two crystals, that is, a crystal which was soaked in 0.18M sodium citrate buffer (pH 5.6) containing 1.0 mM ethyl mercury thiosalicylic acid (EMTS) and 1.8M ammonium phosphate for about one day, and another crystal which was soaked in 0.18M sodium citrate buffer (pH 5.6) containing 2.5 mM HgCl$_2$ and 1.8M ammonium phosphate for about one day, were found to be good heavy atom derivative crystals from a difference Patterson map to the data of native crystal.

Concerning the heavy atom derivative crystal of EMTS, a major heavy atom site was obtained from the difference Patterson map, and a difference Fourier map was calculated using the phase calculated from this coordinate to determine the other plural minor heavy atom sites. The coordinates and occupancies of these heavy atom sites were precisely refined by means of a phase-determining program MLPHARE contained in a protein structural analysis program package CCP4 (Acta Crystallogr. Sect. D, vol. 50, 760-763 (1993)), and the initial phase was calculated. Solvent flattening and histogram matching were made using a phase-improving program DM contained in the same CCP4 to improve the phase. Based on the improved phase, an electron density map of 2.7 angstrom resolution was calculated and drawn on a computer graphics program QUANTA (Accelrys). A clear electron density map was drawn, by which all of the amino acid residues of PtALD except the C-terminal Asn 221 could be fitted to the electron density.

Thus constructed initial molecular model was refined using a program CNX (Accelrys). The final model (FIGS. 1, 4 and 5) refined with the X-ray data up to 1.5 angstrom resolution comprises all of the amino acid residues from Ser 2 to Ala 220 of PtALD, one phosphate ion, and 341 molecules of water. The phosphate ion is located at near the binding site of the substrate pyruvic acid (FIG. 5). In the crystallographic reliability factors determined by reflections between 40.0-1.5 angstrom resolution, R$_{cryst}$ was 19.9% and R$_{free}$ 22.7%. Deviations from the ideal values of the atom-atom bond distance and the bond angle in the protein molecule were 0.0079 angstrom and 1.6313°, respectively, as root mean square error values. Ramachandran plot was made using a program PROCHECK (J. Appl. Crystallogr., vol. 26, 283-291 (1993)), indicating that 91.7% of the 180 residues except glycine are located at the best region, and the remaining 8.3% at the second good region, and that all of the residues have a sufficiently acceptable dihedral angle of peptide bond. An atomic coordinate of the PtALD native crystal is shown in FIG. 9-1 to FIG. 9-26.

Example 11

X-Ray Crystallography of the Crystal of PtALD-PHOG Complex

The crystals obtained by co-crystallization of PtALD and PHOG were moved into 0.15M sodium citrate buffer (pH 5.6) containing 10 mM PHOG, 25% glycerol and 1.5M ammonium phosphate, and rapidly cooled to −173° C. by blowing nitrogen gas. The X-ray diffraction data of the crystals was collected using an X-ray diffractometer R-AXIS V++ (Rigaku Co., Ltd.) at the Photon Factory Beamline 6B of the High Energy Accelerator Research Organization (Tsukuba, Japan). The X-ray wavelength was fixed at 1.0 angstrom and the distance from the crystal to an imaging plate detector was 180 mm. Exposure time and an oscillation angle per one imaging plate frame were 120 sec and 0.8°, respectively, and the data for 60 frames was collected. In the crystallographic parameters, the space group was P6$_3$22, and the lattice constants were a=94.37 angstrom and c=111.67 angstrom, indicating that approximately the same crystals as the native ones were given. The crystal was diffracted to approximately 1.8 angstrom resolution. The data processing was made with a program Crystal Clear (Rigaku Co., Ltd.). The factor of data quality, R$_{merge}$ was 0.097 between 40.0-1.8 angstrom resolution, and 0.201 between 1.86-1.80 angstrom resolution in the most outer shell. The completeness of the data was 99.2% between 40.0-1.8 angstrom resolution, and 99.5% between 1.86-1.80 angstrom resolution in the most outer shell.

An electron density map was calculated based on the structure of the native crystals and observed on a computer graphics program QUANTA (Accelrys), from which it was confirmed that a PHOG-like electron density clearly existed on the interface between the adjacent two subunits. A molecular model of PHOG was constructed thereon. There was almost no change on the protein portion from the structure of native crystal. Subsequently, the structure was refined using a program CNX (Accelrys). The final model (FIGS. 2 and 6) refined with the X-ray data up to 1.8 angstrom resolution comprises all of the amino acid residues from Ser 2 to Ala 220 of PtALD, one molecule of PHOG, and 295 molecules of water. In the crystallographic reliability factors determined by reflections between 40.0-1.8 angstrom resolution, $R_{cryst}$ was 19.8% and Rfree 24.2%. Deviations from the ideal values of the atom-atom bond distance and the bond angle in the protein were 0.0076 angstrom and 1.4883°, respectively, as root mean square error values. Ramachandran plot was made using a program PROCHECK, indicating that 93.9% of the 180 residues except glycine are located at the best region, and the remaining 6.1% at the second good region, and that all of the residues have a sufficiently acceptable dihedral angle of peptide bond.

Example 12

X-Ray Crystallography of the Crystal of PtALD-IHOG-Oxime Complex

The crystals obtained by co-crystallization of PtALD and IHOG-oxime were moved into 0.15M sodium citrate buffer (pH 5.6) containing 10 mM IHOG-oxime $2NH_3$, 25% glycerol and 1.5M ammonium phosphate, and rapidly cooled to −173° C. by blowing nitrogen gas. The X-ray diffraction data of the crystals was collected using an X-ray diffractometer R-AXIS V++ (Rigaku Co., Ltd.) at the Photon Factory Beamline 6B of the High Energy Accelerator Research Organization (Tsukuba, Japan). The X-ray wave length was fixed at 1.0 angstrom and the distance from the crystal to an imaging plate detector was 180 mm. Exposure time and an oscillation angle per one imaging plate frame were 120 sec and 0.8°, respectively, and the data for 100 frames was collected.

In the crystallographic parameters, the space group was $P6_322$, and the lattice constants were a=94.75 angstrom and c=111.84 angstrom, indicating that approximately the same crystals as the native ones were given. The crystal was diffracted to approximately 2.2 angstrom resolution. The data processing was made with a program Crystal Clear (Rigaku Co., Ltd.). The factor of data quality, $R_{merge}$ was 0.097 between 40.0-2.15 angstrom resolution, and 0.203 between 2.25-2.15 angstrom resolution in the most outer shell. The completeness of the data was 98.7% between 40.0-2.15 angstrom resolution, and 98.7% between 2.25-2.15 angstrom resolution in the most outer shell.

An electron density map was calculated based on the structure of the native crystals and observed on a computer graphics program QUANTA (Accelrys), from which it was confirmed that an IHOG-oxime-like electron density clearly existed on the interface between the adjacent two subunits. A molecular model of IHOG-oxime was constructed thereon. There was almost no change on the protein portion from the structure of native crystal. Subsequently, the structure was refined using a program CNX (Accelrys). The final model (FIGS. 3 and 7) refined with the X-ray data up to 2.2 angstrom resolution comprises all of the amino acid residues from Ser 2 to Ala 220 of PtALD, one molecule of IHOG-oxime, and 287 molecules of water.

In the crystallographic reliability factors determined with reflections between 40.0-2.2 angstrom resolution, $R_{cryst}$ was 21.7% and $R_{free}$ 25.6%. Deviations from the ideal values of the atom-atom bond distance and the bond angle in the protein were 0.0140 angstrom and 1.7532°, respectively, as root mean square error values. Ramachandran plot was made using a program PROCHECK, indicating that 92.8% of the 180 residues except glycine are located at the best region, and the remaining 7.2% at the second good region, and that all of the residues have a sufficiently acceptable dihedral angle of peptide bond.

Example 13

Protein of Which the Three-Dimensional Structure is Similar to That of PtALD in the Threading Method Concerning the following 4 sequences, the three-dimensional structural similarity of the respective proteins to that of PtALD was analyzed using a program SeqFold for the Threading method included in Accelrys' software Insight II version 2000.1.

Aldolase derived from *Pseudomonas taetrolens* (PtALD): an enzyme for which the three-dimensional structure was analyze Aldolase derived from *Pseudomonas coronafaciens* (PcALD):

homology to PtALD: 40.6%

Aldolase derived from *Arthrobacter keyseri* (PcmE): homology to PtALD: 28.0%

Aldolase derived from *Pseudomonas ochraceae* (ProA):

homology to PtALD: 29.3%

Information on the theory and procedure of SeqFold is available through internet from the home page (address: http://www.accelrys.com/doc/life/insight20000.1/SeqFold). In SeqFold, the secondary structural information of individual proteins (information on which residue takes any type of the secondary structure such as α-helix, β-sheet, etc.) is converted into a database, which is compared with the prediction of the secondary structure of the objective sequence to judge the similarity of the three-dimensional structure. In this analysis, the SeqFold database was first reconstructed. That is, among the three-dimensional structure recorded in Protein Data Bank (PDB), the secondary structural information relating to 6027 sorts of the structure of which the sequence homology was 95% or less was converted into a database; the secondary structural information of PtALD was added to this data base, which was used as a data base. The secondary structural information of PtALD was calculated with Accelys' Command Script create_1d_prof.p1 by a program Insight II using the coordinate data of the PtALD three-dimensional structure (FIG. 9-1 to FIG. 9-26) as an input data. FIG. 10 shows the secondary structural information of PtALD. FIG. 10 shows the 2nd to 220th amino acid sequence for which the three-dimensional structure has been determined. The code name of PtALD in the database was designated as 9ald_A. The electronic file name of database per se is pdb95+9ald.1d_prf. In processing the Threading method, a parameter set-up screen was invoked from the graphics user interface of Insight II by a pull-down menu Homology:Seq-Fold/Fold_Search, wherein a variety of parameters were established. The followings describe the details, which are based on the developer's recommendation.

| | |
|---|---|
| Scoring_Defaults: | seqseq |
| Score_Parameters: | on |
| Substitution_Matrix: | Gonnet |
| Seq_Weight: | 1.00 |
| Sec_Weight: | 0.6 |
| Align_Parameters: | on |
| Align_Type | Global_Local |
| Max_Top_Scores: | 50 |
| Max_Top_Alignments: | 25 |
| Change_Fold_Lib: | on |
| Fold_Library: | pdb95+9ald.1d_prf |
| Change_Fold_Path: | off |
| Quick_Z_Score: | off |
| Random_Alignments: | 500 |

-continued

| | |
|---|---|
| Gap_Parameters: | on |
| Struct_Gap_Open: | 10.8 |
| Struct_Gap_Extend: | 0.6 |
| Struct_Gap_Terminal: | 0.6 |
| Seq_Gap_Open: | 10.8 |
| Seq_Gap_Extend: | 0.6 |
| Seq_Gap_Terminal: | 0.00 |

FIG. 11 to FIG. 14 show parts of the analytical results by the Threading method. In each graph (10), the x axis id indicates homology, and the y axis raw max does the abbreviated SeqFold Total Score (raw) which is one of estimation functions of SeqFold in the Threading method. Each graph (10) was made by plotting the SeqFold Total Score (raw) values for the structure which is above 25th in rank; the left end list (11) indicates the PDB code name of 25 sorts of the structure higher in rank. In this situation, the three-dimensional structure of PtADL is shown by the code name "9ald_A_. . . . " The right end list (12) shows the estimation values calculated by the Threading method for the higher ranking 25 sorts of the structure described in the left end list (11); in this list, the left end column (the column of the list) indicates the SeqFold Total Score (raw) values.

In the result of performing the Threading method for the PtALD sequence (FIG. 11), the SeqFold Total Score (raw) value for its own structure is great as high as 1016.86, indicating that the calculation and processing have been conducted accurately, and further suggesting that PtALD has a new type of three-dimensional structure quite different from the structurally known proteins.

On the other hand, in PcALD, PcmE and ProA (FIGS. 12, 13 and 14), the SeqFold Total Score (raw) values for the other structurally known proteins of which the homology is about 25% is approximately 100, while the SeqFold Total Score (raw) values for PtALD are as high as 504.44, 320.74 and 364.34, respectively, suggesting that these aldolases have very similar structure to PtALD. Table. 8 shows the total estimation value (SeqFold Total Score (bit)) together with the estimation results using the other estimation functions. This total estimation also reaches the same conclusion as described above. The threshold on which a protein is determined to have the three-dimensional structure similar to that of PtALD is considered approximately 100 as a value of SeqFold Total Score (bit).

TABLE 8

| | PtALD | PcALD | PcmE | ProA |
|---|---|---|---|---|
| SeqFold Total Score (bit) for 3-dimensional structure of PtALD | 334.50 | 165.94 | 105.51 | 119.85 |
| SeqFold Total Score (bit) for the 2nd 3-dimensional structure | 35.96 | 37.16 | 33.97 | 32.73 |

By performing the Threading method, it is possible to align a searched sequence with the sequence of a structurally known protein contained in a data base. FIG. 15 represents alignment of the amino acid sequences of PtALD and an aldolase derived from *Pseudomonas coronafaciens*. The asterisk (*) indicates a conserved amino acid residue. FIG. 16 represents alignment of the amino acid sequences of PtALD and an aldolase derived from *Arthrobacter keyseri*. The asterisk (*) indicates a conserved amino acid residue. Further, FIG. 17 represents alignment of the amino acid sequences of PtALD and an aldolase derived from *Arthrobacter keyseri*. The asterisk (*) indicates a conserved amino acid residue.

Reference Example 1

Synthesis of 4-phenylmethyl-4-hydroxy-2-ketoglutaric acid (PHOG)

To a solution of 13.8 g of potassium hydroxide (85% purity) dissolved in 25 ml of water were added 5.0 g (30.5 mmol) of phenylpyruvic acid and 12.1 g (91.4 mmol) of oxalacetic acid, and the mixture was allowed to react at room temperature for 72 hours. The reaction mixture was adjusted at pH 2.2 with conc. hydrochloric acid and extracted with ethyl acetate. The organic layer was washed with saturated brine, dried on anhydrous magnesium sulfate, and condensed to yield a residue. This was recrystallized from ethyl acetate and toluene to yield 2.8 g (11.3 mmol) of 4-phenylmethyl-4-hydroxy-2-ketoglutaric acid as crystals.

Measurement of NMR $^1$H NMR (D$_2$O) δ: 2.48 (d, J=14.4 Hz, 0.18H), 2.60 (d, J=14.4 Hz, 0.18H), 2.85-3.30 (m, 3.64H), 7.17-7.36 (m, 5H)

Measurement of Molecular Weight

ESI-MS: Calcd. for $C_{12}H_{12}O_6$=252.23; Found: 251.22 (MH−)

Reference Example 2

Synthesis of 4-hydroxy-4-(3-indolylmethyl)-2-hydroxyiminoglutaric acid 2 ammonium salt (IHOG-oxime 2NH$_3$)

In 917 g of 1.6 wt % sodium hydroxide aqueous solution was dissolved 73.8 g (352 mmol) of indole-3-pyruvic acid. The reaction mixture was kept at 35° C. while adjusting at pH 11.1 with 30% sodium hydroxide aqueous solution; and there was dropwise added 310.2 g (1761 mmol) of 50% pyruvic acid aqueous solution over 2 hours. The reaction was further continued for 4.5 hours to yield a reaction mixture containing 4-hydroxy-4-(3-indolylmethyl)-2-ketoglutaric acid. Then, 367.2 g (2114 mmol) of 40% hydroxylamine hydrochloride aqueous solution was added thereto while keeping at pH 7 with 30% sodium hydroxide aqueous solution, and the mixture was stirred at 5° C. for 17.5 hours. The reaction mixture was adjusted at pH 2 with conc. hydrochloric acid and extracted with ethyl acetate. The organic layer was washed with a saturated brine and condensed to yield a residue. The residue was recrystallized from 60 ml of 28% ammonia water and 1350 ml of 2-propanol to yield 43.4 g (142 mmol; 40% yield for indole-3-pyruvic acid) of 4-hydroxy-4-(3-indolylmethyl)-2-hydroxyiminoglutaric acid 2 ammonium salt as crystals.

As evidenced by the foregoing, the use of a variant aldolase of the invention allows optically selective production of IHOG and PHOG. The variant aldolase of the invention allows efficient introduction of an asymmetry at the step of aldol condensation reactions in a synthetic route for monatin, and can be utilized in production of an optically active IHOG and an optically active monatin.

Numerous modifications and variations on the present invention are possible in light of the above teachings. It is, therefore, to be understood that within the scope of the accompanying claims, the invention may be practiced otherwise than as specifically described herein.

The invention claimed is:

1. An isolated protein having an aldolase activity which catalyzes at least one aldol condensation reaction selected from the group consisting of (a) reaction of indole-3-pyruvic acid with pyruvic acid to yield 4-(indol-3-ylmethyl)-4-hydroxy-2-oxoglutaric acid having an optical activity due to the 4-asymmetric carbon, and (b) reaction of phenylpyruvic acid with pyruvic acid to yield 4-phenylmethyl-4-hydroxy-2-oxoglutaric acid having an optical activity due to the 4-asymmetric carbon, and which comprises the following amino acid sequences (A) or (B):

(A) in the amino acid sequence of SEQ ID NO: 2, an amino acid sequence substituted at one or both one amino acid residue selected from the following items (a) and (b):
  (a) substitution of another amino acid residue for the 37th arginine residue;
  (b) substitution of another amino acid residue for the 99th leucine residue;
(B) in the amino acid sequence of (A), an amino acid sequence having the substitution, deletion, insertion and/or addition of one to 30 amino acid residues at the positions other than 37, 67, 71, 97, 98, 99, 100, 119, 120, 139, 141, 189, 192, 193, and 209.

2. The protein as claimed in claim 1 in which the substitution of the item (a) comprises substitution of the following item (a'):
  (a') substitution of a tyrosine, tryptophan, histidine, phenylalanine or proline residue for the 37th arginine residue.

3. The protein as claimed in claim 1 in which the substitution of the item (b) comprises substitution of the following item (b'):
  (b') substitution of a aspartic acid, glutamic acid, lysine, tryptophan, tyrosine or glycine residue for the 99th leucine residue.

4. The protein as claimed in claim 1, wherein said protein has an aldolase activity which catalyzes at least one aldol condensation reaction selected from the group consisting of (a) a reaction of indole-3-pyruvic acid with pyruvic acid to yield predominantly the 4R-isomer of 4-(indol-3-ylmethyl)-4-hydroxy-2-oxoglutaric acid, and (b) a reaction of phenylpyruvic acid with pyruvic acid to yield predominantly the 4R-isomer of 4-phenylmethyl-4-hydroxy-2-oxoglutaric acid.

* * * * *